US011041165B2

(12) United States Patent
Kiss et al.

(10) Patent No.: US 11,041,165 B2
(45) Date of Patent: Jun. 22, 2021

(54) **IDENTIFICATION OF A *XANTHOMONAS EUVESICATORIA* RESISTANCE GENE FROM PEPPER (*CAPSICUM ANNUUM*) AND METHOD FOR GENERATING PLANTS WITH RESISTANCE**

(71) Applicant: Two Blades Foundation,

(56) References Cited

OTHER PUBLICATIONS

Segarra, et al.; Genome-wide analyses of the transcriptomes of salicylic acid-deficient versus wild-type plants uncover Pathogen and Circadian Controlled 1 (PCC1) as a regulator of flowering time in *Arabidopsis*, Plant, Cell & Environment (2010), vol. 33, pp. 11-22.

* cited by examiner

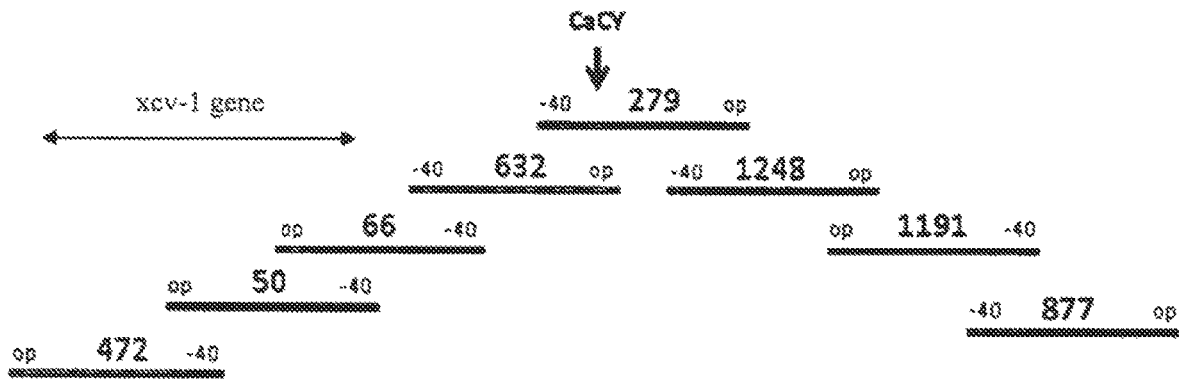

Figure 1. The xcv contig physically covering the *xcv-1* gene with overlapping BAC clones Scheme of the identified and overlapping BAC clones (horizontal lines) The numbering of the BAC clones is indicated above the lines. The two ends of the BAC clones are by "-40" and "op", respectively. The initial marker is indicated by an arrow CaCY (its primers: CaCY F1 (SEQ ID NO:1), CaCY R1 (SEQ ID NO:2). Markers of the each BAC termini: BAC 279 op F1 (SEQ ID NO:3), BAC 279 op R1 (SEQ ID NO:4), BAC 279 (SEQ ID NO:5), BAC 279 (SEQ ID NO:6), BAC 1248 op F1 (SEQ ID NO:7), BAC 1248 op R1 (SEQ ID NO:8), BAC 1248 -40 F1 (SEQ ID NO:9), BAC 1248 -40 R1 (SEQ ID NO:10), BAC 1191 -40 F1 (SEQ ID NO:11), BAC1191 -40 R1 (SEQ ID NO:12), BAC 1191 op F1 (SEQ ID NO:13), BAC 1191 op R1 (SEQ ID NO:14), BAC 877 -40 F1 (SEQ ID NO:15), BAC 877 -40 R1 (SEQ ID NO:16), BAC 632 op F1 (SEQ ID NO:17), BAC 632 op R1 (SEQ ID NO:18), BAC 632 -40 F1 (SEQ ID NO:19), BAC 632 -40 R1 (SEQ ID NO:20), BAC 66 op F1 (SEQ ID NO:21), BAC 66 op R1 (SEQ ID NO:22), BAC 66 -40 F1 (SEQ ID NO:23), BAC 66 -40 R1 (SEQ ID NO:24), BAC 50 op F1 (SEQ ID NO:25), BAC 50 op R1 (SEQ ID NO:26), BAC 50 -40 F1 (SEQ ID NO:27), BAC 50 -40 R1 (SEQ ID NO:28), BAC 472 -40 F1 (SEQ ID NO:29), BAC 472 -40 R1 (SEQ ID NO30:), BAC op F1 (SEQ ID NO:31), BAC op R1 (SEQ ID NO:32).

"DAS" TM-segment prediction

The position of amino acids of Xcv-1 protein (SEQ ID NO:42)

Figure 2. Hydrophobicity curve of the Xcv-1 protein

The part above the line marked by "0" is that part of the protein which is presumably localised in the membrane. TM = transmembrane, DAS: "Dense Alignment Surface" algoritmus

```
                                           CysCysCysCysLeuLeuAspAlaCysPhe
target mRNA (SlXcv1A/SlXcv1B)   5'-GCUGCUCUGUGCUGUUGCUGUCUCUUGGAUGCAUGCUUUUGA-3'
                                   -::::::-:::::::::::::::-
SlXe1-amiRNA                    3'-CACAACUACAGAGAACCUACU-5'
```

Figure 3. The point of attack (middle line) of the target mRNA (SlXcv-1A / SlXcv-1B genes), the amino acid sequence deducible from that (upper line), and the designed 21-bp SlXe1-amiRNA sequence (lower line).

Figure 4. Autoradiogram of the SlXe1-amiRNS RNA "Northern" blot

Northern blot of RNA hybridized to $^{32}$ATP labelled SlXe1-amiRNAs. Samples:
   1 = control
   2-3 = RNA samples isolated from two independent plants carrying the SlXe1-amiRNA expression construct
   M = smallRNA molecular weight marker (20 bp, 21 bp, 30 bp).

5A.

Part of CYSTM region of the *SlXcv-1A* gene (see SEQ ID NO: 49 for the entire sequence):

```
  2244. bp                                                                        2318.bp
    | TALEN-L >>>>>>>>>>>>>>>>  CRISPR                                               |
5'- TTTTGCAGTTTGGCTGCTGTCGTAATGCTGTCTTTGATGCATGCTTTTGATGCTGTAAATGATCTGTGCCA -3'
              ZNF-L   >>>>>>>>>>>>
                                                     <<<<<<<<<<<<<<<<  TALEN-R1
3'- AAAACGTCAAACCGACGAGACACGACAACGACAGAGAACCTACGTACGAAAACTACGACATTTACTAGACACGGT -5'
                                                     <<<<<<<<<<<<  ZNF-R
SlXcv-1A AA:     L   A   A   L   C   C   C   C   L   L   D   A   C   F   *
```

Part of CYSTM region of the *SlXcv-1B* gene (see SEQ ID NO: 51 for the entire sequence):

```
  2607. bp                                                                        2681.bp
    | TALEN-L >>>>>>>>>>>>>>>>  CRISPR                                               |
5'- TTTTGCAGTTTGGCTGCTGTGGCATGCTGTCTTTGAGGGTGTAAATGATCTGTGCCA -3'
              ZNF-L   >>>>>>>>>>>>
                                                     <<<<<<<<<<<<<<<<  TALEN-R2
3'- AAAACGTCAAACCGACGAGACACGACAACGACAGAGAACCTACGTACGAAAACTCCCACATTTACTAGACACGGT -5'
                                                     <<<<<<<<<<<<  ZNF-R
SlXcv-1B AA:     L   A   A   L   C   C   C   C   L   L   D   A   C   F   *
```

5B.

|  | 1 | 2 | 3 | 4 | 5 | 6 | 7 | 8 | 9 | 10 | 1 | 2 | 3 | 4 | 5 | 6 | 7 |
|---|---|---|---|---|---|---|---|---|---|---|---|---|---|---|---|---|---|
| SlXcv-1AB TALEN-L RVDs: | NG | NH | NH | HD | NG | NH | HD | NG | HD | NG | NH | NG | NH | HD | NG | NH | NG |
| Target sequence: | T | G | G | C | T | G | C | T | C | T | G | T | G | C | T | G | T |
| SlXcv-1A TALEN-R RVDs: | NG | NG | NI | HD | NI | NH | HD | NI | NG | HD | NI | NI | NI | NI | NH | HD | NI |
| Target sequence: | T | T | A | C | A | G | C | A | T | C | A | A | A | A | G | C | A |
| SlXcv-1B TALEN-R RVDs: | NG | NG | NI | HD | NI | HD | HD | HD | NG | HD | NI | NI | NI | NI | NH | HD | NI |
| Target sequence: | T | T | A | C | A | C | C | C | T | C | A | A | A | A | G | C | A |

Figure 5. TALEN, ZFN and CRISPR target sequences and RVDs specific to the genes *SlXcv-1A* and *SlXcv-1B*. 5A. Portion of the CYSTM region of genes *SlXcv-1A* and *SlXcv-1B*. The vertical lines and serial numbers above the sequences indicate the nucleotide positions according to SEQ ID NO:49 and SEQ ID NO:51. Partial amino acid sequences of proteins SlXcv-1A and SlXcv-1B are shown below the double-stranded DNA sequences. The two leucines which are missing from the mutant proteins (SlXcv-1A and SlXcv-1B) are underlined. The amino acids are indicated by the internationally accepted one-letter codes. The * indicates the stop codon. The target sequences to be recognised by the TALEN-L and TALEN-R nuclease pairs are indicated by arrow heads pointing to the right and left above the target sequences and by lines above the target sequences, and the target sequences to be recognised by the ZFN-L and ZFN-R nuclease pairs are indicated by arrow heads pointing to the right and left below the target sequences and by dotted lines below the target sequences. The arrows are in the 5'>3' direction. The sequences to be recognised by the CRISPR/Cas complex are indicated by grey background and bold letters. The six nucleotides present in the upper strand of the DNA in the mutant genes (*SlXcv-1A*, *SlXcv-1B*, *Slxcv-1A* and *Slxcv-1A*) are underlined. 5B. Amino acid doublets (RVDs) of the proteins SlXcv-1AB TALEN-L, SlXcv-1A TALEN-R1 and SlXcv-1B TALEN-R2. The numbers above the amino acid doublets of the SlXcv-1AB TALEN-L protein are the serial numbers of the RVDs.

Figure 6. Functional map of the vectors containing the TALEN pairs specific to genes *SlXcv-1A* and *SlXcv-1B*

Abbreviations: 35S pr = 35S promoter, TAL-N' = sequence of the N-terminus of the TAL effector, TAL-C' = sequence of the C-terminus of the TAL effector, NLS = Nuclear Localization Signal, SlXcv-1A_TAL-R, SlXcv-1AB_TAL-L = repeat sequences containing 17 RVDs specific to the *SlXcv-1A* gene, SlXcv-1B_TAL-R, SlXcv-1AB_TAL-L = repeat sequences containing 17 RVDs specific to the *SlXcv-1B* gene, N = Nopaline synthase polyA, pA = 35S polyA, RB = right border sequence of the t-DNA, LB = left border sequence of the t-DNA, HYG R = Hygromycin resistance gene, KAN R = Kanamycin resistance gene, B = BamHI, S = SacI, the arrows ( ----> ) indicate the direction of transcription.

**Figure 7A. Derivatives of genes *SlXcv-1A* and *SlXcv-1B* in Variant 1**

In the *Slxcv-1A* gene, the desired 6 bp deletion is formed:

```
                   2253.                    2276. 2283.                    2306. bp
                      |                        |     |                        |
wild type:

IDENTIFICATION OF A *XANTHOMONAS EUVESICATORIA* RESISTANCE GENE FROM PEPPER (*CAPSICUM ANNUUM*) AND METHOD FOR GENERATING PLANTS WITH RESISTANCE

TECHNICAL FIELD OF THE INVENTION

The present invention relates to the identification of the xcv-1 gene, which is responsible for a recessive resistance to *Xanthomonas euvesicatoria*, by genetic mapping-based cloning from *Capsicum annuum*. In addition, the invention relates to methods for generating resistant plants, in particular plants resistant to *Xanthomonas euvesicatoria*.

BACKGROUND OF THE INVENTION AND PRIOR ART

It is well-known that in arable plant production, sensitive crops are infested by various pathogens (viruses, bacteria, fungi etc.) the serious consequences of which include yield reduction or yield loss. Therefore, one fundamental requirement for advanced and competitive plant varieties is to show resistance to pests and pathogens causing major yield losses. Resistant plants allow cheaper and more environmentally friendly production because no spray liquids containing hazardous substances and toxins are released into nature. The environmentally friendly production technology of resistant plants also increases yield safety; produces of higher quality and quality can be harvested at lower costs.

Identification, isolation and characterisation of the genes providing resistance is of vital importance for both theory and practice: the process can be understood by exploring the genes involved in the infection processes, their products and the functions thereof, and this forms the indispensable basis for developing control strategies.

As regards the molecular processes of plant protection, two basic mechanisms can be distinguished. The first one is dominant resistance and the second one is recessive resistance. In case of a dominant protective mechanism, a signal molecule (typically, a protein) from the pathogen initiates a self destruction process (apoptosis) resulting in the death of the infected cells and their neighbours thereby halting the spreading of the pathogen (Pontier D. et al., C R Acad Sci III. 321:721-34, 1998.). The result of the cell destruction, i.e., programmed cell death, is a dried and discoloured necrotic patch, which is the manifestation of the so-called hypersensitive reaction (HR) (Klement Z. et al., Phytopathology 54: 474-477, 1964). Dominant resistance is race-specific and can be easily abolished as new races may break the resistance.

In case of recessive resistance, a mutation causes a loss of a function that is indispensable for the development of virulence. As yet, the steps of the development of recessive resistance, as well as the functions thereof and the plant genes of such functions are mostly unknown, however, it was found that more than one gene is involved in the development of resistance on the part of both the bacterium and plant host. Recessive resistance genes can be identified when a difference exists between the genes involved in the process induced by the pathogen and causing the disease (virulence) and the wild-type genes. Genes providing recessive resistance have been identified from a few plants, including among others the RRS1-R gene from *Arabidopsis thaliana* (Deslandes L. et al., PNAS 99: 2404-2409, 2002) and a gene against *Xanthomonas oryzae* from rice (Iyer-Pacuzzi A. S., Pathosystem. Mol. Plant Microb. Interaction 20:731-739, 2007). A number of genes providing dominant resistance have been identified from pepper on the basis of mutant phenotypes, but no genes providing recessive resistance. In general, recessive resistance is not race-specific and is more difficult; therefore, it is more stable.

In the field growing of edible and spice pepper, the bacterium *Xanthomonas campestris* pv. *vesicatoria* (Xcv), recently renamed as *Xanthomonas euvesicatoria* (Xe) causes the most significant damage (Jones J. B. et al., System. Appl. Microbiol. 27: 755-762, 2004). The Xe bacterium is mediated mostly by water and enters the plant through wounds and leaf gaps. Under warm and moist climatic conditions, the bacterium spreads rapidly. The symptoms of the disease mostly appear on the leaves. Scar-like patches develop on the back of the leaves and later become necrotic areas on the face of the leaves. The infected leaves of sensitive plants die and fall off within one to two weeks, and the yield is burnt by the sun.

Similar to a group of plant and animal bacteria, *Xanthomonas euvesicatoria* is also capable of growing so-called pili through the Type Three Secretion System (TTSS), and the ends of these pili extend until the eukaryotic cell membrane. The pilus is permeable for the effector molecules of the bacterium. One or more of the effector molecules create a so-called translocon in the cell membrane through which the effector molecules enter the eukaryotic cytoplasm; in several cases, they also enter the nucleus from the cytoplasm if they comprise a Nuclear Localization Signal (NLS). For their growth, the bacteria use the nutrient molecules present in the plant cells, which are released upon the loss of integrity of the plant cells. Disintegration of the cells is induced by the effector molecules introduced through the Type Three Secretion System of Xe via an infection mechanism the details of which are yet unclear. The proliferation of the bacteria damages plant tissue to such an extent as to cause the majority of the leaves to fall off and the plant to dry out sooner or later.

The complete genome of *Xanthomonas euvesicatoria* (*X. campestris* pv. *vesicatoria* strain 85-10) has been determined (Thieme F. et al., J. Bacteriol. 187:7254-7266, 2005), and the genes of the effector proteins involved in the induction of a dominant hypersensitive reaction from pepper have been identified. Genes for recessive resistance to *Xanthomonas euvesicatoria* have not been identified from pepper yet.

The literature describes a few pepper varieties resistant to Xe. These plants carry resistance genes including but not limited to Bs1 (Cook A. A. and Stall R. E., Plant Dis. 53:1060-1062, 1963), Bs2 (Cook A. A. and Guevara Y. G., Plant Dis. 68:329-330, 1984), Bs3 (Kim B. S. and Hartmann R. W., Plant Dis. 69:233-235, 1985), Bs4 (Hibberd et al., Phytopathology 77:1304-1307, 1987), bs5 (Jones J. B. et al., System. Appl. Microbiol. 27:755-762, 2004) and bs6 (Vallejos C. E. et al., Theor. Appl. Genet. 121:37-46, 2010). The latter two—bs5 and bs6—are recessive types of resistance genes.

Despite the existing resistant pepper varieties, there is still an extreme need for pepper varieties resistant to *Xanthomonas* species and for other plant varieties that are resistant to biotic or abiotic factors.

The objective of the present study is to identify and isolate a gene from pepper (*Capsicum annuum*) providing recessive resistance to *Xanthomonas euvesicatoria*, which can be used to develop single or double (pyramided) resistance varieties—mostly to *Xanthomonas* sp., but presumably to other biotic or abiotic factors as well—in sensitive pepper species and other plant species such as tomato, potato, rice, citruses, banana, etc.

SUMMARY OF THE INVENTION

The above objective could be achieved by the present invention. From a *Capsicum annuum* carrying a recessive resistance, a gene designated as xcv-1 was isolated using genetic map-based cloning. The sequence of the isolated gene was determined (SEQ ID NO:37) and it was found that the xcv-1 protein (SEQ ID NO:38) encoded by the gene comprises a double Leu deletion at the locations corresponding to positions 87 and 88 of the wild-type Xcv-1 protein (SEQ ID NO:42). The mutant xcv-1 protein is a tail-anchored (TA) transmembrane (TM) protein, more specifically a CYSTM protein, which carries the double leucine deletion in its cysteine-rich transmembrane region (hereinafter referred to as 'CYSTM region'). This CYSTM region shows structural relatedness to the CYSTM region of other known transmembrane proteins (Venancio T. M. and Aravind L., Bioinformatics 26:149-152, 2010) in that it is a common feature that they are rich in cysteine (comprising at least 3 cysteines), that they are bordered by an amino acid with negative charge (aspartic acid or glutamic acid) or a polar amino acid (asparagine) in position 4 from the C-terminus of the protein, and that the Asp, Glu or Asn is preceded by two hydrophobic amino acids (here: leucine), and less frequently, these positions contain isoleucine, methionine, tryptophan, glycine, alanine, threonine, phenylalanine, valine and cysteine.

It is interesting to note that certain fungi (e.g., *Schizosaccharomyces pombe, Saccharomyces cerevisiae*) which are resistant to certain abiotic factors such as UV radiation, and certain drugs (e.g., canavanine), lose such resistance and their sporulation capacity if a CYSTM-type protein loses function as a result of a gene mutation (Lee J. K. et al., Biochem. Biophys, Res. Comm. 202:1113-1119, 1994; Lee, J. K. et al., Mol. Gen. Genet. 246:663-670, 1995; Venancio T. M. et al., Mol Biosyst. 6:175-181, 2010; Venancio, T. M. and Aravind, L. Bioinformatics 26:149-152, 2010). Similar to fungi, *Arabidopsis thaliana* plants also suffer severe disturbances in megasporogenesis in case of a loss of function in its genes homologous to the above CYSTM proteins (WIH1, WIH2 double mutation) (Lieber, D. et al., Current Biology 21:1009-1017, 2011).

It was found that by removing two amino acids from the C-terminal CYSTM region—preferably those in positions 5 and 6 from the C-terminus—of a protein homologous to the wild-type Xcv-1 protein but derived from a plant organism other than pepper (for example, tomato), advantageous properties, primarily recessive resistance can be induced in the plant organism. The deletion of the two codons, i.e., 6 base pairs, encoding these two amino acids in the CYSTM region—which include but is not limited to leucine, isoleucine, methionine, tryptophan and cysteine—is referred to as 'the desired 6-bp deletion'.

Without being limited to any theory regarding the development of resistance, it is likely that a double Leu deletion in the CYSTM region (the last 13 amino acids in the C-terminus of the protein) of the mutant xcv-1 protein encoded by the xcv-1 gene prevents or reduces the entry of the effector molecules of bacteria with type three secretion system into plant cells. This hypothesis is preliminarily substantiated by the result of double resistant papper lines carrying Bs2 and xcv-1 in homozygous configuration. These plants upon infection with AvrBs2 containing Xe do not show the HR phenotype characteristic of AvrBs2 effector of the infecting Xe most probably because AvrBs2 is not entering the plant cells, on the other hand the phenotype of this infection very similar to that caused by the xcv-1/xcv-1 containing plants. The above result indicate that xcv-1 is epistatic over Bs2.

The identification and characterization of the xcv1 bacterial spot disease resistance has revealed that this gene contains a six nucleotide in-frame deletion that removes two leucine amino acids from the carboxy terminal portion of the protein. Computational analyses suggest that this protein is a membrane protein with an unknown function. Since this mutation confers resistance to several strains of *Xanthomonas* that cause disease on pepper and tomato, it would be informative to test whether this mutation affects the type three secretion delivery of type three effector proteins into plant cells. One could use a reporter gene assay to examine the biochemical activity of translational fusion proteins between the N-terminal domains of various type three effector proteins and the reporter gene adenylate cyclase (Direct biochemical evidence for type III secretion-dependent translocation of the AvrBs2 effector protein into plant cells. Casper-Lindley C. et al., PNAS 99:8336-8341, 2002). Using this assay, xcv-1 and other plants, including wild-type peppers, tomato, citrus, walnut, lettuce, brassica, soybean, bean, rice, etc., can be tested for their ability to receive type three secreted effector proteins from strains of *Xanthomonas euvesicatoria, X. perforans, X. gardneri* and other type-three secretion system dependent bacteria. The adenylate cyclase assay will allow a means of monitoring the mechanism of resistance in xcv-1 plants or with combinations of resistance genes.

Accordingly, it was assumed that a transgenic plant having recessive resistance can be generated by the removal of the gene encoding the original CYSTM region through knocking out homologous resident genes of a plant, and by the simultaneous replacement with a mutant CYSTM region comprising a desired 6-bp deletion through transformation. Similarly, it is assumed that if a derivative or derivatives carrying the desired 6-bp deletion is/are generated in a plant by spontaneous or induced mutation of the gene segment encoding the CYSTM region of solitary (one-copy) or multiple-copy (double-, triple-copy etc.) CYSTM proteins, or by nuclease-based "genome editing" methods such as, for example, Zinc Finger Nuclease (ZFN), Transcription Activator-Like Effector Nuclease (TALEN) and Clustered Regularly Interspaced Short Palindromic Repeats/CRISPR-associated nuclease technique—or CRISPR/Cas nuclease technique in short—, or in any other ways, then plants with recessive resistance may be generated. Presumably, the mutant homologues will show an advantageous property, i.e., will render the plant resistant.

This hypothesis was proven by transgenic technique using Xe-sensitive tomato (*Solanum lycopersicum*) as follows: recessive resistance to Xe was generated in tomato by inactivating two resident genes (SlXcv-1A, SEQ ID NO:49 and SlXcv-1B, SEQ ID NO:51) homologous to the wild-type Xcv-1 gene and by creating in vitro the 6-bp deletions in the homologous genes at the positions corresponding to the xcv-1 gene (Slxcv-1A, SEQ ID NO:59 and Slxcv-1B, SEQ ID NO:66), followed by the introduction of the mutant genes into the plant cells.

Additionally, without limiting the scope of the invention, three methods using genome editing techniques (TALEN, CRISPR/Cas nuclease and ZFN) are described for creating the desired 6-bp deletion and thereby generating recessive resistance to *Xanthomonas* species in tomato.

Slxcv-1A and Slxcv-1B, the mutant genes responsible for the resistance, could be isolated from the transgenic tomato plants, their sequences were determined (SEQ ID NO:59 and SEQ ID NO:66, respectively), and they encode proteins Slxcv-1A and Slxcv-1B (SEQ ID NO:60 and SEQ ID NO:67, respectively). The sequences of the latter were compared to the wild-type protein sequences (SEQ ID NO:50 and SEQ ID NO:52), and the deletions were confirmed at the locations corresponding to positions 86 to 87 and 88 to 89.

Accordingly, one object of the present invention is the xcv-1 gene isolated from *Capsicum annuum*, which is responsible for a recessive resistance to *Xanthomonas euvesicatoria* and has the nucleotide sequence of SEQ ID NO:37. The present invention also relates to the cDNA of the xcv-1 gene, which has the nucleotide sequence of SEQ ID NO:90.

Another object of the present invention is the xcv-1 CYSTM protein providing the resistance, which is encoded by the xcv-1 gene and its cDNA sequence, and has the amino acid sequence of SEQ ID NO:38, wherein the CYSTM region of the protein carries a double Leu deletion at the locations corresponding to positions 87 and 88 of the wild-type protein of SEQ ID NO:42.

Another object of the present invention is a protein homologous to the xcv-1 CYSTM protein, which comprises a deletion of two amino acids in the CYSTM region in comparison with the CYSTM region of the wild-type homologous protein, and provides resistance. Preferably, the mutant homologous protein carries the deletion of two amino acids in the CYSTM region, at positions 5 and 6 from the C-terminus of the wild-type protein. Preferred examples of such mutant proteins include proteins Slxcv-1A or Slxcv-1B, which have the amino acid sequences of SEQ ID NO:60 or SEQ ID NO:67, respectively.

In addition, the invention relates to the homologues of the xcv-1 gene encoding the above homologous mutant CYSTM proteins. Preferred examples include the Slxcv-1A gene having the nucleotide sequence of SEQ ID NO:59 or its cDNA variant having the nucleotide sequence of SEQ ID NO:88, which encode the Slxcv-1A mutant homologous protein (SEQ ID NO:60), or the Slxcv-1B gene having the nucleotide sequence of SEQ ID NO:66 or its cDNA variant having the nucleotide sequence of SEQ ID NO:89, which encode the Slxcv-1B mutant protein (SEQ ID NO:67).

Furthermore, the present invention relates to engineered nuclease proteins specific to the DNA sequence of a gene homologous to the wild-type Xcv-1 gene (SEQ ID NO:41), which selectively recognise the DNA segment encoding the CYSTM region of the gene homologous to the wild-type Xcv-1 gene, or certain partial sequences thereof. Preferred engineered nuclease proteins include those specific to the DNA sequences of genes SlXcv-1A and SlXcv-1B. Additional preferred engineered nuclease proteins include a ZFN nuclease pair selectively recognising the gene segments represented by SEQ ID NO:86 and 87, or a TALEN nuclease pair selectively recognising the gene segments represented by SEQ ID NO:78 and 79 or 78 and 80, or a sgRNS-CRISPR/Cas nuclease selectively recognising the gene segments represented by SEQ ID NO:81.

The present invention also relates to the genes encoding said engineered nuclease proteins.

The present invention also relates to artificial nucleic acid molecules (amiRNA) for the silencing the SlXcv-1A and SlXcv-1B which are complementer to the CYSTM region of the mRNA of the plant cells. These nucleic acid molecules comprises additional nucleotide sequences for expression. Important to note, that these nucleic acid molecules do not silence those genes carrying the desired 6 bp deletion.

Another object of the present invention is a vector comprising the xcv-1 gene (SEQ ID NO:37), one or more homologues thereof, preferably genes Slxcv-1A (SEQ ID NO:59) and/or Slxcv-1B (SEQ ID NO:66), or the genes of the TALEN, CRISPR/Cas and ZFN nucleases specific to the Xcv-1 genes suitable for genome editing and other nucleic acid molecules described in this invention.

Another object of the invention is a host cell transformed with said vector.

Another object of the present invention is a method for the in vitro preparation of a mutant gene homologous to the xcv-1 gene or its cDNA variant, comprising the steps of: a) identifying a gene homologous to the wild-type Xcv-1 gene (SEQ ID NO:41) in a plant; b) preparing in vitro the genomic and cDNA sequences of the gene identified in step a) in the form of a DNA; and c) creating in vitro a deletion of the desired 6 bp in the DNA prepared in step b) in the portion of the gene encoding the CYSTM region. Using the method of the invention, the 6-bp deletion is preferably created in those nucleotides of the CYSTM region of the gene that encode the 5th and 6th amino acids from the C-terminus.

The present invention also relates to mutant plants showing resistance to a biotic or abiotic factor, the genomes of which are modified to contain a 6-bp deletion in the segment encoding the CYSTM region of one or more genes homologous to the wild-type Xcv-1 gene (SEQ ID NO:41) or its cDNA sequence (SEQ ID NO:91).

Another object of the present invention is a method for generating a transgenic plant resistant to biotic or abiotic factors by transformation, comprising the steps of: a) transforming the cells of a sensitive plant by one or more mutant genes homologous to the xcv-1 gene of the invention in a manner ensuring the functional expression thereof, b) inactivating one or more resident genes homologous to the wild-type Xcv-1 gene, or the mRNA or protein product thereof, in the sensitive transformant plant cells obtained in step a); and c) regenerating the plant from the transformants and selecting the resistant individuals.

Another object of the invention is a method based on genome editing, which comprises a step of creating the desired 6-bp deletion in the wild-type homologous gene using ZFN, TALEN or CRISPR/Cas nucleases specific to the sequence of the wild-type Xcv-1 gene.

Yet another object of the invention is a method based on genome editing, in which the ZFN and TALEN nuclease proteins recognising the DNA sequences homologous and specific to the Xcv-1 gene are introduced into plant-derived host cells using bacteria having type three secretion system but not causing diseases (non-pathogenic bacteria) (see e.g., WO/2005/085417).

Yet another object of the present invention is a plant and its progeny resistant to biotic or abiotic factors, which can be generated by the methods of the invention and carries a deletion of two amino acids in the CYSTM region of one or more of its transmembrane proteins in comparison with the wild-type protein. Preferably, the plant is a tomato plant (*Solanum lycopersium*), in which recessive resistance to *Xanthomonas euvesicatoria* has been created.

Furthermore, the invention relates to a method to generate resistant plant by combining (pyramiding) at least two resistance genes against the same pathogen (e.g. *Xanthomonas* sp.). Accordingly, the present invention relates to a tomato plant containing more than one resistance genes conferring resistance against *Xanthomonas euvesicatoria* which is generated by one of the procedures described in the invention of which one resistance gene is based on the creation of the desired 6 bp deletion in a gene homologues to xcv-1 and the other resistance gene or genes is/are including but not limited to e.g. Bs2, Bs2, Bs3, Bs4, bs5, bs6 or their combination.

The present invention also relates to a rice plant containing more than one resistance genes conferring resistance against *Xanthomonas oryzae* pv. *oryzae* which is generated by one of the procedures described in the invention where said rice plant carries in combination another resistance gene or genes against *Xanthomonas oryzae* pv. *oryzae* which is/are including but not limited to e.g. Xa-4+xa-5+Xa-7+xa-13+Xa-21 genes.

The present invention also relates to a citrus plant containing more than one resistance genes conferring resistance against *Xanthomonas citri* pv. *citri, Xanthomonas axonopodis* pv. *citri* which is generated by one of the procedures described in the invention where said citrus plant carries in combination another resistance gene or genes against *Xanthomonas citri, Xanthomonas axonopodis* strains.

Furthermore, the invention relates to antibodies against the proteins of the invention, which are specific to the mutant CYSTM region of the proteins and bind to the resistant mutant protein but not to the wild-type protein, and are useful as probes in in vitro methods for determining whether a plant carries such resistant mutant proteins or not.

The present invention also relates to genetic probes, which are specific to the mutant region of the xcv-1 gene and of its homologues, and are useful for the identification of resistance genes in an in vitro method.

DESCRIPTION OF THE FIGURES

FIG. 1: The xcv contig physically covering the xcv-1 gene with overlapping BAC clones. Scheme of the identified and overlapping BAC clones (horizontal lines). The numbering of the BAC clones is indicated above the lines. The two ends of the BAC clones are indicated by "−40" and "op", respectively. The initial marker is indicated by an arrow.

FIG. 2: Hydrophobicity curve of the Xcv-1 protein. The part above the line marked by "0" is that part of the protein which is presumably localised in the membrane. TM=transmembrane, DAS: "Dense Alignment Surface" algorithm.

FIG. 3: The point of attack (middle line; SEQ ID NO:127) of the target mRNA (SlXcv1A1/SlXcv1B genes), the amino acid sequence deducible from that (upper line; SEQ ID NO:126), and the designed 21-bp SlXe1-amiRNA sequence (lower line; SEQ ID NO:128).

FIG. 4: "Northern" autoradiogram of the RNA hybridisation of the SlXe1-amiRNA. The Northern blot of the maturing SlXe1-amiRNAs of various lengths (21, 22 and 24 bp) was hybridised to an alpha-$^{32}$ATP-labelled probe encoding the SlXe1-amiRNA. Samples: 1.=RNA sample prepared from a control (untransformed) plant, 2-3. RNA sample prepared from a plant containing the SlXe1-amiRNA expression construct, M.=smallRNA molecular weight marker (20 bp, 21 bp, 30 bp).

FIGS. 5A-5B. TALEN, ZFN and CRISPR target sequences and RVDs specific to the genes SlXcv-1A and SlXcv-1B. 5A. FIG. 5A. Portion of the CYSTM region of genes SlXcv-1A (upper strand, SEQ ID NO:130; lower strand, SEQ ID NO:131) and SlXcv-1B (upper strand, SEQ ID NO:133; lower strand, SEQ ID NO:134). The vertical lines and serial numbers above the sequences indicate the nucleotide positions according to SEQ ID NO:49 and SEQ ID NO:51. Partial amino acid sequences of proteins SlXcv-1A (SEQ ID NO:132) and SlXcv-1B (SEQ ID NO:135) are shown below the double-stranded DNA sequences. The two leucines which are missing from the mutant proteins (SlXcv-1A and SlXcv-1B) are underlined. The amino acids are indicated by the internationally accepted one-letter codes. The * indicates the stop codon. FIG. 5B. The target sequences to be recognised by the TALEN-L and TALEN-R nuclease pairs are indicated by arrow heads pointing to the right and left above the target sequences and by lines above the target sequences, and the target sequences to be recognised by the ZFN-L and ZFN-R nuclease pairs are indicated by arrow heads pointing to the right and left below the target sequences and by dotted lines below the target sequences. The arrows are in the 5'>3' direction. The sequences to be recognised by the CRISPR/Cas complex are indicated by grey background and bold letters. The six nucleotides present in the upper strand of the DNA in the mutant genes (SlXcv-1A, SlXcv-1B, Slxcv-1A and Slxcv-1A) are underlined. In FIG. 5B, the amino, acid doublets (RVDs) of the proteins SlXcv-1AB TALEN-L, SlXcv-1A TALEN-R1 and SlXcv-1B TALEN-R2 and their corresponding target sequences (SEQ ID NOS:136-138, respectively) are shown. The numbers above the amino acid doublets of the SlXcv-1AB TALEN-L protein are the serial numbers of the RVDs.

FIG. 6. Functional map of the vectors containing the TALEN pairs specific to genes SlXcv-1A and SlXcv-1B. Abbreviations: 35S pr=35S promoter, TAL-N'=sequence of the N-terminus of the TAL effector, TAL-C'=sequence of the C-terminus of the TAL effector, NLS=Nuclear Localization Signal, SlXcv-1A_TAL-R, SlXcv-1AB_TAL-L=repeat sequences containing 17 RVDs specific to the SlXcv-1A gene, SlXcv-1B_TAL-R, SlXcv-1AB_TAL-L=repeat sequences containing 17 RVDs specific to the SlXcv-1B gene, N=Nopaline synthase polyA, pA=35S polyA, RB=right border sequence of the t-DNA, LB=left border sequence of the t-DNA, HYG R=Hygromycin resistance gene, KAN R=Kanamycin resistance gene, B=BamHI, S=SacI, the arrows (→) indicate the direction of transcription.

FIGS. 7A-7C. Possible variants of genes SlXcv-1A and SlXcv-1B in TALEN-treated plants. FIG. 7A shows a portion of the wild-type nucleotide sequence of SlXcv-1A, Variant 1, and the amino acid sequences encoded by Variant 1 (SEQ ID NOS:139-141; respectively) and a portion of the wild-type nucleotide sequence of SlXcv-1A, Variant 1, and the amino acid sequences encoded by Variant 1 (SEQ ID NOS:142-144; respectively). FIG. 7B shows a portion of the wild-type nucleotide sequence of SlXcv-1B, Variant 2, and the amino acid sequences encoded by Variant 2 (SEQ ID NOS:145-147; respectively). FIG. 7B shows a portion of the wild-type nucleotide sequence of SlXcv-1A, Variant 3, and the amino acid sequences encoded by Variant 3 (SEQ ID NOS:148-150; respectively).

DETAILED DESCRIPTION OF THE INVENTION

Definitions

As used herein, the term "resistance to biotic or abiotic factors" means that the plant is resistant to various biotic factors such as plant-pathogenic bacteria, fungi and viruses, or abiotic factors such as salt stress, drought stress etc.

As used herein, the term "recessive resistance to *Xanthomonas* sp." means that the plant is resistant to at least one *Xanthomonas* species including, but not limited to, *Xanthomonas euvesicatoria, Xanthomonas gardneri, Xanthomonas perforans, Xanthomonas oryzae* pv. *oryzae,*

*Xanthomonas citri* pv. *citri*, *Xanthomonas axonopodis* pv. *citri*, *Xanthomonas campestris* pv. *musacearum*. In a preferred embodiment of the invention, the plant is resistant to at least *Xanthomonas euvesicatoria*. In some embodiments of the invention, the plant is resistant to two, three, four, or more *Xanthomonas* species and preferably, one of the species is *Xanthomonas euvesicatoria*.

As used herein, the term "plant" means an organism capable of photosynthesising, the parts of which, e.g., root, stem, leaf, flower, fruit etc., the progeny of which after sexual reproduction, e.g., F1, F2, F3 etc. generation after crossing or self-pollination, and progeny after vegetative reproduction, e.g., cloning from root cuttings or stem cuttings, grafting, budding, micropropagation, etc.

As used herein, the term "resident gene" means genes naturally occurring in living organisms not engineered by humans.

As used herein a "tail-anchored protein" (TA protein) refers to a protein the $NH_2$-terminal portion (domain) of which is anchored to the double phospholipid membrane through a single hydrophobic portion located near to its COOH-terminus, as described by Borgese N. et al. (J. Cell Biol. 161: 1013-1019, 2003).

As used herein, the term "transmembrane" (TM in short) means a hydrophobic protein portion spanning the double phospholipid membrane.

As used herein, the term "transmembrane protein" (TM protein) means a protein comprising a transmembrane protein domain.

As used herein, the term "CYSTM protein" means a TA protein having a cysteine-rich TM region close to the COOH-terminus (CYSTM region) in the sense described by Venancio T. M. and Aravind L. (Bioinformatics 26:149-152, 2010).

As used herein, the term "CYSTM region" in relation to proteins means a cysteine-rich TM protein segment in the sense described by Venancio T. M. and Aravind L. (Bioinformatics 26:149-152, 2010).

As used herein, the term "homologous" refers to the situation where nucleic acid or protein sequences are similar because they have a common evolutionary origin.

As used herein, the term "proteins homologous to the wild-type Xcv-1 protein" refers to CYSTM proteins in the sense described by Venancio T. M. and Aravind L. (Bioinformatics 26:149-152, 2010).

As used herein, the term "proteins homologous to the mutant xcv-1 protein" means CYSTM protein variants in which the CYSTM region contains a deletion of 2 amino acids compared to its wild type protein and which provide resistance.

As used herein, the term "genes homologous to the Xcv-1 gene" means gene variants or its cDNA sequence without intron(s) encoding the above "proteins homologous to the Xcv-1 protein".

As used herein, the term "genes homologous to the xcv-1 gene" means gene variants or its cDNA sequence without intron(s) encoding the above "proteins homologous to the xcv-1 protein".

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the full-length or native protein and hence retain the ability to initiate in a plant a hypersensitive response in the presence of a effector protein from a plant pathogen. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

Polynucleotides that are fragments of a native polynucleotide of the present invention comprise at least 16, 20, 50, 75, 100, 125, 150, 175, 200, 250, 300, 350, 400, 450, 500, 550, 600, 650, 700, 800, 900, 1000, 1100, 1200, 1300, 1400, 1500, 2000, 2500, 3000, or 3500 contiguous nucleotides, or up to the number of nucleotides present in a full-length polynucleotide disclosed herein (for example, 3859 nucleotides for SEQ ID NOS: 79, 80 and 81, respectively).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polynucleotides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a polynucleotide of the invention or can be used in decreasing the level of Xcv-1 or a protein homologous to Xcv-1 in a plant by the methods disclosed herein. Variant polynucleotides further include homologous polynucleotides isolated from other species. Generally, variants of a particular polynucleotide of the invention (for example, SEQ ID NO:37 or 39 or 41 or 49 or 51 or 59 or 66 or 69 or 72 or 73 or 74 or 75 or 76 or 77 or 78 or 79 or 80 or 81 or 86 or 87 or 88 or 89 or 90 or 92), will have at least about 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptide of SEQ ID NO: 38 or 40 or 42 or 50 or 52 or 60 or 67 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Such variants also include homologous proteins in other species. Biologically active variants of a protein of the present invention will have at least about 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. Such biologically active variants include, for example, wild-type Xcv-1 and homologous proteins as well as mutant versions thereof (e.g. xcv-1) that confer to a plant resistance to at least one plant pathogenic *Xanthomonas* species. A biologically active variant of a protein of the invention may differ from that protein by as few as 1-15 amino acid residues, as few as 1-10, such as 6-10, as few as 5, as few as 4, 3, 2, or even 1 amino acid residue.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire (i.e full-length) sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers, E. W. and Miller, W. CABIOS 4:11-17, 1988; the local alignment algorithm of Smith, T. F. et al., Adv. Appl. Math. 2:482, 1981; the global alignment algorithm of Needleman, S. B. and Wunsch, C. D. J. Mol. Biol. 48:443-453, 1970; the search-for-local alignment method of Pearson, W. R. and Lipman, D. J. Proc. Natl. Acad. Sci. 85:2444-2448, 1988; the algorithm of Karlin, S. and Altschul, S. F. Proc. Natl. Acad. Sci. USA 872264, 1990, modified as in Karlin, S. and Altschul, S. F. Proc. Natl. Acad. Sci. USA 90:5873-5877, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al., Gene 73:237-244, 1988; Higgins, D. G. et al., CABIOS 5:151-153, 1989; Corpet, F. et al., Nucleic Acids Res. 16:10881-90, 1988; Huang, X. et al., CABIOS 8:155-65, 1992; and Pearson, W. R. et al., Meth. Mol. Biol. 24:307-331, 1994. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul, S. F. et al., J. Mol. Biol. 215:403, 1990 are based on the algorithm of Karlin, S. and Altschul, S. F. (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, S. F. et al., Nucleic Acids Res. 25:3389, 1997. Alternatively, PSI-BLAST (in BLAST 2.0) can be used to perform an iterated search that detects distant relationships between molecules. See Altschul, S. F. et al., (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman, S. B. and Wunsch, C. D. *J. Mol. Biol.* 48:443-453, 1970 to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff, S. and Henikoff, J. G. *Proc. Natl. Acad. Sci. USA* 89:10915, 1989).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, the term "CYSTM region" in relation to nucleic acids (DNA, RNA) is a nucleotide segment extending to 52 and 52 nucleotides into both (5' and 3') directions, respectively, from the 2nd nucleotide of the stop codon of the "genes homologous to the Xcv-1 gene" or "genes homologous to the xcv-1 gene".

As used herein, the term "the desired 6-bp deletion" means a deletion of 6 base pairs in the DNA segment encoding the CYSTM region of genes homologous to the Xcv-1 gene, which results in resistance.

As used herein, the term "6 nucleotides to be deleted from the wild-type gene and the surrounding nucleotides" means a nucleotide segment extending 52 and 52 nucleotides into both directions from the 6-bp deletion created in the CYSTM region. The 6-bp deletion is created anywhere in the CYSTM region of the gene or in those nucleotides that encode the 5th and 6th amino acid from the C-terminus.

As used herein, the term "Type Three Secretion System" (TTSS in short) is a system by which certain pathogenic bacteria (e.g., *Xanthomonas* sp., *Pseudomonas* sp., *Erwinia* sp., *Ralstonia* sp., *Escherichia* sp., *Yersinia* sp. etc.) introduce effector molecules through the TTSS-specific pili into eukaryotic host organisms as described by Galan J. E. et al. (Nature 444:567-573, 2006).

As used herein, the term "genome editing" means a method in which a engineered nuclease or engineered nuclease pair performs double-strand breaks (DSB) in a predetermined specific DNA segment in which a DNA repair mechanism referred to as Non-homologous End Joining (NHEJ) creates short deletions or insertions as described by Gaj T. et al. (Trends Biotechnol. 31:397-405, 2013).

As used herein the term "Double Stranded Break" (DSB in short) means that a DNA sequence is cleaved by a specific nuclease or nuclease pair at both DNA-strands like a molecular pair of scissors. Nucleases performing double stranded breaks of the DNA include, among others, ZFN, TALEN and CRISPR/Cas.

As used herein, the term "Non-homologous End Joining" (NHEJ) means a method in which the DNA repair mechanism of the cells joins (ligates) two double-stranded DNA ends.

As used herein, the term "ZFN" means an artificial engineered nuclease recognising DNA sequences and cleaving both strands thereof (see below).

As used herein, the term "TALEN" means an artificial engineered nuclease recognising DNA sequences and cleaving both strands thereof (see below).

As used herein, "CRISPR/Cas" recognises complementary DNA sequences and cleaves both strands thereof with the help of the sgRNA and the Cas nuclease (see below).

As used herein, the term "an artificial nucleic acid molecule" is a non-naturally occurring nucleic acid molecule.

As used herein, the term "a gene" is a nucleotide sequence which comprises of promoter, exon(s), intron(s) in addition to 5'- and 3'-untranslated regions.

As used herein, the term "cDNA" is a nucleotide sequence of the copy of the mRNA of a gene.

As used herein, the term "an artificial nuclease" is an engineered nuclease.

As used herein, the term "engineered nucleases" are artificial restriction enzymes that can be programmed to cut a pre-determined nucleic acid sequence.

The Zinc Finger Nuclease (ZFN in short) is a fusion protein consisting of the part of the FokI restriction endonuclease protein responsible for DNA cleavage and a zinc finger protein which recognises specific, designed genomic sequences and cleaves the double-stranded DNS at those sequences, thereby producing free DNA ends (Urnov F. D. et al., Nat Rev Genet. 11:636-46, 2010; Carroll D., Genetics. 188:773-82, 2011).

The Transcription Activator-Like Effector Nuclease (TALEN in short) is a fusion protein consisting of the part of the FokI restriction endonuclease protein responsible for DNA cleavage, the part of the transcription activator-like effector (TALE) protein responsible for DNA binding, and an amino acid segment responsible for transfer into the nucleus (Nuclear Localization Signal, NLS in short). The DNA binding portion of the protein can be designed to be sequence-specific (Christian M. et al., Genetics 189:757-761, 2010; Mussolino C. et al., Nucleic Acids Res. 39:9283-9293, 2011; Miller J. C. et al., Nat. Biotechnol. 29:143-148, 2011; Cermak T. et al., Nucl. Acids Res. 39:e 82, 2011).

The Clustered Regularly Interspaced Short Palindromic Repeats/CRISPR-associated nuclease (CRISPR/Cas in short) is an RNA-guided (simple guide RNA, sgRNA in short) DNA endonuclease system performing sequence-specific double-stranded breaks in a DNA segment homologous to the designed RNA. It is possible to design the specificity of the sequence (Cho S. W. et al., Nat. Biotechnol. 31:230-232, 2013; Cong L. et al., Science 339:819-823, 2013; Mali P. et al., Science 339:823-826, 2013; Feng Z. et al., Cell Research: 1-4, 2013).

One advantage of the above techniques is that the transgenes containing the TALEN or ZFN or CRISPR/Cas nuclease can be removed from the progeny of the Xe resistant plant by genetic segregation, that is, non-transgenic plants can be generated from them.

The mutant variants of the CYSTM region of the xcv-1 protein can be designed using computer programmes, and common features of them include their localisation at the C-terminus of the protein, the presence of at least 2 cysteines generally followed by an aspartic acid (D), glutamic acid (E) or asparagine (N) residue, and they are represented by the following sequences:

```
CXXXXCCCCD, XXXXXCCCCD, CXXXXXCCCD, CXXXXCXCCD,

CXXXXCCXCD, CXXXXCCCXD, XXXXXCCCCD, XXXXXCXCCD

CXXXXXXCCD, CXXXXCXCXD, CXXXXCCXXD, CXXXXCCCCE,

XXXXXCCCCE, CXXXXXCCCE, CXXXXCXCCE, CXXXXCCXCE,

CXXXXCCCXE, XXXXXXCCCE, XXXXXCXCCE, CXXXXXXCCE,

CXXXXCXCXE, CXXXXCCXXE, CXXXXCCCCN, XXXXXCCCCN,

CXXXXXCCCN, CXXXXCXCCN, CXXXXCCXCN, CXXXXCCCXN,

XXXXXXCCCN, XXXXXCXCCN, CXXXXCXCCN, CXXXXCXCXN, and

CXXXXCCXXN (SEQ ID NOS: 93-125, respectively).
``` wherein D=aspartic acid, E=glutamic acid, N=asparagine, X=an amino acid residue compatible with the transmembrane character, mostly a hydrophobic or non-polar amino acid residue, e.g., glycine (G), cysteine (C), leucine (L), isoleucine (I), alanine (A), tryptophan (W), threonine (T), methionine (M), phenylalanine (F) or valine (V).

The xcv-1 gene providing recessive resistance was isolated from pepper using *Capsicum annuum* Gene Bank Accession No. PI163192. The isolation of the xcv-1 gene enables the designing of genetic markers using the sequence information of the gene and the linked DNA region, and the facilitation of traditional pepper breeding using these markers for Marker Assisted Selection, as well as the generation of resistant pepper and other plant varieties based on the sequence information of the gene by biotechnological methods involving the targeted modification or transforming the cells with a xcv-1 homologues gene prior to knocking-out the resident gene.

According to the invention, the xcv-1 gene was isolated from *Capsicum annuum* using the following method.

1. Genetic Mapping of the Xcv-1 Gene in Pepper 1.1. Generation of the F2 Segregating Population For the mapping, a new population was created by intraspecies crossing (*Capsicum annuum* x *Capsicum annuum*) followed by the self-pollination of the F1 plants. For the crossing, Feherozon (FO), a commercially available Hungarian cultivated variety sensitive to *Xanthomonas* was used as the father parent and an Xe-resistant plant, Gene Bank Accession No. PI163192 (T1), was used as the mother parent. After the crossing, 45 seeds from the fruit of one of the mother plants were sown and the hybrid character of the resulting plants was confirmed by appropriate molecular DNA markers. Next, the 45 F1 individuals were grown, and the F2 seeds from the self-pollination were collected. The F2 individuals from the self-pollination of the F1 individuals were then used for the genetic mapping of the xcv-1 gene. The objective was to grow as many F2 individuals as possible to allow for the identification of individuals carrying recombination events as close to the xcv-1 gene as possible, and thereby for the narrowing of the genetic and—at the same time—the physical region comprising the xcv-1 gene. Until the identification of the xcv-1 gene, more than 3000 F2 individuals were generated, grown and subjected to xcv-1 phenotyping.

1.2. *Xanthomonas* Resistance Test

Phenotyping the segregating individuals as sensitive or resistant to *Xanthomonas* is indispensable and of key importance for localising the xcv-1 gene on the genetic map. An incorrect phenotyping makes genetic mapping impossible or extremely difficult. As a result of the biological tests, finally 765 and 2354 F2 plants proved to be resistant and sensitive, respectively.

1.3. Mapping of the Xcv-1 Locus

On the basis of the available genotypes and xcv-1 phenotypes, the locus of the xcv-1 gene was mapped to the third chromosome of pepper. For this, sequences available in gene banks or markers used by others were applied for the mapping of the xcv-1 gene. Specific primer pairs were designed, and the primer pairs were used for PCR amplification; the map location of the markers were determined on the basis of the genotype of the markers using the polymorphism data obtained upon electrophoresis. The mapping identified a genetic marker (CaCY), which mapped to the shortest distance from the xcv-1 locus. The CaCY marker can be genotyped using primers Pr_CaCYF1 (SEQ ID NO:1) and Pr_CaCYR1 (SEQ ID NO:2).

1.4. Chromosome Walking

The identified marker, CaCY, which is closely linked to the xcv-1 gene (located at a distance of 0.22 centimorgan from xcv-1) allowed the initiation of the chromosome walking. In the first step, the primary pepper BAC clone (Clone No. 279) was identified with the help of the CaCY marker using multiplex PCR. The terminal sequences of the primary BAC clone (No. 279) were determined and primer pairs specific to them were designed. With the help of the specific primer pairs, BAC clones overlapping with BAC Clone No. 279 were identified (Clones No. 632 and 1248), and another set of specific primers were designed for their terminal sequences and additional overlapping clones were identified, then additional clones were isolated in a similar manner. Using the specific primer pairs designed for BAC Clones No. 66, 1191, 50, 877 and 472, the BAC ends were back-mapped to the genetic map thereby verifying the correct direction of the contig building. With the specific primer pair designed for the −40 end of BAC Clone No. 50, we managed to pass a recombination towards the xcv-1 gene, therefore, contig building was only continued into this direction. From BAC Clone No. 50, the contig was extended by another overlapping BAC clone in the above manner, and upon back-mapping marker 472_op, further recombinant individuals delimiting the contig comprising the xcv-1 gene could be identified.

1.5. Sequencing of BAC Clones Overlapping the Xcv-1 Region: Subcloning, Sequencing of the Subclones and Solid Sequencing In the next step, two BAC clones overlapping the xcv-1 region (No. 50 and 472) were sequenced. DNA sequencing was carried out in two ways: by subcloning and sequencing of the subclones from both sides, and by the new-generation Solid sequencing method developed by ABI.

2. Identification of the Xcv-1 Gene

2.1. Determination of the Gene Contents of the BAC Clones

The resulting DNA sequence data were handled and assembled into contigs giving overlapping segments by various computer programs. This "assembly" did not produce a sequence of the complete length of BAC but more than ten contigs, which were closed by the so-called primer walking technique. The sequences of the resulting partial BAC clones (No. 50 and 472) were determined.

The gene content of the two BAC clones were determined by the BLAST programmes (chiefly the blastn, blastx and blastp programmes) of NCBI (http://ncbi.nlm.nih.gov/BLAST/) and DFCI (http://compbio.dfci.harvard.edu/tgi/plant.html). On the basis of the gene content and gene order information, polymorph markers were prepared using specific primer pairs, and the genes were back-mapped. So far, a total of 13 protein-encoding genes were identified in the two BAC clones. On the basis of the mapping data, it was found that the xcv-1 gene is located between markers Pr6 and Pr4b as a single gene encoding more than 50 amino acids. The primer sequences of the markers are as follows: Pr6F1: SEQ ID NO:33, Pr6R1: SEQ ID NO:34, Pr4bF1: SEQ ID NO:35 and Pr4bR1: SEQ ID NO:36.

Next, the DNA sequence of both the xcv-1 gene and its wild-type counterpart (Xcv-1 gene) was determined in both parents using specific primer pairs; see SEQ ID NO:37 and SEQ ID NO:41, respectively.

Thus, the present invention relates to the xcv-1 gene isolated by the above method, which has the DNA sequence presented in SEQ ID NO:37. The cDNA sequence of the xcv-1 gene—which is the nucleotide sequence of SEQ ID NO:90—was generated, and is also covered by the scope of the invention.

The xcv-1 gene encodes a CYSTM protein, the xcv-1 protein, the amino acid sequence of which is that of SEQ ID NO:38, wherein the cysteine-rich transmembrane region (CYSTM region) of the protein carries a double Leu deletion at the locations corresponding to positions 87 and 88 of the wild-type Xcv-1 protein of SEQ ID NO:42. However, the invention also encompasses all those protein sequences which are proteins homologous to the xcv-1 protein and represent protein variants containing at least 53%, preferably 60% to 73%, more preferably 80% to 93% identical amino acids with respect to the last 13 amino acids of the C-terminus of the xcv-1 protein.

Furthermore, the present invention relates to vectors, preferably expression vectors, comprising the genes isolated and prepared according to the invention in a functional form. Preferred vectors useful for the purpose of the invention include the binary vectors of *Agrobacterium tumefaciens*, such as the pCAMBIA vector family (http://www.cambia.org/daisy/cambia/585).

Furthermore, the present invention relates to ZFN, TALEN and CRISPR/Cas nucleases specific to the interest sequence of the Xcv-1 gene, which are used to generate the 6-bp deletion or to inactivate (by knock-out) the genes homologous to the wild-type Xcv-1 DNA.

Furthermore, the present invention relates to host cells into which the vectors of the invention were introduced, e.g., by transformation or by genome editing techniques (ZFN, TALEN and CRISPR/Cas nuclease), and by means of which the desired 6-bp deletion was generated in the Xcv-1 homologous genes. Preferred host cells useful for the purpose of the invention include Solanaceae, Oryzae, Citroidieae etc. species.

The present invention also relates to a transformation method of generating a transgenic plant resistant to a biotic or abiotic factor, comprising the steps of: a) identifying one or more genes homologous to the wild-type Xcv-1 gene (SEQ ID NO:41) in said plant, preparing in vitro the genomic and cDNA sequences of the identified gene in a DNA form, generating in vitro a 6-bp mutation corresponding to the deletion of two amino acids in the segments encoding the CYSTM region of the one or more identified genes and transforming the cells of a sensitive plant with the one or more mutant genes thus obtained in a manner ensuring the functional expression thereof, b) inactivating the one ore more resident genes identified in step a) or the mRNA or protein thereof in the transformant plant cells, and c) regenerating the plant from the transformants and selecting the resistant individuals.

In step a) of the above method, genetic engineering methods well-known to those skilled in the art were used to identify the gene(s), to prepare them in a DNA form, to generate the mutations and to transform the plant cells.

In step b) of the above method, the resident genes homologous to the Xcv-1 gene are inactivated (silenced). Inactivation (silencing) of the resident genes is necessary because the function of the wild-type protein (pl. Xcv-1) is dominant over the function of the mutant protein (e.g., xcv-1), i.e., the latter function is recessive. Well-known methods are also available for inactivating the gene, i.e., for eliminating the function of the gene. Examples include but are not limited to the following: inhibiting the expression of the protein products of the resident genes using natural, chemical or insertion mutagenesis, amiRNA (artificial miRNA), RNAi (RNA interference) or other techniques; inactivating the resident gene(s) using nuclease deletion methods generating knock-out mutants. Preferably, the above-described TALEN, ZFN or CRISPR/Cas nuclease technique is used. By expressing the gene of a monoclonal antibody specific to the protein, one can inactivate the Xcv-1, or the homologous proteins.

It is important to note that the amiRNA technique has been successfully used to create resistance against viruses in plants (Niu et al., Nat. Biotechnol. 24:1420-1428, 2006), however, resistance to pathogenic bacteria such as Xe has not been created in plants with the amiRNA technique yet.

In step b) of a preferred embodiment of the method of the invention, the mRNA products of the resident gene(s) are functionally inactivated (silenced) by the amiRNA technique as follows: b1) preparing an amiRNA gene construct for the ribonucleotide sequence complementary to the CYSTM region of the mRNA of one or more genes homologous to the wild-type Xcv-1 gene and identified in the transformant plant cells obtained in step a); b2) cloning the construct obtained in step b1) into an appropriate vector; b3) transforming the transformant plant cells with the vector obtained in step b2) in a manner ensuring the functional expression of the amiRNA and inactivation of the mRNA products of the wild-type CYSTM gene(s); and c) regenerating the transformants obtained in step b3) and selecting the resistant plant.

The nucleases of the invention (engineered nucleases) are used for two genome editing functions in the present invention: on the one hand, for inactivating the resident genes in the transformant plant cells; on the other hand, for creating the desired 6-bp deletion in the gene homologous to the Xcv-1 gene in the genome of a sensitive plant cell. The two functions may also be combined, for example, in tomato, where the desired 6-bp deletion appears in one of the two homologous wild-type genes (SlXcv-1A, SEQ ID NO:49 and SlXcv-1B, SEQ ID NO:51), and the gene is inactivated upon a deletion or insertion in the other.

In a manner obvious to a skilled person, the target sequences of the above nucleases are selected in a manner ensuring that they cover the 6-bp sequence to be deleted in order to prevent the recognition and cleavage of the DNA segment already comprising the deletion, and that the desired 6-bp deletion can be created.

In another preferred embodiment of the method of the invention, the resident gene(s) is/are inactivated by a nuclease deletion (genome editing) method as follows: b1) preparing DNA constructs encoding TALEN-L and TALEN-R or ZFN-L and ZFN-R proteins specific to the gene sequence(s) encoding the CYSTM region of one or more genes homologous to the wild-type Xcv-1 gene and identified in the transformant plant cells obtained in step a), more specifically those specific to the DNA segments corresponding to the 6 nucleotides to be deleted and the surrounding nucleotides as target sequence in a manner ensuring that the 6 nucleotides to be deleted from the wild-type gene are positioned in the middle of the spacer segment of the TALEN-L plus TALEN-R or ZFN-L plus ZFN-R pairs, or by preparing a CRISPR/Cas construct comprising the sgRNA gene sequence specific to the 6 nucleotides to be deleted from the wild-type gene and the surrounding nucleotides as target sequence; b2) cloning the constructs obtained in step b1) into an appropriate vector; b3) transforming the plant cells with a vector comprising the constructs obtained in step b1) in a manner ensuring the functional expression of the transgenes; c) identifying knock-out deletion or insertion mutations in the genes homologous to the wild-type Xcv-1 gene (SEQ ID NO:41); d) selecting the plant cells containing the mutations identified in step c); e) regenerating the plant cells identified in step d) and selecting the resistant plants, and f) removing the transgenes comprising the TALEN or ZFN constructs or the CRISPR/Cas constructs containing the gene of the sgRNS protein by genetic segregation.

The present invention also relates to a method for generating a mutant plant showing an abiotic or biotic resistance using a genome editing method, comprising the steps of: a) identifying one or more genes homologous to the wild-type Xcv-1 gene (SEQ ID NO:41) in a sensitive plant; b) preparing DNA constructs encoding TALEN-L and TALEN-R or ZFN-L and ZFN-R proteins specific to the gene sequence encoding the CYSTM region of one or more genes homologous to the wild-type Xcv-1 gene and identified in step a), more specifically those specific to the 6 nucleotides to be deleted and the surrounding nucleotides as target sequence in a manner ensuring that the 6 nucleotides to be deleted from the wild-type gene are positioned in the middle of the spacer segment of TALEN-L plus TALEN-R or ZFN-L plus ZFN-R pairs, or by preparing a CRISPR/Cas construct comprising the sgRNA gene sequence specific to the 6 nucleotides to be deleted from the wild-type gene and the surrounding nucleotides as target sequence; c) cloning the construct obtained in step b) into an appropriate vector; d) transforming sensitive plant cells with a vector comprising the construct obtained in step b) in a manner ensuring the functional expression of the transgenes and the generation of the 6-bp deletion in the CYSTM region by the nuclease; e) identifying the transformants carrying mutations showing the 6-bp deletion in the CYSTM region of the genes homologous to the wild-type Xcv-1 gene (SEQ ID NO:41); f) regenerating the plant cells having the mutation identified in step e) and selecting the resistant plants; and g) removing the transgenes comprising the TALEN or ZFN constructs or CRISPR/Cas constructs containing the gene of the sgRNS protein by genetic segregation.

Furthermore, the mutant plants showing biotic or abiotic resistance according to the invention can be generated by introducing TALEN or ZFN proteins specific to the CYSTM region into the plant using non-pathogenic bacteria, said method, comprising the steps of: a) identifying one or more genes homologous to the wild-type Xcv-1 gene (SEQ ID NO:41) in a sensitive plant; b) preparing DNA constructs encoding TALEN-L plus TALEN-R or ZFN-L plus ZFN-R proteins specific to the DNA segment encoding the CYSTM region of the gene identified in step a) in a manner ensuring that the 6 nucleotides to be deleted from the wild-type gene are positioned in the middle of the spacer segment of the TALEN-L plus TALEN-R or ZFN-L plus ZFN-R pairs; c) cloning the constructs obtained in step b) into an appropriate bacterial vector and introducing them into non-pathogenic bacteria with active type three secretion system using said vector; d) infecting the sensitive plant with bacteria obtained step c); and e) regenerating a resistant plant from the infected plant tissue.

In the methods of the invention, not only the genomic sequences but also the cDNA sequences of the genes homologous to the wild-type Xcv-1 or the mutant xcv-1 gene can be used with identical results since the same protein is expressed from both.

Using the method of the invention, resistance can be created in plants which are sensitive to *Xanthomonas* species, such as *Xanthomonas euvesicatoria, Xanthomonas perforans, Xanthomonas gardneri, Xanthomonas vesicatoria* pv. *oryzae*, and other *Xanthomonas* species. One such preferred plant is tomato.

One of the most dangerous pathogens of tomato is *Xanthomonas euvesicatoria* (Xe), which also causes severe damage to pepper. Unlike pepper, tomato has not developed appropriate natural resistance, which would ensure sufficient protection. Thus, tomato production is still highly threatened by Xe infection (Hutton S. F. et al., Theor. Appl. Genet. 121:1275-87, 2010). The xcv-1 gene identified in pepper may also provide resistance to Xe infection in tomato by ensuring the introduction and functional expression of the mutant tomato genes Slxcv-1A and/or Slxcv-1B (SEQ ID NO:59 and/or SEQ ID NO:66), which are homologous to the xcv-1 gene, in the tomato genome followed by the inactivation of the dominant resident genes SlXcv-1A and SlXcv-1B (SEQ ID NO:49 and SEQ ID NO:51) homologous to the wild-type Xcv-1 gene, i.e., by generating non-functional variants thereof.

The tomato plant resistant to *Xanthomonas euvesicatoria* can be generated using the following methods of the invention:

transforming the cells of the tomato plant with the mutant genes Slxcv-1A and/or Slxcv-1B carrying the double Leu deletion, followed by inhibiting the function of the SlXcv-1A and/or SlXcv-1B genes using the amiRNA technique; or transforming the cells of the tomato plant with the mutant genes Slxcv-1A and/or Slxcv-1B carrying the double Leu deletion, followed by inactivating the resident genes SlXcv-1A and/or SLXcv-1B located there using the ZFN nuclease or TALEN nuclease or CRISPR/Cas nuclease technique; or transforming the cells of the tomato plant with the mutant genes Slxcv-1A and/or Slxcv-1B carrying the double Leu deletion; followed by identifying the mutations inactivating the SlXcv-1A and/or SlXcv-1B gene using the TILLING or a similar technique upon or without mutagenesis; or creating the desired 6-bp deletion in genes SlXcv-1A and/or SlXcv-1B in the genome of the sensitive tomato plant using a specific nuclease-based genome editing method, which provides resistance.

Thus, one object of the present invention is a method for generating a tomato plant resistant to *Xanthomonas euvesicatoria*, comprising the steps of:

a) identifying the resident genes SlXcv-1A and SlXcv-1B (SEQ ID NO:49 and 51, respectively), which are homologous to the wild-type Xcv-1 gene in the tomato plant; b) preparing in vitro the genomic and cDNA sequences of the identified genes in the form of a DNA; c) creating in vitro the 6-bp deletion in the positions corresponding to the deletions in the xcv-1 gene thereby generating constructs carrying the mutant genes Slxcv-1A and Slxcv-1B (SEQ ID NO:59 and 66, respectively) or their cDNA sequences (SEQ ID NO:88 and 89, respectively); d) cloning the constructs obtained in step c) into an appropriate vector and transforming the cells of the tomato plant with the resulting vector in a manner ensuring the functional expression of the transgenes; e) preparing an amiRNA gene construct for silencing the wild-type genes SlXcv-1A and SlXcv-1B (SEQ ID NO:49 and/or SEQ ID NO:51); f) cloning the construct obtained in step e) into an appropriate vector; g) transforming the plant cells generated in step d) with the vector obtained in step f) in a manner ensuring the expression of the amiRNA and inactivation of the mRNA products of the wild-type CYSTM genes SlXcv-1A and SlXcv-1B; and h) regenerating the transformants obtained in step g) and selecting the resistant plant.

In a preferred embodiment the amiRNS gene construct is specific to the complementary ribonucleotide sequence corresponding to the CYSTM region of the wild type SlXcv-1A and/or SlXcv-1B genes (SEQ ID NO:49 and/or SEQ ID NO:51) more specifically an amiRNA gene construct specific to the 6 nucleotides to be deleted and the surrounding nucleotides (SlXe1-amiRNA, SEQ ID NO: 74). In a preferred embodiment the amiRNA gene construct comprises the nucleic acid molecule according to the invention.

The present invention also relates to another method for generating a tomato plant resistant to *Xanthomonas euvesicatoria*, comprising the steps of: repeating steps a) to d) above; e) preparing proteins TALEN-L (SEQ ID NO:78) and TALEN-R1 (SEQ ID NO:79) and TALEN-R2 (SEQ ID NO:80) specific to the target sequences (SEQ ID NO:75, 76, 77) specific to the CYSTM region of the wild-type SlXcv-1A and SlXcv-1B gene, or DNA constructs encoding the proteins ZFN-L and ZFN-R specific to SEQ ID NO: 86 and 87 in a manner ensuring that the 6 nucleotides to be deleted from the wild-type gene are positioned in the middle of the spacer segment of the TALEN-L plus TALEN-R or ZFN-L plus ZFN-R pairs, or by preparing a CRISPR/Cas construct comprising the sgRNA gene sequence specific to the 6 nucleotides to be deleted from the wild-type gene and the surrounding nucleotides as target sequence (SEQ ID NO: 81); f) cloning the construct obtained in step e) into an appropriate vector; g) transforming the plant cells generated in step d) with the vector obtained in step f) in a manner ensuring the functional expression of the above TALEN or ZFN or CRISPR/Cas nuclease transgenes and the functional inactivation of genes SlXcv-1A and SlXcv-1B by them; h) identifying deletion or insertion knock-out mutations in the transformant cells; i) regenerating the plant cells having the mutation identified in step h) and selecting the resistant plants; and f) removing the nuclease transgenes TALEN-L plus TALEN-R or ZFN-L plus ZFN-R or CRISPR/Cas by genetic segregation.

The present invention also relates to yet another method for generating a tomato plant resistant to *Xanthomonas euvesicatoria*, comprising the steps of: a) identifying the resident genes SlXcv-1A (SEQ ID NO:49) and SlXcv-1B (SEQ ID NO:51), which are homologous to the wild-type Xcv-1 gene in the tomato plant; b) preparing proteins TALEN-L (SEQ ID NO:78) and TALEN-R1 (SEQ ID NO:79) and TALEN-R2 (SEQ ID NO:80) specific to the target sequences (SEQ ID NO:75, 76, 77) specific to the CYSTM region of the wild-type SlXcv4A and SlXcv-1B gene, or DNA constructs encoding the proteins ZFN-L and ZFN-R specific to SEQ ID NO: 86 and 87 in a manner ensuring that the 6 nucleotides to be deleted from the wild-type gene are positioned in the middle of the spacer segment of the TALEN-L plus TALEN-R or ZFN-L plus ZFN-R pairs, or by preparing a CRISPR/Cas construct comprising the sgRNA gene sequence specific to the 6 nucleotides to be deleted from the wild-type gene and the surrounding nucleotides as target sequence (SEQ ID NO: 81); c) cloning the construct obtained in step b) into an appropriate vector; d) transforming the cells of the tomato plant with the vector obtained in step c) in a manner ensuring the functional expression of the above TALEN or ZFN or CRISPR/Cas nuclease transgenes and the creation of the 6-bp deletion in the CYSTM region of genes SlXcv-1A and SlXcv-1B by them; e) identifying the transformants carrying the 6-bp deletion in the CYSTM region of the wild-type genes SlXcv-1A and SlXcv-1B; f) regenerating the transformants having the mutation identified in step e) and selecting the resistant plant; and g) removing the nuclease transgenes TALEN-L plus TALEN-R or ZFN-L plus ZFN-R or CRISPR/Cas by genetic segregation.

The development of resistant cultivars has been the most effective, economical and environmental friendly strategy to control disease epidemic of cultivated plants. Out of many possibilities, pyramided resistance is far more durable than resistance that is controlled by a single dominant R genes (usually causing HR), because new races of pathogens could easily evolve to overcome or escape the resistance consequently plant resistant trait breaks down. Traditional breeding combined with molecular markers based marker assisted selection has made it possible to identify and pyramid valuable genes of agronomic importance in resistance. In addition to this strategy, transgenic approaches serve further possibility to pyramid resistant genes in plant cultivars. As mentioned above tomato, a close relative of pepper is highly susceptible to Xe. To fight against this pathogen and establish Xe resistant tomato, transgenic tomato plants expressing the Bs2 resistance gene from pepper was constructed recently (Horvath et al., PLoS One.; 7(8):e42036, 2012). In replicated multi-year field trials under commercial type growing conditions demonstrated improved resistance to bacterial spot disease caused by Xe. Taking into account the beneficial impact of pyramided gene configuration the above mentioned tomato Bs2 containing can be a starting material to produce double resistant derivatives by expressing the Slxcv-1A and/or Slxcv-1B gene carrying the beneficial 6 bp deletion as described in this invention. By this way highly resistant and durable Xe resistant cultivars of tomato can be breeded for commercial production. A skilled person would recognize that the resistance based on the expression of Slxcv-1A and/or Slxcv-1B gene can be combined not only with Bs2, but with other genes too, which may confer resistance to Xe in tomato including but not limited to Bs1, Bs3, Bs4, bs5, bs6.

In addition to pepper and tomato, several other plants are severely infected by *Xanthomonas* species causing disease on rice, potato, citrus, banana, grape, etc. (Dangle et al. Science 341: 746, 2013). The desired 6 bp deletion derivative can also be generated in the Xcv-1 homologous gene(s) of these plants and can be combined with other type of resistance genes against *Xanthomonas*. Accordingly, one can generated rice plants resistant against *Xanthomonas oryzae*, or citrus plants resistant against *Xanthomonas citri* pv. *citri* or *Xanthomonas axonopodis* pv. *citri* or banana plants resistant against *Xanthomonas campestris* pv. *musacearum*.

In addition, the method of the invention can be used to create resistance to an abiotic or biotic factor other than *Xanthomonas* sp. in plants.

The present invention further relates to mutant plants resistant to a biotic or abiotic factor, which carry a deletion of two amino acids in their CYSTM region in comparison with the wild-type plant. Preferably, the mutant plant is a pepper plant (*Capsicum annuum*), a tomato plant (*Solanum lycopersicum*), a plant from the Solanaceae family, e.g., potato, eggplant etc., a citrus (Citroideae), e.g., orange (*Citrus aurantium*), mandarin (*Citrus reticulata*), lemon (*Citrus x medica* L.), grapefruit (*Citrus x paradisi*), pomelo (*Citrus maxima* or *grandis*) etc., a plant from the Brassicaceae family, e.g., cabbage (*Brassica oleracea* convar. *capitata* var. *alba*), radish (*Raphanus sativus*), cauliflower (*Brassica oleracea* convar. *botrytis* var. *botrytis*), rape (*Brassica napus*) etc., a monocot plant (Monocotyledonae), e.g., rice (*Oryzae* sp.), maize (*Zea mays*), wheat (*Triticum* sp.), rye (*Secale* sp.), barley (*Hordeum vulgare*), millet (*Panicum* sp.), etc., a plant from the Fabaceae or Leguminosae families, e.g., alfafa (*Medicago* sp.), bean (*Phaseolus* sp.), pea (*Pisum* sp.), soy (*Glycine* sp.), horse bean (*Faba* sp.), lupine (*Lupinus* sp.), clover (*Trifolium* sp.), peanut (*Arachis* sp.), vicia (*Vicia* sp.), lathyrus (*Lathyrus* sp.), lentil (*Lens* sp.), chick-pea (*Cicer* sp.), mung bean (*Vigna* sp.), pigeon pea (*Cajanus cajan*) etc., a plant from the Cucurbitaceae family, e.g., pumpkin (*Cucurbita* sp.), cucumber (*Cucumis* sp.), melons (*Citrullus* sp.) etc., a plant form the Rosaceae family, e.g., apple (*Malus* sp.), pear (*Pyrus communis*), quince (*Cydonia oblonga*), cherry (*Prunus* subg. *Cerasus*), sour cherry (*Prunus cerasus*), plum (*Prunus domestica* subsp. *domestica*), apricot (*Prunus armeniaca*), peach (*Prunus persica*), grape (*Vitis vinifera*), etc., in which resistance has been created.

More preferably, the mutant plant is a mutant tomato plant (*Solanum lycopersicum*) resistant to Xe.

Another object of the present invention are the seeds and the products of the mutant plants generated by this invention, including but not limited to fruits, juice, paste, etc., preferably the seeds and products of the mutant tomato plant and its progeny.

Furthermore, we can raise antibodies against the xcv-1 protein of the invention, which can be used as probes in in vitro methods performed in plant-derived cell lines in order to test whether a given plant is resistant to Xe or not. The methods of raising antibodies and such techniques are well known to those skilled in the art.

The present invention further relates to gene probes, which are specific to the xcv-1 gene or its homologous genes and hybridizing with them under stringent conditions.

Another objects of the present invention are primer pairs, which are specific to the xcv-1 gene or its homologous genes, especially to the Slxcv-1A and/or the SlXcv-1B, and can be used to genotype plants carrying the 6 bp deletion including but not limited to markere assisted selection.

The invention is described in more detail through the following examples without limiting the scope of the invention.

Example 1

Genetic Crosses and Analysis of the F2 Progeny of the Xcv Plant

For the generation of F1 individuals, commercially available *C. annuum* var. Feherozon sensitive to *Xanthomonas euvesicatoria* (Xe) was used as the father parent (marked as F0), and *Capsicum annuum* var. T1/1 carrying Xe resistance—an individual of Gene Bank Accession No. PI163192—was used as the mother parent (T1/1). After the crossing, 45 F1 seeds from the mother plant were sown and F2 plants were grown from them. When plants reached the 8-leaved age, a *Xanthomonas euvesicatoria* infection test was used to determine the sensitivity of the plants to Xe. Finally, 20 F2 individuals—8 resistant and 12 sensitive individuals (see Table 1)—were selected for the general mapping experiments; on the other hand, more than 3000 F2 individuals were used for the fine-mapping of the Xe resistance gene (xcv-1).

TABLE 1

Phenotypes of 20 F2 individuals of the segregating population after infection by *Xanthomonas euvesicatoria* (xcv phenotype);

| plant name | xcv phenotype | plant name | xvc phenotype |
|---|---|---|---|
| 1 | S | 11 | R |
| 2 | S | 12 | R |
| 3 | S | 13 | R |
| 4 | S | 14 | R |
| 5 | S | 15 | R |
| 6 | S | 16 | R |
| 7 | S | 17 | S |

TABLE 1-continued

Phenotypes of 20 F2 individuals of the segregating population after infection by *Xanthomonas euvesicatoria* (xcv phenotype);

| plant name | xcv phenotype | plant name | xvc phenotype |
|---|---|---|---|
| 8 | S | 18 | S |
| 9 | R | 19 | S |
| 10 | R | 20 | S |

S = sensitive;
R = resistant

Example 2

Identification of Markers Linked to the Xcv-1 Gene of the T1/1 Mutant Plant

Identification by genetic mapping of molecular markers mapping close to the mutated xcv gene, i.e., those linked to Xcv resistance, was carried out using the 20 F2 progeny mentioned in Example 1. Total DNA from fresh leaves was subjected to PCR amplification using specific primers designed on the basis of pepper sequences available in the databases, and the resulting fragments were subjected to electrophoresis on agarose gels or on so-called SSCP acrylamide gels. In order to visualise the DNA fragments, agarose gels and acrylamide gels were stained using ethidium bromide and silver, respectively. The linkage of markers showing polymorphism on the agarose or SSCP gels was determined by colour mapping (Kiss et al., Acta Biologica Hungarica 49:47-64, 1998) with respect to the xcv/Xcv phenotype after ascertaining the homozygote or heterozygote status. As a result of the systematic mapping, a single marker designated as CaCY showed a distance of 0.22 centimorgan.

The identifiers of the primers of the CaCY marker (Pr-_CACY_F1 and Pr_CACY_R1) are SEQ ID NO:1 and SEQ ID NO:2, respectively.

Since other mapped markers were either unlinked to the xcv-1 gene or were located at much greater genetic distances; therefore the so-called chromosome walking was initiated using the CaCY marker to physically the xcv-1 gene.

Example 3

Isolation of BAC Clones Overlapping with the Xcv-1 Mutation, Contig Building

A primary BAC clone (No. 279) was isolated using the molecular marker showing the strongest linkage to the xcv-1 mutation, i.e., CaCY. The primary and other BAC clones are isolated using multiplex PCR from a BAC library comprising 380,000 BACs, which was prepared from an Xcv resistant pepper (*Capsicum annuum*) plant and ensures a 22-fold coverage of the pepper genome (Bukovinszki et al., VII. Hungarian Congress on Genetics, Abstract Book, p. 91, 2007).

Both ends of BAC Clone No. 279 were sequenced and additional two BAC clones were identified using primer pairs specific to these sequences: BAC Clone No. 1248 using primers Pr_279 op F1 (SEQ ID NO:3) and Pr_279 op R1 (SEQ ID NO:4), and BAC Clone No. 632 using primer pair Pr_279-40 F1 (SEQ ID NO:5) plus Pr_279-40 R1 (SEQ ID NO:6).

Primer pairs specific to the terminal sequences of BAC No. 1248 were used to identify BAC Clone No. 1191: the pair consisted of primers Pr_1248 op F1 (SEQ ID NO:7) and Pr_1248 op R1 (SEQ ID NO:8), and as control, BAC Clone No. 279 was reidentified using primer pair Pr_1248-40 F1 (SEQ ID NO:9) plus Pr_1248-40 R1 (SEQ ID NO:10).

Primer pairs specific to the terminal sequences of BAC No. 1191 were used to identify BAC Clone No. 877: the pair consisted of primers Pr_1191-40 F1 (SEQ ID NO:11) and Pr_1191-40 R1 (SEQ ID NO:12), and as control, BAC Clone No. 1248 was reidentified using primer pair Pr_1191 op F1 (SEQ ID NO:13) plus Pr_1191 op R1 (SEQ ID NO:14).

Primer pair Pr_877-40 F1 (SEQ ID NO:15) plus Pr_877-40 R1 (SEQ ID NO:16) was designed for the −40 terminal sequence of BAC No. 877, and was used for genetic back-mapping.

Primer pairs specific to the terminal sequences of BAC No. 632 were used to identify BAC Clone No. 66: the pair consisted of primers Pr_632-40 F1 (SEQ ID NO:17) and Pr_632-40 R1 (SEQ ID NO:18), and as control, BAC Clone No. 279 was reidentified using primer pair Pr_632 op F1 (SEQ ID NO:19) plus Pr_632 op R1 (SEQ ID NO:20).

Primer pairs specific to the terminal sequences of BAC No. 66 were used to identify BAC Clone No. 50: the pair consisted of primers Pr_66-40 F1 (SEQ ID NO:21) and Pr_66-40 R1 (SEQ ID NO:22), and as control, BAC Clone No. 632 was reidentified using primer pair Pr_66 op F1 (SEQ ID NO:23) plus Pr_66 op R1 (SEQ ID NO:24).

Primer pairs specific to the terminal sequences of BAC No. 50 were used to identify BAC Clone No. 472: the pair consisted of primers Pr_50 op F1 (SEQ ID NO:25) and Pr_50 op R1 (SEQ ID NO:26), and as control, BAC Clone No. 66 was reidentified using primer pair Pr_50-40 F1 (SEQ ID NO:27) plus Pr_50-40 R1 (SEQ ID NO:28).

On the one hand, primer pairs designed for the terminal sequences of BAC No. 472 were used to reidentify BAC Clone No. 66 as control: the pair consisted of primers Pr_472-40 F1 (SEQ ID NO:29) and Pr_472-40 R1 (SEQ ID NO:30), and primer pair Pr_472 op F1 (SEQ ID NO:31) plus Pr_472 op R1 (SEQ ID NO:32) was used for genetic back-mapping.

Thus, by classifying BAC Clones into contig groups, we could draft the so-called xcv contig (FIG. 1) characteristic of the xcv region, which physically covers the xcv-1 gene.

Example 4

More Precise Determination of the Location of the Xcv-1 Gene within the Contig by Identifying the Recombination Sites that are Nearest to the Mutation Determining the location of the xcv-1 gene more precisely within the xcv contig is of key importance since the nearer the given molecular marker is, the lower number of BAC clones has to be sequenced, and this results in fewer candidate genes. More precise determination of the location of the xcv-1 gene within the xcv contig was performed as follows. On the one hand, the number of individuals in the F2 segregation population was increased to allow the analysis of as many recombination events as possible. Finally, a total of 3119 individuals were included in the genetic analysis. On the other hand, molecular markers were developed using terminal sequences of overlapping BACs and were back-mapped using the population segregating the xcv-1 gene. On the basis of the results, it was concluded that the position of the xcv-1 gene is between the −40 end of BAC No. 50 and the op end of BAC No. 472 separated by three and four recombination events, respectively.

Example 5

Subcloning of BAC Clone No. 50 and Sequencing of the Subclones

Subcloning of BAC Clone No. 50 was performed after cleavage by restriction enzymes BamHI, EcoRI and HindIII. Upon purification, the subclones were digested using BamHI, HindIII and EcoRI, and the resulting fragments are cloned into vectors digested with BamHI, HindIII és EcoRI and transformed into *Escherichia coli* cells. The sequences of the fluorescence-labelled amplificates of the recombinant clones were determined using ABI 373 and ABI 377 automated sequencers (Perkin Elmer Applied Biosystems; 850 Lincoln Centre Drive Foster City, Calif. 94404 USA).

The DNA sequence of BAC Clone No. 50 was also determined using second generation sequencing technologies (SOLID and Iontorrent, Applied Biosystems), as well as using the "primer walking" technique until the complete sequence was obtained.

Example 6

Fine-Mapping of the Xcv-1 Region

Partial sequence data were stored in a computer, and the analysis was started by determining their correct order on the basis of their overlapping sequences. In a manner obvious to those skilled in sequence alignment and sequence analysis, the overlapping terminal sequences of the BAC clones and their subclones generated by restriction digestion provide help for the assembly of the sequences and for the determination of the relative locations of the subclones generated by random and restriction digestion and of the BAC clones. Upon the assembly of the partial sequences, we succeeded in compiling the sequence of BAC Clone No. 50, which was then used to develop genetic markers at various distances from the BAC termini. When these genetic markers were back-mapped in the mapping population, it was revealed that the xcv-1 gene is located between PCR-based markers Pr6 and Pr4b. The primer sequences of markers Pr6 and Pr4b are as follows: Pr6F1: SEQ ID NO:33, Pr6R1: SEQ ID NO:34, and Pr4bF1: SEQ ID NO:35, Pr4bR1: SEQ ID NO:36.

Example 7

Sequence Analysis of the Xcv1 Region and Detailed Assessment of the Xcv-1 Gene Upon obtaining the nucleotide sequence of the DNA segment between markers Pr4b and Pr6, the databases of NCBI (National Center for Biotechnology Information http://www.ncbi.nlm.nih.gov/BLAST/), DFCI (http://compbio.dfci.harvard.edu/tgi/plant.html), Medicago HapMap (http://www.medicagohapmap.org/?genome) and *Arabidopsis* (http://www.arabidopsis.org) were successfully searched for homologous genes. The sequences were evaluated with a view to the homology between the sequences, and the common general characteristics of the gene structures [consensus sequences such as start and stop codons; consensus sequences typical of open reading frames (ORFs), exons and introns such as the GT-AG rule, point of divergence etc.].

Sequence analysis was facilitated by the fact that only one gene encoding for a protein of more than 50 amino acids—which is the xcv-1 gene itself—is present between the two genetic markers located on the right and left side, respectively, of the xcv-1 gene responsible for the phenotype, which can be distinguished by single recombination events. The sequence of the DNA segment comprising the xcv-1 gene is represented by the nucleotide sequence of SEQ ID NO:37.

The databases were successfully searched for DNA sequences similar to the xcv-1 gene, and we noted that homologous cDNA sequences occur in the so-called EST (Expressed Sequence Tags) databanks in the case of *C. annuum* as well. These sequences are a result of random sequencing by laboratories into cDNA clones from cDNA libraries of various organs, tissues or cells or groups of cells (root, stem, leaves, fruit, flower, pistil, stamen, pollen etc.) without having any information regarding their functions. For example, these include sequence TC17947 (SEQ ID NO:39) from *C. annuum* found in the DFCI database (http://compbio.dfci.harvard.edu/tgi/plant.html), which is presented in the form of the so-called TC (Tentative Consensus), i.e., the DNA form of the mRNA of a gene. The base composition of the TCs are edited by aligning cDNA sequences of various lengths derived from a single gene and determining the consensus sequence. The protein encoded by sequence TC17947 is shown by the amino acid sequence of SEQ ID NO:40. The mutation responsible for the Xe resistance can be identified by searching for differences in the nucleotide sequence of the genome region (SEQ ID NO:37) comprising the xcv-1 gene from the mutant plant in comparison with the homologous regions of the sensitive pepper plant (SEQ ID NO:41). Such differences can be found by comparing the nucleotide sequence of the genomic region (SEQ ID NO:37) comprising the xcv-1 gene with the genomic (SEQ ID NO:41) sequence from the sensitive pepper (*C. annuum* var. Feherozon) plant. Upon aligning SEQ ID NO:37 and SEQ ID NO:41, it was found that the sequence from the resistant plant is shorter by 6 bp at a certain location. When the TC17947 sequence (SEQ ID NO:39) is aligned with the sequence (SEQ ID NO:37) from the resistant plant, then the cDNAs can be aligned to the genomic sequence at three different segments (these are the exons) (alignment of the genomic sequence of a gene to its cDNA sequence allows for the determination of the exact location of the exons and introns present in the gene). These three segments are separated by 2 introns of the genomic sequence (see SEQ ID NO:37). While the first and second segment of the TC17947 sequence shows 100% identity to the genomic sequence, the cDNA sequence of the third segment is longer by 6 bases at the very location where the two genomic sequences also show a difference of 6 bases. Since only one sequence typical of a gene encoding a protein [putative promoter segment, 5' UTR, exons, introns, 3'-UTR, start codon (ATG), stop codon (TGA), conserved exon/intron and intron/exon boundaries recognisable on the basis of the so-called GT-AG rule and by the point of divergence, Poly-A site etc.] is present the DNA segment in question, it is assumed that the protein variant carrying the 6-base deletion in the third exon of the genomic sequence is responsible for the resistance. Thus, as a consequence of this deletion, protein synthesis is normal but the resulting protein is shorter by 2 amino acids (see amino acid sequences SEQ ID NO:38 and SEQ ID NO:42).

The putative first codon of the wild-type Xcv-1 gene is the ATG start codon starting at nucleotide 917 of the genomic fragment, and the stop codon is the TAG stop codon starting at nucleotide 2076. The sequences typical of promoter regions are located in the putative promoter region at the 5'-end of the gene. In addition, a polyA site is present at the 3'-end of the gene.

The activity—i.e., the transcription—of genes Xcv-1 and xcv-1 in the cells is also confirmed by the fact that mRNAs corresponding to the two sequences were detected: mRNA segments lacking the 6-base deletion and mRNA segments containing the 6-base deletion were identified from the sensitive plant and the resistant plant, respectively, upon Solid type mRNA sequencing.

The amino acid sequence of the protein of the Xcv-1 gene can be deduced from the predicted cDNA sequence of the Xcv-1 (see features of SEQ ID NO:41). The longest amino acid sequence containing an open reading frame (ORF) deduced from the Xcv-1 cDNA is indicated by SEQ ID NO:42. The Xcv-1 protein consists of 92 amino acids. This protein contains characteristic sequence portions (e.g., the C-terminal transmembrane region), which can be determined using typical features accumulated in data banks and bioinformatics methods (e.g., TMpred and MPEx programmes). As a result of the bioinformatic analysis, it can be concluded that the intracellular part of the molecule starts with an N-terminus followed by a GYPQ (SEQ ID NO:151)-rich portion of 5 to 6 amino acids which contains a repeat sequence (GYPPE-GYPKD-SYPPP-GYPQQ-GYPQQ-GYPQQ-GYPPQ-GYPPQ-YAPQY; SEQ ID NO:126), and a linker segment is attached to the a C-terminal portion, which is a so called Tail Anchored (TA) section extending into the membrane (amino acids 72 to 88). The transmembrane region is terminated by amino acids with a negative charge (aspartic acid, glutamic acid) or polar amino acids (asparagine). The transmembrane region of the Xcv-1 protein can be detected on the basis of hydrophobicity using programmes predicting transmembrane regions. Without limitation, these include, for example, the "DAS"-Transmembrane Prediction programme (http://www.sbc.su.se/~miklos/DAS/), and the Tmpred software (http://www.ch.embnet.org/software/TMPRED_form.html). FIG. 2 shows the TM curve of the Xcv-1 protein (SEQ ID NO:42) predicted by the "DAS"-Transmembrane Prediction programme. The Xcv-1 protein belongs to the CYSTM family of proteins (Venancio T. M. and Aravind L. Bioinformatics 26:149-152, 2010).

Identification of cDNA sequences from various tissues supports the fact that the Xcv-1 gene is expressed in different pepper species and in their various tissues from root to flower [see the ESTs constituting the TC17497 sequence found in the DFCI data bank (SEQ ID NO:39); (http://compbio.dfci.harvard.edu/tgi/plant.html)].

In comparison with the wild-type gene, the protein product of the xcv-1 gene is shorter by 2 amino acids in the TM region. No sequences showing 100% percent identity with the xcv-1 protein were found in the data banks. Consequently, a new protein was identified to which the Xe resistance could be assigned on the basis of the data and experimental results.

Example 8

Intracellular Localisation of Polypeptides Xcv-1 and Xcv-1

To determine the intracellular localisation of polypeptides Xcv-1 and xcv-1, the coding sequence of the Green Fluorescent Protein (GFP) (Accession no: AF234298, nucleotides 2 to 757) is cloned in front of genes Xcv-1 and xcv-1, and is introduced into *Nicotiana bentamiana*, a plant of the Solanaceae family, through *Agrobacterium tumefaciens*-mediated gene transfer. Transformation is preferably carried out in a manner ensuring a so-called transient expression (Martin K. et al., Plant J. 59:150-62, 2010), as a result of which the GFP-Xcv-1/GFP-xcv-1 constructs are not stably incorporated into the genome of the plant but the transgene is expressed from a DNA in an extrachromosomal state. The experiment was carried out as follows:

First, the structural gene of GFP was cloned into a pGemT-Easy vector as follows: the coding sequence of GFP was amplified using the DNA of the pCambia1302 plasmid (www.cambia.org, Marker Gene Technologies, Inc. www-.markergene.com) as template, and SEQ ID NO:43 and SEQ ID NO:44 as primers, and the resulting PCR product was cloned into a pGemT-Easy vector. The resulting plasmid was designated 'pNcoGFPXba'. In the next step, leaf samples were taken from *C. annuum* var. T1/1 and *C. annuum* var. Feherozon plants in the six-leaved stage, and a QIAGEN RNA isolation kit (RNeasy Mini Kit, http://www.qiagen-.com) was used to isolate RNA, and the SMART™ cDNA Library Construction Kit (http://www.clontech.com) was used to synthesise double-stranded cDNA. The cDNAs of Xcv-1 and xcv-1 were amplified and cloned in a PCR reaction using the resulting cDNA preparation. To amplify the Xcv-1 allele, cDNA from *C. annuum* var. Feherozon and primers SEQ ID NO:45 and SEQ ID NO:46 were used for the amplification. The PCR reaction was performed as described in Example 2. The resulting fragment was cloned into a pGemT-Easy plasmid. The resulting plasmid was designated 'pXcv-1CaFo'. Cloning of the xcv-1 allele was performed in a similar way except for using the cDNA of *C. annuum* var. T1/1 and the primers represented by SEQ ID NO:45 and SEQ ID NO:46. The resulting plasmid was designated 'pxcv-1CaT1'. In the third phase, plasmids 'pXcv-1CaFo' and 'pxcv-1 CaT1' were digested with the enzymes XbaI and BcuI, and were cloned into a 'pNcoGFPXba' plasmid digested with XbaI and BcuI. The resulting plasmids were designated 'pGFP-Xcv-1CaFo' and 'pGFP-xcv-1 CaT1', respectively. In the last step, plasmids 'pGFP-Xcv-1 CaFo' and 'pGFP-xcv-1CaT1' were digested with SalI, and the plasmid pCambia 1302 was digested with BstEII, and then all three preparations were digested with Mung Bean Nuclease according to manufacturer's (New England Biolabs, Inc, www.neb.com) instructions. The blunt-ended linear molecules 'pGFP-Xcv-1CaFo' and pCambia 1302, and 'pGFP-xcv-1CaT1' and pCambia 1302 were mixed, and both preparations were digested with the enzyme NcoI, ligated and transformed into *E. coli* cells. The transformants were grown on kanamycin-containing plates, where only the pCambia1302 derivatives grow but not the pGemT-Easy derivatives. Among the transformant colonies, those comprising the fusion products GFP-Xcv-1 and GFP-xcv-1 were identified. The two products were designated "pCambia-GFP-Xcv-1CaFO" and 'pCambia-GFP-xcv-1 CaT1'. The sequences of the two fusion products are shown in SEQ ID NO: 47 and SEQ ID NO:48, respectively.

The plasmids 'pCambia-GFP-Xcv-1 CaFO' and 'pCambia-GFP-xcv-1 CaT1' plasmids were transferred into *A. tumefaciens* C58 by triparental mating, followed by growing the *A. tumefaciens* strains comprising the two constructs ('pCambia-GFP-Xcv-1CaFO' and 'pCambia-GFP-xcv-1CaT1') on solid media and infiltrating into *Nicotiana bentamiana* leaves in accordance with the method described in the relevant literature. After 48 hours, protoplasts were prepared from the leaf areas giving green fluorescence under UV light, and serial photos were taken of the protoplasts with green fluorescence using confocal microscopy. The pictures clearly demonstrate that that the fusion product comprising the wild-type protein ('pCambia-GFP-Xcv-1CaFO') occurs as islands (lipid rafts) in the plasma membrane of the cells, but the mutant protein carrying the double leucine deletion ('pCambia-GFP-xcv-1 CaT1') does not form such islands and shows homogeneous distribution in the plasma membrane.

Example 9

Identification of Genes Homologous to the Xcv-1 Gene in Plants and Animals

Complete or partial nucleotide sequences of the genomes of several viruses, bacteria, fungi and animals were determined in the framework of various genome projects. In most cases, the determination of the DNA sequences did not involve the identification of the function of a given segment; thus, the function of the sequences remains unknown. In relation to the Xcv-1 gene, data bank searches revealed that several sequences encoding proteins with similar structures to the xcv-1 protein can be found in the data banks (Feng et al., Mol Biol Rep DOI 10.1007/s11033-010-0419-1, 2010; Lieber et al., Current Biology 21: 1009-1017, 2011; Li et al., Biotechnol. Lett 31:905-910, 2009; Venancio T. M. and Aravind L. Bioinformatics 26:149-152, 2010). Alignment of the amino acid sequences of these proteins clearly demonstrated their structural similarity. In most cases, the region immersed in the membrane is delimited by a negatively charged amino acid (aspartic acid or glutamic acid) or a polar amino acid (asparagine). Alignment of a part of the CYSTM proteins is shown in Venancio T. M. and Aravind L., Bioinformatics 26:149-152, 2010. For the purposes of the invention, "proteins homologous to the Xcv-1 protein" refer to protein variants which contain at least 53% identical amino acids at their C-termini with respect to the last 15 amino acids of the C-terminus of the Xcv-1 protein (CLAALCCCCLLDACF).

Example 10

Induction of Resistance to *Xanthomonas euvesicatoria* in Tomato by the amiRNA Technique One of the most dangerous bacterial pathogens of tomato is *Xanthomonas euvesicatoria* (Xe), i.e., the same bacterium which also causes severe damage to pepper. Unlike pepper, tomato has not developed appropriate natural resistance, which would ensure acceptable protection. The bs4 gene identified in tomato does not provide sufficient protection, and therefore, tomato production is still highly threatened by Xe infection (Hutton et al., Theor. Appl. Genet. 121:1275-87, 2010). It was assumed that the xcv-1 gene identified in pepper could also provide resistance to Xe infection in tomato if the genes homologous to the Xcv-1 gene, i.e., genes SlXcv-1A and SlXcv-1B represented by SEQ ID NO:49 and SEQ ID NO:51, respectively, are inactivated in the tomato genome, and the inactivation is preceded by ensuring the functioning of the tomato genes homologous to the xcv-1 gene, i.e., genes Slxcv-1A and Slxcv-1B represented by a SEQ ID NO:59 and SEQ ID NO:66, respectively (see below). This strategy can be implemented in more than one ways including but not limited to:
1. Tomato is transformed with functional Slxcv-1A and Slxcv-1B genes followed by inactivating the resident genes SlXcv-1A and SlXcv-1B using the "amiRNA" technique.
2. Tomato is transformed with functional Slxcv-1A and Slxcv-1B genes followed by inactivating the resident genes SlXcv-1A and SlXcv-1B using the ZFN nuclease technique.
3. Tomato is transformed with functional Slxcv-1A and Slxcv-1B genes followed by identifying mutations—that inactivated SlXcv-1A and SlXcv-1B—using the TILLING or another similar technique, upon or without mutagenesis.
4. Tomato is transformed with functional Slxcv-1A and/or Slxcv-1B genes followed by inactivating the resident genes SlXcv-1A and SlXcv-1B present there using the TALEN technique.
5. Tomato is transformed with functional Slxcv-1A and/or Slxcv-1B genes followed by inactivating the resident genes SlXcv-1A and SlXcv-1B present there using the CRISPR/Cas technique.

A common feature of the above five strategies is the in vitro preparation of the Slxcv-1A and Slxcv-1B sequences and transformation into tomato in the first step. Since the functioning of the Slxcv-1A and Slxcv-1B genes is recessive in comparison with the wild-type genes, the second step involves inactivating the wild-type genes (SlXcv-1A and SlXcv-1B) with suitable methods—including but not limited to the above-listed three methods—in order to manifest the above functions.

Example 10A

Generation of Slxcv-1A and Slxcv-1B Sequences with Double Leucine Deletion

The preparation of the genes comprising the double leucine deletion (Slxcv-1A and Slxcv-1B) involved PCR amplification, cloning of the amplificates into pGemT-Easy vectors, and additional restriction digestions and reclonings—steps well-known to those skilled in genetic engineering. For the cloning, the sequences of two tomato genes, i.e., SlXcv-1A and SlXcv-1B, obtained from data banks were used. The sequences of genes SlXcv-1A and SlXcv-1B are SEQ ID NO:49 and SEQ ID NO:51, respectively.

Preparation of the Slxcv-1A Construct:
a PCR amplification was performed in the presence of a genomic DNA template from tomato using primers 'SlProm1AF3' (SEQ ID NO:53) and 'SlProm1AR3' (SEQ ID NO:54), and the 1074-bp DNA fragment was cloned into pGEM-T Easy vectors. The resulting plasmid ('p1A1') was digested with the enzyme NsiI followed by ligation and transformation to generate plasmid 'p1A2'. A PCR amplification was performed in the presence of a genomic DNA template from tomato using primers 'SlTerm1AF3' (SEQ ID NO:55) and 'SlTerm1AR3' (SEQ ID NO:56), and the 283-bp DNA fragment was cloned into pGEM-T Easy vectors to generate plasmid 'p1A3'. The 'p1A2' plasmid was digested with NsiI, and the 'p1A3' plasmid was digested with NsiI and PstI; next, the two mixtures were combined and ligated, and—upon transformation—plasmid 'p1A4', in which the NsiI end of 'p1A3' is positioned towards the genomic sequence in 'p1A2', was identified. A PCR amplification on tomato genomic DNA was performed using primers 'SlMid1AF1' (SEQ ID NO:57) and 'SlMid1ABR1' (SEQ ID NO:58), and the 1137-bp DNA fragment was cloned into pGEM-T Easy vectors to generate plasmid 'p1A5'. Upon mixing 'p1A4' and 'p1A5', the plasmids were digested with NsiI and ligated, and—upon transformation—plasmid 'p1A6', in which the 1094-bp NsiI fragment was cloned into the NsiI site of the 'p1A4' plasmid in the correct orientation, was identified. Finally, this resulted in construct Slxcv-1A (SEQ ID NO:59), which encodes the Slxcv-1A protein (SEQ ID NO:60), a variant with the double leucine deletion.

Preparation of the Slxcv-1B Construct:

A PCR amplification was performed in the presence of a genomic DNA template from tomato using primers 'SlProm1BF3' (SEQ ID NO:61) and 'SlProm1BR3' (SEQ ID NO:62), and the 1450-bp DNA fragment was cloned into pGEM-T Easy vectors. The resulting plasmid ('p1B1') was digested with the enzyme NsiI followed by ligation and transformation to generate plasmid 'p1B2'. A PCR amplification was performed in the presence of a genomic DNA template from tomato using primers 'SlTerm1 BF3' (SEQ ID NO:63) and 'SlTerm1BR3' (SEQ ID NO:64), and the 787-bp DNA fragment was cloned into pGEM-T Easy vectors to generate plasmid 'p1B3'. The 'p1B2' plasmid was digested with NsiI, and the 'p1B3' plasmid was digested with NsiI and PstI; next, the two mixtures were combined and ligated, and—upon transformation—plasmid 'p1B4', in which the NsiI end of 'p1B3' is positioned towards the genomic sequence in 'p1B2', was identified. A PCR amplification on tomato genomic DNA was performed using primers 'SlMid1BF1' (SEQ ID NO:65) and 'SlMid1ABR1' (SEQ ID NO:58), and the 1273-bp DNA fragment was cloned into pGEM-T Easy vectors to generate plasmid 'p1B5'. The 'p1B4' plasmid was digested with NsiI but the 'p1B5' plasmid was only partially digested with NsiI; next, the two samples were combined and ligated, and—upon transformation—plasmid 'p1B6', in which the 1236-bp fragment was cloned into the NsiI site of the 'p1B4' plasmid in the correct orientation, was identified. Finally, this resulted in construct Slxcv-1B (see SEQ ID NO:66), which encodes the Slxcv-1B protein (SEQ ID NO:67), a variant with the double leucine deletion.

Upon preparing the two constructs, the Slxcv-1A and Slxcv-1B sequences were cloned head to head into an *A. tumefaciens* vector pCAMBIA2300 cut by XbaI from the pGemT-Easy vector using NotI-SpeI, and were transformed into *E. coli*. The resulting plasmid was designated 'pDSlxcv-1AB'. From the *E. coli* host, the plasmid was introduced into the *A. tumefaciens* strain using triparental mating. The resulting strains were designated *A. tumefaciens* (pDSlxcv-1AB).

Example 10B

Transformation of the Slxcv-1A and Slxcv-1B Genes into Tomato Using *Agrobacterium tumefaciens*

*A. tumefaciens* transformation was carried out as follows: Tomato seeds were immersed in 70% ethanol for 1 minute, and were then transferred into a solution of 5.25% sodium perchlorate (NaClO) and 0.1% Tween 20 and shaken for 30 minutes. Next, the seeds were rinsed with distilled water 8 times and transferred to Petri dishes containing medium A, and were grown for 8 days at 25° C. with 16-hour light cycle. The cotyledons of the plants were cut at the apex and at the base, pricked, placed on medium B, and overlaid with MSO liquid medium containing *A. tumefaciens* (pDSlxcv-1AB). The MSO liquid medium containing *A. tumefaciens* (pDSlxcv-1AB) was prepared as follows: the *A. tumefaciens* (pDSlxcv-1AB) strain stored at −80° C. (prepared as described in Example 11A) was plated onto a medium containing YEP+100 μg/ml rifampicin and incubated at 30° C. One of the colonies was inoculated into 3 ml YEP liquid medium (in a 20-ml test tube) using an inoculation loop, and the bacteria were rotated in a roller to ensure aeration and cultured until reaching the stationary phase (24 hours). The bacteria were collected by centrifugation as previously described, the supernatants were discarded and the cells were suspended in 12 ml MSO liquid medium. The leaves were treated with the *Agrobacterium* suspension for 20 minutes, then the excess suspension was drawn off and the leaves were co-cultivated with the bacteria for 48 hours. After two days, the leaves were transferred to plates with medium C. The plants were transferred to fresh plates with medium C at two-week intervals. The developing calluses could be cut to smaller pieces, and were transferred to plates with medium D and then to fresh plates at two-week intervals. When the small growths appeared, they were transferred again to plates with medium D. When reaching a length of 2 to 4 cm, the growths were transferred to fresh plates with medium E, and they started to form roots. Plants of 5 cm could already be planted into potting soil. A total of 15 independent T0 transformant plants (T0/xcv1 to 15) were grown.

MSO medium (1000 ml): 4.3 g MS salts, 100 mg myo-inositol, 0.4 ml (1 mg/ml) thiamine-HCl, 20 g saccharose YEP medium (1000 ml): 10 g yeast extract, 10 g peptone, 5 g NaCl (pH adjusted to 7 with NaOH)

Vitamin solution (per 1000 ml): 50 mg thiamine-HCl, 200 mg glycine, 500 mg nicotine aid, 50 mg pyridoxine-HCl, 50 mg folic acid, 5 mg biotin, 10 g myo-inositol

| Substance/medium | A | B | C | D | E | (per 1000 ml) |
|---|---|---|---|---|---|---|
| MS (Gibco) | 4.3 | 4.3 | 4.3 | 4.3 | 2.15 | g |
| Saccharose | 15 | 30 | 30 | 15 | 15 | g |
| Vitamin solution | 1 | 1 | 1 | 1 | 1 | ml |
| NAA | — | 2 | — | — | — | ml |
| BAP | — | 2 | — | — | — | ml |
| Zeatin | — | — | 2 | — | — | mg |
| IAA | — | — | — | — | 5 | mg |
| GA | — | — | 1 | — | — | mg |
| Km | — | — | 100 | 100 | 50 | mg |
| Timentin | — | — | 300 | 300 | 300 | mg |
| Agar | — | — | — | — | 5 | g |

(BAP = Benzyl-Aminopurine, NAA = Naphthalene Acetic Acid), IAA = Indol Acetic Acid, GA = Gibberelic Acid, Km = kanamycin)

When the stems and roots of the T0/xcv1-15 transgenic plants were strong enough, DNA was isolated from the leaves, and a PCR reaction was performed to detect the transformation events using the following primer pairs:
1. Pr_Sl SlMid1AF1 primer (SEQ ID NO:57);
   Pr_SlTerm1AR3 primer (SEQ ID NO:56);
   length of the expected amplificate: 1400 bp;
2. Pr_SlTerm1BF3 primer (SEQ ID NO:62);
   Pr_SlTerm1BR3 primer (SEQ ID NO:63);
   length of the expected amplificate: 787 bp.

The transgene sequence between the primers used for the amplification could be detected in all cases.

Example 10C

Generation of the Gene Encoding the Prim-amiRNA Designated as Pri_SlXe1-amiRNA

The microRNAs (miRNAs) discovered in eukaryotic organisms inhibit the efficient expression of the corresponding genes. This gene inactivation allows for an alternative form of gene regulation through a specific mechanism resulting in the inhibition of the function of the gene, which is of great importance in terms of development and differentiation (Kidner C. A. és Martienssen R. A., Curr. Opin.

Plant Biol. 8:38-44, 2005). miRNAs are ribonucleic acid molecules present in eukaryotic cells. The miRNAs are short molecules consisting of 21 to 24 nucleotides in contrast to the long RNA molecules fulfilling other functions (e.g., mRNA, ribosomal RNA). The miRNAs are post-transcriptional inhibitors of the functioning of mRNAs by physically inhibiting protein synthesis on complementary mRNAs, or by causing the degradation of complementary mRNAs upon binding to them (Bartel D. P., Cell 16:281-297, 2004).

Studies of the miRNAs and exploration of the biochemical processes on the molecular level made it possible to extend this specific inhibition mechanism to genes for which no natural miRNAs exist. Artificially prepared gene-specific miRNAs were designated amiRNAs (artificial miRNA) (Ossowski et al., Plant J. 53:674-690, 2008; Park et al., Plant Cell Rep. 28:469-480, 2009; Schwab et al., Methods Mol. Biol. 592:71, 2010; Sablok et al., Biochem. and Biophys. Res. Comm. 406:315-319, 2011). The amiRNA-based gene inactivation has been generated in a number of animal and plant systems (Schwab et al, Plant Cell 18:1121-1133, 2006), and in general terms, the target mRNAs can be inactivated, thereby eliminating the gene function in question, through carefully designed experiments.

An amiRNA gene coding for an amiRNA ribonucleotide consist of the following sequences: promoter, 5' stem extension, amiRNA*, loop region, the amiRNA and a 3' stem extension with polyA tail (Schwab et al., Methods Mol. Biol. 592:71, 2010).

Strategic Course of Inducing Resistance in Tomato Plants:

During the PCR amplification and sequencing of the tomato genomic DNA, two sequences homologous to the Xcv-1 gene of pepper (SlXcv-1A and SlXcv-1B) were identified: the nucleotide sequences and the deduced amino acid sequences are shown in the DNA sequences of SEQ ID NO:49 and SEQ ID NO:51, respectively, and the amino acid sequences of SEQ ID NO:50 and SEQ ID NO:52, respectively.

The target mRNA sequence—with which the amiRNA designated 'SlXe1-amiRNS' will show partial complementarity (18 of 21 bases)—is the segment which precedes the stop codon of genes SlXcv-1A and SlXcv-1B and encodes the two leucines corresponding to the Xcv-1 gene (see FIG. 3). The SlXe1-amiRNA will not be complementary to the mRNAs of the genes comprising the double leucine deletion to be simultaneously expressed, and therefore will not inactivate them. The SlXe1-amiRNA (SEQ ID NO:74) is expressed with the help of pre-sly-MIR159miRNSpre-miDNA (SEQ ID NO:68), which is responsible for the expression of sly-MIR159 (Accession No. MI0009974) in tomato, and transcription generates preSlpre-slyM1159RNA (SEQ ID NO:69).

The coding segment of the pre-SlXe1-amiRNA (SEQ ID NO:73) sequence, i.e., the pre-SlXe1-amiDNA (SEQ ID NO:72) is prepared as follows. Amplification is carried out from tomato genomic DNA using the synthesised primers 'Pri_SlXe1pre-amiRNA' (SEQ ID NO:70) and 'Pr2_SlXe1pre-amiRNA' (SEQ ID NO:71), and the resulting double-stranded pre-SlXe1-amiDNA (SEQ ID NO:72) coding sequence is cloned into pGemT-Easy vectors, and—upon restriction by EcoRI-SpeI—pKSS vectors, and finally into pC61H vectors through KpnI and XbaI cleavage, as described in Example 3. The HindIII-EcorRI fragment of pCK61H was generated by cloning the EcoRI-HindIII fragment of BIN61S (Silhavy D. et al., EMBO J. 21:3070-3080, 2002) carrying the 35S promoter, polilinker and terminator sequences into the EcoRI-HindIII site of the pCAM-BIA1300. The resulting plasmid was designated pC61H-pri-SlXe1-amiRNA and the strain containing the plasmid was designated A. tumefaciens (pC61H-pri-SlXe1-amiRNA). The HindIII-EcorRI fragment of pCK61H-SlXe1-amiRNA carrying the gene encoding SlXe1-ami RNA is shown in SEQ ID NO:92

Example 10D

Transformation of Pri-SlXe1-amiRNS Sequences into T0/1-15 Transgenic Plants Containing the Genes Slxcv-1A and Slxcv-1B The transformation with A. tumefaciens was carried out as described in Example 10B, but the plants to be transformed were the T0/1-15 transgenic plants, the A. tumefaciens (pC61K-pri-SlXe1-amiRNA) strain was used for the transformation and the selection was for hygromycin. At the end of the transformation, seven independent plants (T0/ami1 to 7) were grown.

Pr1_SlXe1 pre-amiRNA (SEQ ID NO:70);
Pr2_SlXe1 pre-amiRNA (SEQ ID NO:71);
length of the expected amplificate: 178 bp.

In addition to DNA isolation, total RNA was isolated from the leaves of the control and transgenic plants using the RNeasy Mini Kit, and the total RNA was run on a 12% carbamide/acrylamide gel, transferred to a Hybond NX membrane (GE Healthcare Amersham) and hybridised with an alpha-$^{32}$ATP-labelled LNA probe encoding the SlXe1-amiRNA. The autoradiogram obtained upon the hybridisation and the image of the total RNA loaded to the gel are shown in FIG. 4.

The transformant plants were grown until the 8-leaved stage, infected with the bacterium Xanthomonas euvesicatoria, and evaluated as described in Example 1. The results of the Xanthomonas euvesicatoria infection are summarised in Table 2.

TABLE 2

Detection of transgenes from transgenic and control plants after a PCR reaction using specific primer pairs, and plant phenotypes after infection with Xanthomonas euvesicatoria

| Plant identifier | Appearance of amplificate 1137 | Appearance of amplificate 1273 | Appearance of the 178-bp amplificate | Phenotype after infection with Xanthomonas euvesicatoria (Xe) |
|---|---|---|---|---|
| C1 | no | no | no | Symptoms of Xe infection, tissue necrosis |
| C2 | no | no | no | Symptoms of Xe infection, tissue necrosis |
| C3 | no | no | no | Symptoms of Xe infection, tissue necrosis |
| T1 | yes | yes | yes | healthy phenotype tissue oedema only |
| T2 | yes | yes | yes | transitional phenotype slight tissue necrosis |
| T3 | yes | yes | yes | healthy phenotype tissue oedema only |
| T4 | yes | yes | yes | healthy phenotype tissue oedema only |
| T5 | yes | yes | yes | transitional phenotype slight tissue necrosis |
| T6 | yes | yes | yes | healthy phenotype tissue oedema only |
| T7 | yes | yes | yes | healthy phenotype tissue oedema only |

Example 11

Induction of Resistance to *Xanthomonas euvesicatoria* in Tomato Using the Engineered Nuclease Technique In a certain prior reverse genetic approach, a plant was first mutagenised, and then the mutation was identified in the gene sought. In most cases, the mutation was identified using T_DNA and transposon insertion mutagenesis, and TILLING (Targeted Induced Local Lesions in Genomes) (Feldman, K. A. The Plant Journal 1:71-82, 1991; McCallum, C. M. et al., Nat. Biotech. 18455-457, 2000). However, this approach was troublesome, time-consuming and uncertain. The RNA interference (RNAi) and artificial microRNA (amiRNA) techniques mentioned in Example 10 are already specific to the desired gene, however, the expression of the gene is often impossible to eliminate completely, that is, null phenotype should be obtained by all means (Schwab et al, Plant Cell 18:1121-1133, 2006). Consequently, methods resulting in genes that are completely knocked out and thus guaranteeing a null phenotype are of vital importance. By now, three methods satisfying the above criteria have been disclosed. These are the above-mentioned ZFN, TALEN and CRISPR/Cas nuclease techniques, which generate gene specific c double stranded cuts in the DNA and following the activity of the repair mechanism of the cells insertions and deletions with the size of one to several tens of base pairs or more in a gene-specific manner [Urnov F. D. et al. Nat Rev Genet. 11:636-46, 2010; Carroll D. Genetics. 188:773-82, 2011; Christian M. et al., Genetics 189:757-761, 2010; Cermak, T. et al., Nucl. Acids Res. 39: e82, 2011; Mussolino C. et al., Nucleic Acids Res. 39:9283-9293, 2011; Miller J. C. et al., Nat. Biotechnol. 29:143-148, 2011; Christian M. et al., G3 (Genes, Genomes, Genetics, Bethesda), doi:10.1534/g3.113.007104, 2013; Cho S. W. et al., Nat Biotechnol. 31:230-232, 2013; Cong L. et al., Science 339:819-823, 2013; Mali P. et al., Science 339:823-826, 2013]. For the purpose of generating the 6-bp deletion in the tomato genes SlXcv-1A and SlXcv-1B, the TALEN, CRISPR/Cas nuclease and the ZFN technique can be equally used. From tomato cells only producing the double leucine deletion proteins Slxcv-1A and/or Slxcv-1B, Xe resistant tomato plants can be generated in the same way as in Example 10.

Example 11A

Induction of Resistance to *Xanthomonas euvesicatoria* in Tomato Using the TALEN Technique The TALEN target sequence to which the TALEN pairs recognize (SlXcv-1AB_TALEN-L, SlXcv-1A_TALEN-R and SlXcv-1B_TALEN-R) should be selected and determined in view of the fact that the 6 bp deletions should located at positions 2277 to 2282 and 2640 to 2645, respectively. Since the applied TALEN nucleases quite often cut within the so-called "spacer" sequences, it is reasonable to chose a size of 18 base pairs for the spacer region, and to chose a TALEN target sequence extending into 17 and 17 base pairs both to the right and to the left in a manner ensuring that the target sequences are preceded by a T/A base pair in all cases [Cermak, T. et al., Nucl. Acids Res. 39:e82, 2011; Christian M. et al., G3 (Genes, Genomes, Genetics, Bethesda)]. Since the sequences of the two genes to the left side of the mutation are identical along an at least 36-bp segment from the left end of the desired deletion, the same left TALEN target sequence should be chosen for both genes (SlXcv-1AB_TAL-L, see SEQ ID NO:75 and FIG. 5). Counting from the right side of the desired deletion, differences between the two genes occur already after the 15th base, and therefore, the right TALEN target sequences will be different for SlXcv-1A and SlXcv-1B (SlXcv-1A_TAL-R, see SEQ ID NO:76; and SlXcv-1B_TAL-R, see SEQ ID NO:77 and FIG. 5). Each base of the target sequences are recognised by "repeat-variable di-residues" (RVDs in short)—that is, doublets of adjacent amino acids—present in the TAL effector proteins. The following RVD amino acids can be designed for each base: A is recognised by the NI amino acid doublet, C is recognised by the HD doublet, G is recognised by the NH doublet, and T is recognised by the NG doublet (A=adenosine, C=cytidine, G=guanosine, T=thymidine, NI=asparagine-isoleucine, HD=histidine-aspartic acid, NH=asparagine-histidine, NG=asparagine-glycine; see FIG. 5). The RVD sequences and the bordering repeat sequences can be synthesised and cloned in accordance with the relevant literature (pNI1-10, pHD1-10, pNH1-10, and pNG1-10, see Cermak, T. et al., Nucl. Acids Res. 39: e82, 2011, supplementary material). The sequences of the pNH series are identical with the pNN sequences except that the AAC CAT codon doublet, which encodes asparagine and histidine, should be used instead of the double asparagine codon (AAC AAT). The repeats containing RVDs can be cloned into plasmids pFUS_A and pFUS_B6 after BsaI cutting. Plasmids pFUS_A, pFUS_B6 and pLR-NG and pLR-NI, respectively, can be cut by Esp3I and cloned into the Esp3I site of pTAL3. (Cermak, T. et al., Nucl. Acids Res. 39: e82, 2011). Concerning the SlXcv-1A and the SlXcv-1B genes, specific TALEN sequences comprising of TAL-N', SlXcv-1A, and SlXcv-1B specific TAL sequences containing the 17 repeats and RVDs (SlXcv-1AB_TAL-L, SlXcv-1A_TAL-R and SlXcv-1B_TAL-R), the TAL-C in which the NLS sequence is present, and finally the catalitic domain of the FokI nuclease. These sequences (TALEN-L és TALEN_R, see FIG. 6.) can be reclonded, first the FokI domain on a SacI (the end are made blunt ended) BamHI fragment is cloned into the BamHI-MlyI site of BIN61S vector (Silhavy D. et al., EMBO J. 21:3070-3080, 2002), then this derivative is cut by BamHI and the SlXcv-1AB_TALEN-, (SEQ ID NO:78), SlXcv-1A_TALEN-R (SEQ ID NO:79), and SlXcv-1B_TALEN-, (SEQ ID NO:80) sequences, respectively are cloned in pairs (see FIG. 6.) on a HindIII-EcoRI fragment into the EcoRI site of pCAMBIA1300 and/or pCAMBIA2300.—followed by introducing into *Agrobacterium tumefaciens* by transformation, and finally transformed into suitable tomato plants as described in Example 10. The tomato species should be selected in a manner ensuring the functional expression of the TALEN gene. FIG. 6 shows the functional map of the sequences between the left border (LB) and right border (RB) sequences in the vectors used for transformation. Transformation should be performed with the four vectors shown in FIG. 6 (SlXcv-1_TALEN 1AH, SlXcv-1_TALEN 1BH, SlXcv-1_TALEN 1AK, SlXcv-1_TALEN 1BK), and hygromycin and kanamycin resistant calluses should be selected and regenerated in the presence of hygromycin (50 µg/ml) and kanamycin (100 µg/ml). The SlXcv-1A and SlXcv-1B genes can be detected from the calluses using PCR between bases 2277 to 2282 and 2640 to 2645, respectively (see FIGS. 5 and 7). The Slxcv-1A and Slxcv-1B genotypes carrying the 6-bp deletion, as well as other deletion/insertion derivatives can be identified in both selections. Plants are regenerated from the Slxcv-1A and Slxcv-1B calluses, and the hygromycin resistant plants—which carry the Slxcv-1A gene—are transformed with the SlXcv-1_TALEN 1 BK vector, and the kanamycin resistant plants—which carry the Slxcv-1B gene—are transformed with the SlXcv-1_TALEN 1AH vector, and we proceed as described above, that is, kanamycin and hygromycin resistant calluses are grown, and PCR techniques are used to identify the deletions in the Slxcv-1B and Slxcv-1A genes. During the genotyping of the resistant calluses, deletions are sought between base pairs 2277 to 2282 and 2640 to 2645. Three of the deletions thus identifiable are mentioned below.

In Variant 1, the desired 6-bp deletion is present in both genes; thus, these plants carry the genes Slxcv-1A and Slxcv-1B, which encode the Slxcv-1A (SEQ ID NO:60) and the Slxcv-1B (SEQ ID NO:67) amino acid sequences (see FIG. 7), respectively.

In Variant 2, the plants carry the Slxcv-1A gene, which encodes the Slxcv-1A (SEQ ID NO:60) amino acid sequence. In Variant 2, the derivative of the SlXcv-1B gene contains a deletion/insertion which changes the open reading frame (out of frame deletion) (see FIG. 7).

In Variant 3, the plants carry the Slxcv-1B gene, which encodes the Slxcv-1B (SEQ ID NO:67) amino acid sequence. In Variant 3, the derivative of the SlXcv-1A gene contains a deletion/insertion which changes the open reading frame (out of frame deletion) consequently the gene is inactivated (see FIG. 7).

The above three transformant derivatives (Variants 1, 2 and 3) can be vegetatively propagated and grown to the 8-leaved stage, then infected with *Xanthomonas euvesicatoria*, and the products resistant to *Xanthomonas euvesicatoria* can be selected. For a skilled person, it is obvious that the transgenes (T-DNAs) can be removed from the genome of the selected plants resistant to *Xanthomonas euvesicatoria* by crossing, because the transgenes will be segregated from a part of the progeny, that is, non-transgenic plants can be generated from them.

Example 11B

Induction of Resistance to *Xanthomonas euvesicatoria* in Tomato Using the CRISPR/Cas Nuclease Technique The above-described CRISPR/Cas technology (Cho S. W. et al., Nat. Biotechnol. 31:230-232, 2013; Cong L. et al., Science 339:819-823, 2013; Mali P. et al., Science 339:823-826, 2013; Feng Z. et al., Cell Research: 1-4, 2013) is also useful for generating the desired 6-bp deletion(s), or gene mutations resulting in null phenotypes, in tomato and in other plants. In the first case, 'single guide RNAs' (sgRNAs in short) were designed for the wild-type tomato sequences corresponding to the desired 6-bp deletion (see FIG. 5A) as target sequence. The procedure is as follows: after reannealing, the oligonucleotides (sgRNA_SlXcv-1F, 5'-GATTTCTGTGCTGTTGCTGTCTCT, SEQ ID NO:82 and sgRNA_SlXcv-1R, 5'-AAACAGACACGACAACGACAGAGA, SEQ ID NO:83) designed and synthesised for the 20-bp target sequence (CRISPR_SlXcv-1, 5'-TCTGTGCTGTTGCTGTCTCT, see SEQ ID NO:81) are cloned into a BsaI/BsaI site of a suitable vector after the tomato-specific U6 promoter and before the sgRNA sequence. This construct is followed by a double 35S promoter, an NLS sequence, the hspCAS9 gene (Feng Z. et al., Cell Research:1-4, 2013), another NLS sequence and the NOS terminator (Cong L., et al. Science 339:819-823, 2013). The resulting construct is cloned into pCAMBIA plant-derived transformation vectors carrying a hygromycin and a kanamycin resistance gene, respectively (see above), and is used to transform tomato cells. It is important to note, that the CRISPR_SlXcv-1 (SEQ ID NO:81) sequence may not target and cut Slxcv-1A or Slxcv-1B sequences containing the 6 bp deletion.

Upon preparing the vectors, the tomato cells are transformed as described in Example 10, the hygromycin and kanamycin resistant calluses are selected as described in Example 11, and the gene derivatives of SlXcv-1A and SlXcv-1B are evaluated as described in Example 11. As a result of the experiments and tests, similar results are expected as in the case of the three variants described in Example 11, that is, the desired 6-bp deletion is present in both SlXcv-1 genes (SlXcv-1A and SlXcv-1B), which encode the Slxcv-1A (SEQ ID NO:60) and Slxcv-1B (SEQ ID NO:67) amino acid sequences, respectively; or the desired 6-bp deletion is only present in SlXcv-1A and SlXcv-1B, and early stop codon, or an out of frame deletion/insertion giving null phenotype is generated in the other gene.

Upon treatment with the CRISPR/Cas nuclease, the transformant derivatives having the advantageous feature (Variants 1, 2 and 3, see Example 11A.) can be vegetatively propagated and grown to the 8-leaved stage, then infected with *Xanthomonas euvesicatoria*, and the progeny resistant to *Xanthomonas euvesicatoria* can be selected. For a skilled person, it is obvious that—in this case too—the transgenes (T-DNAs) can be removed from the genome of the selected plants resistant to *Xanthomonas euvesicatoria* by crossing, because the transgenes will be segregated from a part of the progeny, that is, non-transgenic plants can be generated from them.

Example 11C

Induction of Resistance to *Xanthomonas euvesicatoria* in Tomato Using the ZFN Technique The above-mentioned ZFN technology (Urnov F. D. et al. Nat Rev Genet. 11:636-46, 2010, Carroll D. Genetics. 188:773-82, 2011) is also useful for generating the desired 6-bp deletion(s), or gene mutations resulting in null phenotypes, in tomato and in other plants. In case of generating the desired 6-bp deletion, the procedure is as follows: the target sequences to be recognised by the two zinc finger (ZF) proteins are selected within the segment from bases 2253 to 2306 (SEQ ID NO:84) of the SlXcv-1A gene sequence (SEQ ID NO:49) and within the segment from bases 2616 to 2669 (SEQ ID NO:85) of the SlXcv-1B gene sequence (SEQ ID NO:51)—as shown in FIG. 5—in a manner ensuring a distance of 5 to 7 bp from each other. It is obvious that more than one arrangements can be selected as the target sequence along the above the DNA segments (SEQ ID NO:84, SEQ ID NO:85) and the specific ZF proteins consisting of ZF domains, which are specific to the left and right side of the target sequences. Possible examples for the SlXcv-1A gene (SEQ ID NO:49) and SlXcv-1B gene (SEQ ID NO:51) include but are not limited to 6-bp target sequences exactly covering the sequences of the desired 6-bp deletion in the above two genes. In both cases, the target sequence is 5'-CTCTTG, which encodes two leucines, and the target sequences of the left and right specific ZF proteins [5'-TGTGCTGTTGCT (SEQ ID NO:86) and 5'-TTTCGTACGTAG (SEQ ID NO:87), respectively] are identical in both genes because they show 100% identity in this region. The genes of the ZF proteins recognising the specific left and right target sequences are cloned into pCAMBIA plant-derived transformation vectors carrying a hygromycin and a kanamycin resistance gene, respectively (see above), and are used to transform tomato cells.

Upon preparing the vectors, the tomato cells are transformed as described in Example 10, and the procedures described in Examples 11A and 11B are followed thereafter.

The deletion/insertion procedure using the ZNF, TALEN and CRIPSR/Cas nucleases can be performed in the transgenic tomato plants carrying one of the genes (i.e., either Slxcv-1A or Slxcv-1B), or both (Slxcv-1A and Slxcv-1B), wherein knock-out insertion or deletion derivatives are sought in the resident genes SlXcv-1A and SlXcv-1B among the plants treated with the ZFN, TALEN or CRIPSR/Cas nucleases. In fortunate cases, the double null allele variant can also be obtained after performing the transformation, and the second transformation is unnecessary.

For the skilled person, it is obvious and understandable that knock-out null mutants in the SlXcv-1A and SlXcv-1B genes may not only be generated within the segment from bases 2244 to 2318 (SEQ ID NO:84) of the SlXcv-1A gene sequence (SEQ ID NO:49) and within the segment from bases 2607 to 2681 (SEQ ID NO:85) of the SlXcv-1B gene sequence (SEQ ID NO:51)—as shown in FIG. 5—with the above-mentioned techniques (TALEN and CRIPSR/Cas nuclease and ZFN) and other mutagenesis techniques (mutagenesis, ECOTILLING, Comai L. et al., Plant J. 37:778-786, 2004 etc.), but they can also be designed for the entire sequence of SlXcv-1A (SEQ ID NO:49) and SlXcv-1B (SEQ ID NO:51), that is, for all those sequences that are responsible for the expression and manifestation of the above genes and their products (functional proteins) (e.g., the promoter, the 3' and 5' UTR, exon, intron etc. sequences).

```

The invention claimed is:

1. A nucleic acid molecule that is capable of conferring to a plant resistance to *Xanthomonas euvesicatoria*, wherein the nucleic acid molecule comprises a nucleotide sequence selected from the group consisting of:
  (a) a non-naturally occurring nucleotide sequence comprising at least 95% sequence identity to at least one of the nucleotide sequences set forth in SEQ ID NO:37, 59, and 66, wherein the nucleic acid molecule encodes a CYSTM protein comprising a deletion of two amino acids at the locations corresponding to positions 87 and 88 of the amino acid sequence set forth in SEQ ID NO: 42;
  (b) the nucleotide sequence set forth in SEQ ID NO:88, 89, or 90;
  (c) a nucleotide sequence comprising at least 95% sequence identity to at least one of the nucleotide sequences set forth in SEQ ID NOS:88, 89, and 90, wherein the nucleic acid molecule encodes a CYSTM protein comprising a deletion of two amino acids at the locations corresponding to positions 87 and 88 of the amino acid sequence set forth in SEQ ID NO: 42;
  (d) a nucleotide sequence encoding an artificial protein comprising at least 95% sequence identity to the amino acid sequence set forth in SEQ ID NO:42, wherein the artificial protein is a CYSTM protein comprising a deletion of two amino acids at the locations corresponding to positions 87 and 88 of the amino acid sequence set forth in SEQ ID NO: 42; and
  (e) a nucleotide sequence encoding an artificial protein comprising at least 95% sequence identity to the amino acid sequence set forth in SEQ ID NO:38, 60, or 67, wherein the artificial protein is a CYSTM protein comprising a deletion of two amino acids at the locations corresponding to positions 87 and 88 of the amino acid sequence set forth in SEQ ID NO: 42.

2. An artificial xcv-1 CYSTM protein that is capable of conferring to a plant resistance to *Xanthomonas euvesicatoria*, wherein the artificial xcv-1 CYSTM protein is encoded by a nucleic acid molecule that is capable of conferring to a plant resistance to *Xanthomonas euvesicatoria*, wherein the nucleic acid molecule comprises a nucleotide sequence selected from the group consisting of:
  (a) a non-naturally occurring nucleotide sequence comprising at least 95% sequence identity to at least one of the nucleotide sequences set forth in SEQ ID NO:37, 59, and 66, wherein the nucleic acid molecule encodes a CYSTM protein comprising a deletion of two amino acids at the locations corresponding to positions 87 and 88 of the amino acid sequence set forth in SEQ ID NO: 42;
  (b) the nucleotide sequence set forth in SEQ ID NO:88, 89, or 90;
  (c) a nucleotide sequence comprising at least 95% sequence identity to at least one of the nucleotide sequences set forth in SEQ ID NOS:88, 89, and 90, wherein the nucleic acid molecule encodes a CYSTM protein comprising a deletion of two amino acids at the locations corresponding to positions 87 and 88 of the amino acid sequence set forth in SEQ ID NO: 42:
  (d) a nucleotide sequence encoding an artificial protein comprising at least 95% sequence identity to the amino acid sequence set forth in SEQ ID NO:42, wherein the artificial protein is a CYSTM protein comprising a deletion of two amino acids at the locations corresponding to positions 87 and 88 of the amino acid sequence set forth in SEQ ID NO: 42; and
  (e) a nucleotide sequence encoding an artificial protein comprising at least 95% sequence identity to the amino acid sequence set forth in SEQ ID NO:38, 60, or 67, wherein the artificial protein is a CYSTM protein comprising a deletion of two amino acids at the locations corresponding to positions 87 and 88 of the amino acid sequence set forth in SEQ ID NO: 42.

3. A vector comprising the nucleic acid molecule according to claim 1.

4. A host cell transformed with a vector comprising a nucleic acid molecule that is capable of conferring to a plant resistance to *Xanthomonas euvesicatoria*, wherein the nucleic acid molecule comprises a nucleotide sequence selected from the group consisting of:
  (a) a non-naturally occurring nucleotide sequence comprising at least 95% sequence identity to at least one of the nucleotide sequences set forth in SEQ ID NO:37, 59, and 66, wherein the nucleic acid molecule encodes a CYSTM protein comprising a deletion of two amino acids at the locations corresponding to positions 87 and 88 of the amino acid sequence set forth in SEQ ID NO: 42;
  (b) the nucleotide sequence set forth in SEQ ID NO:88, 89, or 90;
  (c) a nucleotide sequence comprising at least 95% sequence identity to at least one of the nucleotide sequences set forth in SEQ ID NOS:88, 89, and 90, wherein the nucleic acid molecule encodes a CYSTM protein comprising a deletion of two amino acids at the locations corresponding to positions 87 and 88 of the amino acid sequence set forth in SEQ ID NO: 42;

(d) a nucleotide sequence encoding an artificial protein comprising at least 95% sequence identity to the amino acid sequence set forth in SEQ ID NO:42, wherein the artificial protein is a CYSTM protein comprising a deletion of two amino acids at the locations corresponding to positions 87 and 88 of the amino acid sequence set forth in SEQ ID NO: 42; and (e) a nucleotide sequence encoding an artificial protein comprising at least 95% sequence identity to the amino acid sequence set forth in SEQ ID NO:38, 60, or 67, wherein the artificial protein is a CYSTM protein comprising a deletion of two amino acids at the locations corresponding to positions 87 and 88 of the amino acid sequence set forth in SEQ ID NO: 42.

5. A tomato plant showing resistance to at least one *Xanthomonas euvesicatoria*, the tomato plant comprising a genome which is modified to contain a first modified CYSTM gene and a second modified CYSTM gene, wherein the first modified CYSTM gene comprises a nucleotide sequence selected from the group consisting of a) the nucleotide sequence set forth in SEQ ID NO: 59 or a nucleotide sequence comprising at least 95% identity to the nucleotide sequence set forth in SEQ ID NO: 59, wherein the first modified CYSTM gene is capable of conferring to a plant resistance to *Xanthomonas euvesicatoria* and encodes a protein comprising a deletion of two amino acids at the locations corresponding to positions 87 and 88 of the amino acid sequence set forth in SEQ ID NO: 42, and b) a nucleotide sequence encoding the amino acid sequence set forth in SEQ ID NO: 60; or a nucleotide sequence encoding an amino acid sequence comprising at least 95% identity to the amino acid sequence set forth in SEQ ID NO: 60, wherein the first modified CYSTM gene is capable of conferring to a plant resistance to *Xanthomonas euvesicatoria* and encodes a protein comprising a deletion of two amino acids at the locations corresponding to positions 87 and 88 of the amino acid sequence set forth in SEQ ID NO: 42;

wherein the second modified CYSTM gene comprises a nucleotide sequence selected from the group consisting of c) the nucleotide sequence set forth in SEQ ID NO: 66 or a nucleotide sequence comprising at least 95% identity to the nucleotide sequence set forth in SEQ ID NO: 66, wherein the second modified CYSTM gene is capable of conferring to a plant resistance to *Xanthomonas euvesicatoria* and encodes a protein comprising a deletion of two amino acids at the locations corresponding to positions 87 and 88 of the amino acid sequence set forth in SEQ ID NO: 42, and d) a nucleotide sequence encoding the amino acid sequence set forth in SEQ ID NO: 67 or a nucleotide sequence encoding an amino acid sequence comprising at least 95% identity to the amino acid sequence set forth in SEQ ID NO: 67, wherein the second modified CYSTM gene is capable of conferring to a plant resistance to *Xanthomonas euvesicatoria* and encodes a protein comprising a deletion of two amino acids at the locations corresponding to positions 87 and 88 of the amino acid sequence set forth in SEQ ID NO: 42.

6. A method for generating a plant having recessive resistance to *Xanthomonas euvesicatoria*, the method comprising the steps of:

a) making a 6-bp deletion in the CYSTM region of at least one CYSTM gene in at least one cell from a sensitive plant using a genome editing method whereby at least one modified CYSTM gene is produced, wherein the modified CYSTM gene encodes a protein comprising a deletion of two amino acids at the locations corresponding to positions 87 and 88 of the amino acid sequence set forth in SEQ ID NO: 42, and wherein the at least one CYSTM gene comprises a nucleotide sequence selected from the group consisting of i. the nucleotide sequence set forth in SEQ ID NO: 41, 49, or 51, ii. a nucleotide sequence encoding the amino acid sequence set forth in SEQ ID NO: 42, 50, or 52, iii. a nucleotide sequence comprising at least 95% identity to at least one nucleotide sequence selected from the group consisting of the nucleotide sequences set forth in SEQ ID NOS: 41, 49, and 51, wherein the at least one modified CYSTM gene is capable of conferring to a plant resistance to *Xanthomonas euvesicatoria*, and iv. a nucleotide sequence encoding an amino acid sequence comprising at least 95% identity to at least one amino acid sequence selected from the group consisting of the amino acid sequences set forth in SEQ ID NOS: 42, 50, and 52, wherein the at least one modified CYSTM gene is capable of conferring to a plant resistance to *Xanthomonas euvesicatoria*; and b) regenerating a plant from the at least one cell, wherein the plant comprises the at least one modified CYSTM gene.

7. A method for generating a tomato plant that is resistant to *Xanthomonas euvesicatoria*, the method comprising the steps of:

a) making a 6-bp deletion in the SlXcv-1A gene (SEQ ID NO:49) and/or the SlXcv-1B gene (SEQ ID NO:51) in at least one tomato cell from a sensitive tomato plant using a genome editing method, wherein the 6-bp deletion corresponds to the nucleotides in the SlXcv-1A gene and/or the SlXcv-1B gene that encode the 5th and 6th amino acids from the C-terminus of the CYSTM region of the protein encoded by the SlXcv-1A gene and/or the SlXcv-1B gene; and b) regenerating a tomato plant from the at least one tomato cell, wherein the tomato plant is resistant to *Xanthomonas euvesicatoria*.

8. A food product produced from the tomato plant of claim 5 or part thereof, wherein the food product comprises at least one of the modified CYSTM genes.

9. A seed of the tomato plant of claim 5, wherein the seed comprises the at least one of the modified CYSTM genes.

10. The tomato plant of claim 5, wherein the first modified CYSTM gene comprises the nucleotide sequence set forth in SEQ ID NO: 59 or encodes the amino acid sequence set forth in SEQ ID NO: 60 and the second modified CYSTM gene comprises the nucleotide set forth in SEQ ID NO: 66 or encodes the amino acid sequence set forth in SEQ ID NO: 67.

11. The tomato plant of claim 5, wherein C-terminal 12 amino acids of the protein encoded by the first modified CYSTM gene and the protein encoded by the second modified CYSTM gene are LAALCCCCDACF (SEQ ID NO:141).

12. The method of claim 6, wherein the plant is a plant from the Solanaceae family.

13. The method of claim 6, wherein the plant is selected from the group consisting of tomato and pepper.

14. The method of claim 6, wherein the C-terminal 12 amino acids of the protein encoded by the modified CYSTM gene are LAALCCCCDACF (SEQ ID NO:141).

* * * * *

                        SEQUENCE LISTING

<160> NUMBER OF SEQ ID NOS: 151

<210> SEQ ID NO 1
    <211> LENGTH: 22
    <212> TYPE: DNA
    <213> ORGANISM: Capsicum annuum
    <220> FEATURE:
    <221> NAME/KEY: source
    <222> LOCATION: 1..22
    <223> OTHER INFORMATION: mol type=unassigned DNA
          note=Primer CaCY F1
          organism=Capsicum annuum

<400> SEQUENCE: 1
gtggctcatg ctgtggattt ct                                                  22

<210> SEQ ID NO 2
    <211> LENGTH: 22
    <212> TYPE: DNA
    <213> ORGANISM: Capsicum annuum
    <220> FEATURE:
    <221> NAME/KEY: source
    <222> LOCATION: 1..22
    <223> OTHER INFORMATION: mol type=unassigned DNA
          note=Primer CaCY R1
          organism=Capsicum annuum

<400> SEQUENCE: 2
ccaggagtgc aggggtaggt ta                                                  22

<210> SEQ ID NO 3
    <211> LENGTH: 22
    <212> TYPE: DNA
    <213> ORGANISM: Capsicum annuum
    <220> FEATURE:
    <221> NAME/KEY: source
    <222> LOCATION: 1..22
    <223> OTHER INFORMATION: mol type=unassigned DNA
          note=Primer BAC 279 op F1
          organism=Capsicum annuum

<400> SEQUENCE: 3
gctggtctat cttgatcctt ca                                                  22

<210> SEQ ID NO 4
    <211> LENGTH: 22
    <212> TYPE: DNA
    <213> ORGANISM: Capsicum annuum
    <220> FEATURE:
    <221> NAME/KEY: source
```

```
<222> LOCATION: 1..22
<223> OTHER INFORMATION: mol type=unassigned DNA
      note=Primer BAC 279 op R1
      organism=Capsicum annuum

<400> SEQUENCE: 4
atgtccctcc ctgtcattct at                                              22

<210> SEQ ID NO 5
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 279 -40 F1
      organism=Capsicum annuum

<400> SEQUENCE: 5
tgggactaat aaggaaagaa                                                 20

<210> SEQ ID NO 6
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 279 -40 R1
      organism=Capsicum annuum

<400> SEQUENCE: 6
gaagtgatga aagtgggttg                                                 20

<210> SEQ ID NO 7
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 1248 op F1
      organism=Capsicum annuum

<400> SEQUENCE: 7
acgagcttga gatactga                                                   18

<210> SEQ ID NO 8
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 1248 op R1
      organism=Capsicum annuum

<400> SEQUENCE: 8
ctcttgggaa aggtcata                                                   18

<210> SEQ ID NO 9
<211> LENGTH: 18
<212> TYPE: DNA
<213> ORGANISM: Capsicum annuum
<220> FEATURE:
```

-continued

```
<221> NAME/KEY: source
<222> LOCATION: 1..18
<223> OTHER INFORMATION: mol type=unassigned DNA
      note=Primer BAC 1248 -40 F1
      organism=Capsicum annuum

<400> SEQUENCE: 9
gtcttacatg ccccaaat                                                 18

<210> SEQ ID NO 10
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 1248 -40 R1
      organism=Capsicum annuum

<400> SEQUENCE: 10
catcacgagc actacctg                                                 18

<210> SEQ ID NO 11
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 1191 -40 F1
      organism=Capsicum annuum

<400> SEQUENCE: 11
aaaactgggt taatgttggg                                               20

<210> SEQ ID NO 12
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 1191- 40 R1
      organism=Capsicum annuum

<400> SEQUENCE: 12
cgtggcggct gtattgtctc                                               20

<210> SEQ ID NO 13
<211> LENGTH: 21
<212> TYPE: DNA
<213> ORGANISM: Capsicum annuum
<220> FEATURE:
<221> NAME/KEY: source
<222> LOCATION: 1..21
<223> OTHER INFORMATION: mol type=unassigned DNA
      note=Primer BAC 1191 op F1
      organism=Capsicum annuum

<400> SEQUENCE: 13
acgagcaaat agaaggcaat g                                             21

<210> SEQ ID NO 14
<211> LENGTH: 20
<212> TYPE: DNA
<213> ORGANISM: Capsicum annuum
```

```
<220> FEATURE:
<221> NAME/KEY: source
<222> LOCATION: 1..20
<223> OTHER INFORMATION: mol type=unassigned DNA
      note=Primer BAC 1191 op R1
      organism=Capsicum annuum

<400> SEQUENCE: 14
caccctctac aagaaactct                                              20

<210> SEQ ID NO 15
<211> LENGTH: 21
<212> TYPE: DNA
<213> ORGANISM: Capsicum annuum
<220> FEATURE:
<221> NAME/KEY: source
<222> LOCATION: 1..21
<223> OTHER INFORMATION: mol type=unassigned DNA
      note=Primer BAC 877 -40 F1
      organism=Capsicum annuum

<400> SEQUENCE: 15
atgtcaagaa tcacaaccgt a                                            21

<210> SEQ ID NO 16
<211> LENGTH: 21
<212> TYPE: DNA
<213> ORGANISM: Capsicum annuum
<220> FEATURE:
<221> NAME/KEY: source
<222> LOCATION: 1..21
<223> OTHER INFORMATION: mol type=unassigned DNA
      note=Primer BAC 877 -40 R1
      organism=Capsicum annuum

<400> SEQUENCE: 16
gtaagatggc cgattaatat g                                            21

<210> SEQ ID NO 17
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 632 -40 F1
      organism=Capsicum annuum

<400> SEQUENCE: 17
ttgccagaag ttgtcctatt                                              20

<210> SEQ ID NO 18
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 632 -40 R1
      organism=Capsicum annuum

<400> SEQUENCE: 18
attgtcttgt tgtgcgttat                                              20

<210> SEQ ID NO 19
<211> LENGTH: 20
<212> TYPE: DNA
```

-continued

```
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 632 op F1
      organism=Capsicum annuum

<400> SEQUENCE: 19
tcaacaaagg cagcagaatg                                               20

<210> SEQ ID NO 20
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 632 op R1
      organism=Capsicum annuum

<400> SEQUENCE: 20
ttctgctctt ttccctgaa                                                20

<210> SEQ ID NO 21
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 66 -40 F1
      organism=Capsicum annuum

<400> SEQUENCE: 21
gcttagaggg caggtagt                                                 18

<210> SEQ ID NO 22
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer 66 -40 R1
      organism=Capsicum annuum

<400> SEQUENCE: 22
ttctcagagc taggcaca                                                 18

<210> SEQ ID NO 23
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer 66 op F1
      organism=Capsicum annuum

<400> SEQUENCE: 23
tatgcaaagc acatgaaatg                                               20

<210> SEQ ID NO 24
<211> LENGTH: 20
```

```
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 66 op R1
      organism=Capsicum annuum

<400> SEQUENCE: 24
cttatgacac cccaccaaat                                               20

<210> SEQ ID NO 25
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 50 op F1
      organism=Capsicum annuum

<400> SEQUENCE: 25
accaactaga atccaaat                                                 18

<210> SEQ ID NO 26
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 50 op R1
      organism=Capsicum annuum

<400> SEQUENCE: 26
tgaacttaaa gatgctga                                                 18

<210> SEQ ID NO 27
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 50 -40 F1
      organism=Capsicum annuum

<400> SEQUENCE: 27
atgatttcta tgatggctag                                               20

<210> SEQ ID NO 28
<211> LENGTH: 19
<212> TYPE: DNA
<213> ORGANISM: Capsicum annuum
<220> FEATURE:
<221> NAME/KEY: source
<222> LOCATION: 1..19
<223> OTHER INFORMATION: mol type=unassigned DNA
      note=Primer BAC 50 -40 R1
      organism=Capsicum annuum

<400> SEQUENCE: 28
gttggaagta ttgggttaa                                                19

<210> SEQ ID NO 29
```

-continued

```
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 472 -40 F1
      organism=Capsicum annuum

<400> SEQUENCE: 29
cttgcttcta gttttgatcc                                           20

<210> SEQ ID NO 30
<211> LENGTH: 20
<212> TYPE: DNA
<213> ORGANISM: Capsicum annuum
<220> FEATURE:
<221> NAME/KEY: source
<222> LOCATION: 1..20
<223> OTHER INFORMATION: mol type=unassigned DNA
      note=Primer BAC 472 -40 R1
      organism=Capsicum annuum

<400> SEQUENCE: 30
ctatctggca agtaaccacc                                           20

<210> SEQ ID NO 31
<211> LENGTH: 17
<212> TYPE: DNA
<213> ORGANISM: Capsicum annuum
<220> FEATURE:
<221> NAME/KEY: source
<222> LOCATION: 1..17
<223> OTHER INFORMATION: mol type=unassigned DNA
      note=Primer BAC 472 op F1
      organism=Capsicum annuum

<400> SEQUENCE: 31
cttcaatccc tttctca                                              17

<210> SEQ ID NO 32
<211> LENGTH: 18
<212> TYPE: DNA
<213> ORGANISM: Capsicum annuum
<220> FEATURE:
<221> NAME/KEY: source
<222> LOCATION: 1..18
<223> OTHER INFORMATION: mol type=unassigned DNA
      note=Primer BAC 472 op R1
      organism=Capsicum annuum

<400> SEQUENCE: 32
tatcatgctc atccctat                                             18

<210> SEQ ID NO 33
<211> LENGTH: 24
<212> TYPE: DNA
<213> ORGANISM: Capsicum annuum
<220> FEATURE:
<221> NAME/KEY: source
<222> LOCATION: 1..24
<223> OTHER INFORMATION: mol type=unassigned DNA
      note=Primer, a Pr6 marker F1 primere
      organism=Capsicum annuum

<400> SEQUENCE: 33
tttcgtgagt attattcctt ttta                                      24
```

```
<210> SEQ ID NO 34
<211> LENGTH: 19
<212> TYPE: DNA
<213> ORGANISM: Capsicum annuum
<220> FEATURE:
<221> NAME/KEY: source
<222> LOCATION: 1..19
<223> OTHER INFORMATION: mol type=unassigned DNA
      note=Preimer, a Pr6 marker R1 primere
      organism=Capsicum annuum

<400> SEQUENCE: 34
cgctgctttt tcgctatgt                                                19

<210> SEQ ID NO 35
<211> LENGTH: 19
<212> TYPE: DNA
<213> ORGANISM: Capsicum annuum
<220> FEATURE:
<221> NAME/KEY: source
<222> LOCATION: 1..19
<223> OTHER INFORMATION: mol type=unassigned DNA
      note=Primer, a Pr4b marker F1 primere
      organism=Capsicum annuum

<400> SEQUENCE: 35
cgctgctttt tcgctatgt                                                19

<210> SEQ ID NO 36
<211> LENGTH: 19
<212> TYPE: DNA
<213> ORGANISM: Capsicum annuum
<220> FEATURE:
<221> NAME/KEY: source
<222> LOCATION: 1..19
<223> OTHER INFORMATION: mol type=unassigned DNA
      note=Primer, a Pr4b marker R1 primere
      organism=Capsicum annuum

<400> SEQUENCE: 36
tacgacaaac caccgactc                                                19

<210> SEQ ID NO 37
<211> LENGTH: 2433
<212> TYPE: DNA
<213> ORGANISM: Capsicum annuum
<220> FEATURE:
<221> NAME/KEY: source
<222> LOCATION: 1..2433
<223> OTHER INFORMATION: mol type=unassigned DNA
      note=Caxcv-1 genomi DNS
      organism=Capsicum annuum
<220> FEATURE:
<221> NAME/KEY: CDS
<222> LOCATION: join(918..969,1079..1259,2034..2070)
<223> OTHER INFORMATION: transl table=1
<220> FEATURE:
<221> NAME/KEY: 5'UTR
<222> LOCATION: 781..917
<220> FEATURE:
<221> NAME/KEY: exon
<222> LOCATION: join(781..969,1079..1259,2034..2312)
<220> FEATURE:
<221> NAME/KEY: mRNA
<222> LOCATION: join(781..969,1079..1259,2034..2312)
<220> FEATURE:
<221> NAME/KEY: intron
<222> LOCATION: join(970..1078,1260..2033)
<220> FEATURE:
<221> NAME/KEY: 3'UTR
<222> LOCATION: 2071..2312
<220> FEATURE:
<221> NAME/KEY: polyA site
```

<222> LOCATION: 2312

<400> SEQUENCE: 37

```
acttctaatt gtggataaaa atagtttaaa atttaatact tccttcgttt caaataatt      60
gaattgttga gtattttta gggttcaaaa taattaaatt gttcattatt caagatatat    120
gttgaatttt tttattttt ttttaaattt acttttatta attaaatttt caagattgag    180
ttccaatggt cattattaat gttttagaat ttgaaaagga caaaaatgaa aaacatgac    240
taatttatat ttttatcttt ttttcttaaa agtgtgtcat atttaataa ttcaattatt    300
ttgaaacgag gagagtaatt ttttttaatc aactaaaacc ataatttat actctcttcg    360
tcccaaattt tctaatttgt ttttccatgt gtttacccct tgcattattt ctttttttctt  420
caaattaaaa tgtaaacatg atttaatagg gatattatgg taaactagac atgttattaa    480
ttatttttct taatcaatgt gtcatctcaa tctgaaacgg agggagtatc tttatctttt    540
ttttcttaaa actgtgtcat atttcaacaa ttcaattatt ttaaaacgga ggaattaatt    600
ttttcaatc aaataaaacc ataatttat aataattctt taaaaaaaaa taaaaaagaa      660
tttccgcgca ttggacgcgg gtacgtatta aagctaccta tgacaacatg ggaaaagatt    720
acattataaa aaaacaaaa ataagagttt cttggaatgt gcaatcgtct ttgtttttccc    780
ctttgacttt actctataaa aacttcacaa atatcacctc ttcactgtac cccattatct    840
ttctttgtgg ttaagcaaat acacaaaata aataaatata actctcctct tagattaaac    900
```
tagtagatcc atcaaca atg agt tac tac aat caa caa caa cct cct gtt    950
                  Met Ser Tyr Tyr Asn Gln Gln Gln Pro Pro Val
                   1           5               10 ggt gta cct cca cca caa g gtaaaaaaaa aaaaggaag aaacaactct    999
Gly Val Pro Pro Pro Gln
         15 gactttgttg tatgtgaatt gttttagtta ttagatctga ttgatttta tttttttggg    1059 ggtattttt gtgatttag gg tat cca cca gaa ggt tac cca aaa gat tca      1110
                   Gly Tyr Pro Pro Glu Gly Tyr Pro Lys Asp Ser
                      20                25 tac cca cca cct gga tat cca cag caa ggg tac cct caa caa ggg tat    1158
Tyr Pro Pro Pro Gly Tyr Pro Gln Gln Gly Tyr Pro Gln Gln Gly Tyr
   30                35                40 cca cca caa ggg tac cct cca cag tat gca cct cag tat ggt gca cca    1206
Pro Pro Gln Gly Tyr Pro Pro Gln Tyr Ala Pro Gln Tyr Gly Ala Pro
45               50                55                60 cct cct caa caa caa cat caa tca tct agt agt act gga tta ttg caa    1254
Pro Pro Gln Gln Gln His Gln Ser Ser Ser Ser Thr Gly Leu Leu Gln
              65                70                75 gga tg gtatgtacac cttattagga ctctattttt ctatatgttg acttgtatgg    1309
Gly Cys

```
atgtgttatg taggatctga ggtttatagg attgagttga ccatgtcttg tttgtgtgat    1369
aagatatgaa ttgatgtgaa cttgattcat caagatctat atgacctcag gttttgttga    1429
ctgagttgcc tgaatttttt atcaaaatat gtattaggtt ttaaaaagat ttaacggatc    1489
aaagcggtgt taaaactaga aatagttat gacagtaacg ttaacaagac tctgcaactc    1549
tgccacatca tactatttgt cagagttgca gagtctctga agttctaagt caactctgca    1609
acatcagact cacaaagttg atttggcaga attgcagtgt ctcttcatta ttggtgaggt    1669
tttaagtcaa aaacgttatt gtcagtaacg attcctgctt tgacgtcgtc cattgttcat    1729
tttgtgtccg ttaattttt taaaacttaa taacgtttat actggttttg gaaagttttc    1789
```

-continued

```
taaaaacata ctactctggt gaattgattt aaaaaataat ttattttggt caaaacttca    1849
agttgcttgg tgaagctgac ctcgtgtcta accgggaggt actggctgaa aatagcctca    1909
tgcaagataa ggctaggtta taataaacct ttgtggttcg gttcttccta cacaccgagt    1969
ctcatgctgt ttccaattat tggtcggatt aataatcgat ttttttttatt ttattttttt    2029 tcag t ttg gct gct ctt tgc tgt tgc tgt gat gca tgc ttt tgatgctgta    2080
     Leu Ala Ala Leu Cys Cys Cys Cys Asp Ala Cys Phe
              80              85              90 aatgatctgt acgcaaagtg ttgatgacaa aagatgattg aaatccatta tcatagtcta    2140
gattattttc cttgaacgtg ttttgtcctt gttgtcctgt catttataaa aatttgatc    2200 ttgctatggt gtctatttgc caaattatac gtttatgtac aacgtgagag attgtatttt    2260 atttttatg ttttggacct caatatgtga atcaatgcac cttgatttgg ttaaacaatt     2320
tatcgcctca tgtgtgtcta taatccaagc gcttggatag tggcggattc aggatttact    2380
ttgagagggt tcagaagtat atatacgaga attaatcaaa gggggtttaat atc           2433
```

<210> SEQ ID NO 38
<211> LENGTH: 90
<212> TYPE: PRT
<213> ORGANISM: Capsicum annuum
<220> FEATURE:
<223> OTHER INFORMATION: [CDS]:join(918..969,1079..1259,2034..2070) from SEQ ID NO 37

<400> SEQUENCE: 38

```
Met Ser Tyr Tyr Asn Gln Gln Gln Pro Pro Val Gly Val Pro Pro Pro
1               5                   10                  15

Gln Gly Tyr Pro Pro Glu Gly Tyr Pro Lys Asp Ser Tyr Pro Pro Pro
            20                  25                  30

Gly Tyr Pro Gln Gln Gly Tyr Pro Gln Gln Gly Tyr Pro Pro Gln Gly
        35                  40                  45

Tyr Pro Pro Gln Tyr Ala Pro Gln Tyr Gly Ala Pro Pro Pro Gln Gln
    50                  55                  60

Gln His Gln Ser Ser Ser Ser Thr Gly Leu Leu Gln Gly Cys Leu Ala
65                  70                  75                  80

Ala Leu Cys Cys Cys Cys Asp Ala Cys Phe
                85                  90
```

<210> SEQ ID NO 39
<211> LENGTH: 649
<212> TYPE: DNA
<213> ORGANISM: Capsicum annuum
<220> FEATURE:
<221> NAME/KEY: source
<222> LOCATION: 1..649
<223> OTHER INFORMATION: mol type=unassigned DNA
       note=TC14947
       organism=Capsicum annuum
<220> FEATURE:
<221> NAME/KEY: CDS
<222> LOCATION: 132..407
<223> OTHER INFORMATION: transl table=1
<220> FEATURE:
<221> NAME/KEY: 5'UTR
<222> LOCATION: 1..81
<220> FEATURE:
<221> NAME/KEY: 3'UTR
<222> LOCATION: 408..649
<220> FEATURE:
<221> NAME/KEY: polyA site
<222> LOCATION: 649

<400> SEQUENCE: 39

```
ctttactcta taaaaacttc acaaatatca cctcttcact gtaccccatt atctttcttt    60
gtggttaagc aaatacacaa aataaataaa tataactctc ctcttagatt aaactagtag   120
atccatcaac a atg agt tac tac aat caa caa caa cct cct gtt ggt gta   170
            Met Ser Tyr Tyr Asn Gln Gln Gln Pro Pro Val Gly Val
             1               5                  10 cct cca cca caa ggg tat cca cca gaa ggt tac cca aaa gat tca tac   218
Pro Pro Pro Gln Gly Tyr Pro Pro Glu Gly Tyr Pro Lys Asp Ser Tyr
     15                  20                  25 cca cca cct gga tat cca cag caa ggg tac cct caa caa ggg tat cca   266
Pro Pro Pro Gly Tyr Pro Gln Gln Gly Tyr Pro Gln Gln Gly Tyr Pro
 30                  35                  40                  45 cca caa ggg tac cct cca cag tat gca cct cag tat ggt gca cca cct   314
Pro Gln Gly Tyr Pro Pro Gln Tyr Ala Pro Gln Tyr Gly Ala Pro Pro
                 50                  55                  60 cct caa caa caa cat caa tca tct agt agt act gga tta ttg caa gga   362
Pro Gln Gln Gln His Gln Ser Ser Ser Ser Thr Gly Leu Leu Gln Gly
             65                  70                  75 tgt ttg gct gct ctt tgc tgt tgc tgt ctc ttg gat gca tgc ttt       407
Cys Leu Ala Ala Leu Cys Cys Cys Cys Leu Leu Asp Ala Cys Phe
         80                  85                  90 tgatgctgta aatgatctgt acgcaaagtg ttgatgacaa aagatgattg aaatccatta   467
tcatagtcta gattattttc cttgaacgtg ttttgtcctt gttgtcctgt catttataaa   527
taatttgatc ttgctatggt gtctatttgc caaattatag gtttatgtac aacgtgagag   587
attgtatttt attttttatg ttttggacct caatatgtga atcaatgcac cttgatttgg   647
tt                                                                  649

<210> SEQ ID NO 40
<211> LENGTH: 92
<212> TYPE: PRT
<213> ORGANISM: Capsicum annuum
<220> FEATURE:
<223> OTHER INFORMATION: [CDS]:132..407 from SEQ ID NO 39

<400> SEQUENCE: 40

Met Ser Tyr Tyr Asn Gln Gln Gln Pro Pro Val Gly Val Pro Pro
 1               5                  10                  15

Gln Gly Tyr Pro Pro Glu Gly Tyr Pro Lys Asp Ser Tyr Pro Pro
                 20                  25                  30

Gly Tyr Pro Gln Gln Gly Tyr Pro Gln Gln Gly Tyr Pro Pro Gln Gly
             35                  40                  45

Tyr Pro Pro Gln Tyr Ala Pro Gln Tyr Gly Ala Pro Pro Pro Gln Gln
 50                  55                  60

Gln His Gln Ser Ser Ser Ser Thr Gly Leu Leu Gln Gly Cys Leu Ala
65                  70                  75                  80

Ala Leu Cys Cys Cys Cys Leu Leu Asp Ala Cys Phe

<210> SEQ ID NO 41
<211> LENGTH: 2436
<212> TYPE: DNA
<213> ORGANISM: Capsicum annuum
<220> FEATURE:
<221> NAME/KEY: source
<222> LOCATION: 1..2436
<223> OTHER INFORMATION: mol type=unassigned DNA
      note=Xcv-1
      organism=Capsicum annuum
<220> FEATURE:
<221> NAME/KEY: CDS
```

```
<222> LOCATION: join(917..968,1078..1258,2033..2075)
<223> OTHER INFORMATION: transl table=1
<220> FEATURE:
<221> NAME/KEY: 5'UTR
<222> LOCATION: join(780..916)
<220> FEATURE:
<221> NAME/KEY: exon
<222> LOCATION: join(780..968,1078..1258,2033..2317)
<220> FEATURE:
<221> NAME/KEY: mRNA
<222> LOCATION: join(780..968,1078..1258,2032..2317)
<220> FEATURE:
<221> NAME/KEY: intron
<222> LOCATION: join(968..1077,1259..2032)
<220> FEATURE:
<221> NAME/KEY: 3'UTR
<222> LOCATION: join(2076..2317)
<220> FEATURE:
<221> NAME/KEY: polyA site
<222> LOCATION: 2317

<400> SEQUENCE: 41
acttctaatt gtggataaaa atagtttaaa atttaatact tccttcgttt caaataatt      60 gaattgttga gtatttttta gggttcaaaa taattaaatt gttcattatt caagatatat    120
gttgaatttt tttattttt  tttaaattta ctttttattaa ttaaatttc  aagattgagt   180 tccaatggtc attattaatg ttttagaatt tgaaaaggac aaaaatgaaa aacatgact     240 aattatatt  tttatcttt  tttcttaaaa gtgtgtcata ttttaataat tcaattattt    300
tgaaacgagg agagtaattt tttttaatca actaaaacca taatttata ctctcttcgt     360 cccaaattt  ctaatttgtt tttccatgtg tttacccttt gcattattc  ttttttcttc   420 aaattaaaat gtaaacatga tttaatagg  atattatggt aaactagaca tgttattaat    480
tatttttctt aatcaatgtg tcatctcaat ctgaaacgga gggagtatct ttatcttttt    540
tttcttaaaa ctgtgtcata tttcaacaat tcaattattt taaaacggag gaattaattt    600
ttttcaatca aataaaacca taatttata ataattcttt aaaaaaaaat aaaaagaat      660 ttccgcgcat tggacgcggg tacgtattaa agctacctat gacaacatgg gaaaagatta    720
cattataaaa aaaacaaaaa taagagttc  ttggaatgtg caatcgtctt tgttttcccc    780 tttgactta  ctctataaaa acttcacaaa tatcacctct tcactgtacc ccattatctt    840
tctttgtggt taagcaaata cacaaaataa ataaatataa ctctcctctt agattaaact    900
agtagatcca tcaaca atg agt tac tac aat caa caa caa cct cct gtt ggt    952
               Met Ser Tyr Tyr Asn Gln Gln Gln Pro Pro Val Gly
                 1               5                  10 gta cct cca cca caa g gtaaaaaaaa aaaaggaag aaacaactct gactttgttg   1008
Val Pro Pro Pro Gln
         15 tatgtgaatt gttttagtta ttagatctga ttgatttta tttttttggg ggtatttttt     1068 gtgatttag gg tat cca cca gaa ggt tac cca aaa gat tca tac cca cca    1118
            Gly Tyr Pro Pro Glu Gly Tyr Pro Lys Asp Ser Tyr Pro Pro
                    20                  25                  30 cct gga tat cca cag caa ggg tac cct caa caa ggg tat cca cca caa    1166
Pro Gly Tyr Pro Gln Gln Gly Tyr Pro Gln Gln Gly Tyr Pro Pro Gln
            35                  40                  45 ggg tac cct cca cag tat gca cct cag tat ggt gca cca cct cct caa    1214
Gly Tyr Pro Pro Gln Tyr Ala Pro Gln Tyr Gly Ala Pro Pro Pro Gln
            50                  55                  60 caa caa cat caa tca tct agt agt act gga tta ttg caa gga tg         1258
Gln Gln His Gln Ser Ser Ser Ser Thr Gly Leu Leu Gln Gly Cys
            65                  70                  75
```

-continued

```
gtatgtacac cttattagga ctctattttt ctatatgttg acttgtatgg atgtgttatg    1318
taggatctga ggtttatagg attgagttga ccatgtcttg tttgtgtgat aagatatgaa    1378
ttgatgtgaa cttgattcat caagatctat atgacctcag gttttgttga ctgagttgcc    1438 tgaattttt atcaaaatat gtattaggtt taaaaagat ttaacggatc aaagcggtgt     1498
taaaactaga aatagtttat gacagtaacg ttaacaagac tctgcaactc tgccacatca    1558
tactatttgt cagagttgca gagtctctga agttctaagt caactctgca acatcagact    1618
cacaaagttg atttggcaga attgcagtgt ctcttcatta ttggtgaggt tttaagtcaa    1678
aaacgttatt gtcagtaacg attcctgctt tgacgtcgtc cattgttcat tttgtgtccg    1738 ttaattttt taaaacttaa taacgtttat actggttttg gaaagttttc taaaaacata    1798
ctactctggt gaattgattt aaaaaataat ttattttggt caaaacttca agttgcttgg    1858
tgaagctgac ctcgtgtcta accgggaggt actggctgaa aatagcctca tgcaagataa    1918
ggctaggtta taataaacct ttgtggttcg gttcttccta cacaccgagt ctcatgctgt    1978
ttccaattat cggtcggatt aataatcgat ttttttatt ttattttttt tcag t ttg    2036
                                                              Leu gct gct ctt tgc tgt tgc tgt ctc ttg gat gca tgc ttt tgatgctgta      2085
Ala Ala Leu Cys Cys Cys Cys Leu Leu Asp Ala Cys Phe
 80              85                  90 aatgatctgt acgcaaagtg ttgatgacaa aagatgattg aaatccatta tcatagtcta    2145
gattattttc cttgaacgtg ttttgtcctt gttgtcctgt catttataaa taatttgatc    2205
ttgctatggt gtctatttgc caaattatag gtttatgtac aacgtgagag attgtattt     2265 attttttatg ttttggacct caatatgtga atcaatgcac cttgatttgg ttaaacaatt    2325
tatcgcctca tgtgtctata atccaagcgc ttggatagtg gcggattcag gatttacttt    2385
gagagggttc agaagtatat atacgagaat taatcaaagg ggtttaatat c             2436
```

<210> SEQ ID NO 42
<211> LENGTH: 92
<212> TYPE: PRT
<213> ORGANISM: Capsicum annuum
<220> FEATURE:
<223> OTHER INFORMATION: [CDS]:join(917..968,1078..1258,2033..2075) from
      SEQ ID NO 41

<400> SEQUENCE: 42

Met Ser Tyr Tyr Asn Gln Gln Gln Pro Pro Val Gly Val Pro Pro Pro
1               5                   10                  15

Gln Gly Tyr Pro Pro Glu Gly Tyr Pro Lys Asp Ser Tyr Pro Pro
            20                  25                  30

Gly Tyr Pro Gln Gln Gly Tyr Pro Gln Gln Gly Tyr Pro Gln Gly
        35                  40                  45

Tyr Pro Pro Gln Tyr Ala Pro Gln Tyr Gly Ala Pro Pro Gln Gln
    50                  55                  60

Gln His Gln Ser Ser Ser Ser Thr Gly Leu Leu Gln Gly Cys Leu Ala
65                  70                  75                  80

Ala Leu Cys Cys Cys Cys Leu Leu Asp Ala Cys Phe
                85                  90

<210> SEQ ID NO 43
<211> LENGTH: 22
<212> TYPE: DNA
<213> ORGANISM: Escherichia coli
<220> FEATURE:
<221> NAME/KEY: source

```
<222> LOCATION: 1..22
<223> OTHER INFORMATION: mol type=unassigned DNA
      note=Primer: Pr mGFP NcoI F for cloning GFP in pGemT-Easy
      organism=Escherichia coli

<400> SEQUENCE: 43
ccatggtaag taaaggagaa ga                                          22

<210> SEQ ID NO 44
<211> LENGTH: 24
<212> TYPE: DNA
<213> ORGANISM: Escherichia coli
<220> FEATURE:
<221> NAME/KEY: source
<222> LOCATION: 1..24
<223> OTHER INFORMATION: mol type=unassigned DNA
      note=Primer: Pr mGFP XbaI R for cloing GFP into pGemT-Easy
      organism=Escherichia coli

<400> SEQUENCE: 44
tctagaagct ttgtatagtt catc                                        24

<210> SEQ ID NO 45
<211> LENGTH: 26
<212> TYPE: DNA
<213> ORGANISM: Escherichia coli
<220> FEATURE:
<221> NAME/KEY: source
<222> LOCATION: 1..26
<223> OTHER INFORMATION: mol type=unassigned DNA
      note=Primer: Pr Xcv-1 XbaI F for cloning both alleles
      organism=Escherichia coli

<400> SEQUENCE: 45
tctagaatga gttactacaa tcaaca                                      26

<210> SEQ ID NO 46
<211> LENGTH: 21
<212> TYPE: DNA
<213> ORGANISM: Escherichia coli
<220> FEATURE:
<221> NAME/KEY: source
<222> LOCATION: 1..21
<223> OTHER INFORMATION: mol type=unassigned DNA
      note=Primer Pr Xcv-1 BcuI R for cloning both alleles
      organism=Escherichia coli

<400> SEQUENCE: 46
actagttcaa aagcatgcat c                                           21

<210> SEQ ID NO 47
<211> LENGTH: 10817
<212> TYPE: DNA
<213> ORGANISM: Escherichia coli
<220> FEATURE:
<221> NAME/KEY: source
<222> LOCATION: 1..10817
<223> OTHER INFORMATION: mol type=unassigned DNA
      note=pCambia GFP-Xcv-1
      organism=Escherichia coli

<400> SEQUENCE: 47
ccatggtaag taaaggagaa gaacttttca ctggagttgt cccaattctt gttgaattag    60
atggtgatgt taatgggcac aaattttctg tcagtggaga gggtgaaggt gatgcaacat   120
acggaaaact acccttaaa tttatttgca ctactggaaa actacctgtt ccgtggccaa   180
cacttgtcac tactttctct tatggtgttc aatgcttttc aagatatacc gatcatatga   240
```

-continued

```
agcggcacga cttcttcaag agcgccatgc ctgagggata cgtgcaggag aggaccatct    300
tcttcaagga cgacgggaac tacaagacac gtgctgaagt caagtttgag ggagacaccc    360
tcgtcaacag gatcgagctt aagggaatcg atttcaagga ggacggaaac atcctcggcc    420
acaagttgga atacaactac aactcccaca acgtatacat catggccgac aagcaaaaga    480
acggcatcaa agccaacttc aagacccgcc acaacatcga agacggcggc gtgcaactcg    540
ctgatcatta tcaacaaaat actccaattg gcgatggccc tgtccttta ccagacaacc     600 attacctgtc cacacaatct gccctttcga aagatcccaa cgaaaagaga gaccacatgg    660
tccttcttga gtttgtaaca gctgctggga ttacacatgg catggatgaa ctatacaaag    720
cttctagaat gagttactac aatcaacaac aacctcctgt tggtgtacct ccaccacaag    780
ggtatccacc agaaggttac ccaaaagatt catacccacc acctggatat ccacagcaag    840
ggtaccctca acagggtat ccaccacaag ggtaccctcc acagtatgca cctcagtatg      900
gtgcaccacc tcctcaacaa caacatcaat catctagtag tactggatta ttgcaaggat    960
gtttggctgc tctttgctgt tgctgtctct tggatgcatg cttttgaact agtgaattcg    1020
cggccgcctg caggcagctc gaatttcccc gatcgttcaa acatttggca ataaagtttc    1080
ttaagattga atcctgttgc cggtcttgcg atgattatca tataatttct gttgaattac    1140
gttaagcatg taataattaa catgtaatgc atgacgttat ttatgagatg gttttttatg    1200
attagagtcc cgcaattata catttaatac gcgatagaaa acaaaatata gcgcgcaaac    1260
taggataaat tatcgcgcgc ggtgtcatct atgttactag atcgggaatt aaactatcag    1320
tgtttgacag gatatattgg cgggtaaacc taagagaaaa gagcgtttat tagaataacg    1380
gatatttaaa agggcgtgaa aaggtttatc cgttcgtcca tttgtatgtg catgccaacc    1440
acagggttcc cctcgggatc aaagtacttt gatccaaccc ctccgctgct atagtgcagt    1500
cggcttctga cgttcagtgc agccgtcttc tgaaaacgac atgtcgcaca agtcctaagt    1560
tacgcgacag gctgccgccc tgccctttc ctggcgtttt cttgtcgcgt gttttagtcg     1620
cataaagtag aatacttgcg actagaaccg gagacattac gccatgaaca gagcgccgc    1680 cgctggcctg ctgggctatg cccgcgtcag caccgacgac caggacttga ccaaccaacg    1740
ggccgaactg cacgcggccg gctgcaccaa gctgttttcc gagaagatca ccggcaccag    1800
gcgcgaccgc ccggagctgg ccaggatgct tgaccaccta cgccctggcg acgttgtgac    1860
agtgaccagg ctagaccgcc tggcccgcag cacccgcgac ctactggaca ttgccgagcg    1920
catccaggag gccggcgcgg gcctgcgtag cctggcagag ccgtgggccg acaccaccac    1980
gccggccggc cgcatggtgt tgaccgtgtt cgccggcatt gccgagttcg agcgttccct    2040
aatcatcgac cgcacccgga gcgggcgcga ggccgccaag gcccgaggcg tgaagtttgg    2100
cccccgccct accctcaccc cggcacagat cgcgcacgcc cgcgagctga tcgaccagga    2160
aggccgcacc gtgaaagagg cggctgcact gcttggcgtg catcgctcga ccctgtaccg    2220
cgcacttgag cgcagcgagg aagtgacgcc caccgaggcc aggcggcgcg gtgccttccg    2280
tgaggacgca ttgaccgagg ccgacgccct ggcggccgcc gagaatgaac gccaagagga    2340
acaagcatga aaccgcacca ggacggccag gacgaaccgt ttttcattac cgaagagatc    2400
gaggcggaga tgatcgcggc cgggtacgtg ttcgagccgc ccgcgcacgt ctcaaccgtg    2460
cggctgcatg aaatcctggc cggtttgtct gatgccaagc tggcggcctg ccgggccagc    2520
ttggccgctg aagaaaccga gcgccgccgt ctaaaaggt gatgtgtatt tgagtaaaac     2580
agcttgcgtc atgcggtcgc tgcgtatatg atgcgatgag taaataaaca aatacgcaag    2640
```

```
gggaacgcat gaaggttatc gctgtactta accagaaagg cgggtcaggc aagacgacca    2700
tcgcaaccca tctagcccgc gccctgcaac tcgccggggc cgatgttctg ttagtcgatt    2760
ccgatcccca gggcagtgcc cgcgattggg cggccgtgcg ggaagatcaa ccgctaaccg    2820
ttgtcggcat cgaccgcccg acgattgacc gcgacgtgaa ggccatcggc cggcgcgact    2880
tcgtagtgat cgacggagcg ccccaggcgg cggacttggc tgtgtccgcg atcaaggcag    2940
ccgacttcgt gctgattccg gtgcagccaa gcccttacga catatgggcc accgccgacc    3000
tggtggagct ggttaagcag cgcattgagg tcacggatgg aaggctacaa gcggcctttg    3060
tcgtgtcgcg ggcgatcaaa ggcacgcgca tcggcggtga ggttgccgag gcgctggccg    3120
ggtacgagct gcccattctt gagtcccgta tcacgcagcg cgtgagctac ccaggcactg    3180
ccgccgccgg cacaaccgtt cttgaatcag aacccgaggg cgacgctgcc cgcgaggtcc    3240
aggcgctggc cgctgaaatt aaatcaaaac tcatttgagt taatgaggta aagagaaaat    3300
gagcaaaagc acaaacacgc taagtgccgg ccgtccgagc gcacgcagca gcaaggctgc    3360
aacgttggcc agcctggcag acacgccagc catgaagcgg gtcaactttc agttgccggc    3420
ggaggatcac accaagctga agatgtacgc ggtacgccaa gcaagacca ttaccgagct    3480 gctatctgaa tacatcgcgc agctaccaga gtaaatgagc aaatgaataa atgagtagat    3540
gaattttagc ggctaaagga ggcggcatgg aaaatcaaga acaaccaggc accgacgccg    3600
tggaatgccc catgtgtgga ggaacgggcg gttggccagg cgtaagcggc tgggttgtct    3660
gccggccctg caatggcact ggaaccccca agcccgagga tcggcgtgac ggtcgcaaa    3720 ccatccggcc cggtacaaat cggcgcggcg ctgggtgatg acctggtgga agttgaag    3780 gccgcgcagg ccgcccagcg gcaacgcatc gaggcagaag cacgccccgg tgaatcgtgg    3840
caagcggccg ctgatcgaat ccgcaaagaa tcccggcaac cgccggcagc cggtgcgccg    3900
tcgattagga agccgcccaa gggcgacgag caaccagatt ttttcgttcc gatgctctat    3960
gacgtgggca cccgcgatag tcgcagcatc atggacgtgg ccgttttccg tctgtcgaag    4020
cgtgaccgac gagctggcga ggtgatccgc tacgagcttc cagacgggca cgtagaggtt    4080
tccgcagggc cggccggcat ggccagtgtg tgggattacg acctggtact gatggcggtt    4140
tcccatctaa ccgaatccat gaaccgatac cgggaaggga agggagacaa gcccggccgc    4200
gtgttccgtc cacacgttgc ggacgtactc aagttctgcc ggcgagccga tggcggaaag    4260
cagaaagacg acctggtaga aacctgcatt cggttaaaca ccacgcacgt tgccatgcag    4320
cgtacgaaga aggccaagaa cggccgcctg gtgacggtat ccgagggtga agccttgatt    4380
agccgctaca agatcgtaaa gagcgaaacc gggcggccgg agtacatcga tcgagcta    4440 gctgattgga tgtaccgcga gatcacagaa ggcaagaacc cggacgtgct gacggttcac    4500
cccgattact ttttgatcga tcccggcatc ggccgttttc tctaccgcct ggcacgccgc    4560
gccgcaggca aggcagaagc cagatggttg ttcaagacga tctacgaacg cagtggcagc    4620
gccggagagt tcaagaagtt ctgtttcacc gtgcgcaagc tgatcgggtc aaatgacctg    4680
ccggagtacg atttgaagga ggaggcgggg caggctggcc cgatcctagt catgcgctac    4740
cgcaacctga tcgagggcga agcatccgcc ggttcctaat gtacgagca gatgctaggg    4800 caaattgccc tagcaggga aaaggtcga aaggtctct ttcctgtgga tagcacgtac    4860
attgggaacc caaagccgta cattgggaac cggaacccgt acattgggaa cccaaagccg    4920
tacattggga accggtcaca catgtaagtg actgatataa aagagaaaaa aggcgatttt    4980
```

```
tccgcctaaa actctttaaa acttattaaa actcttaaaa cccgcctggc ctgtgcataa    5040
ctgtctggcc agcgcacagc cgaagagctg caaaaagcgc ctaccottcg gtcgctgcgc    5100
tccctacgcc ccgccgcttc gcgtcggcct atcgcggccg ctggccgctc aaaaatggct    5160
ggcctacggc caggcaatct accagggcgc ggacaagccg cgccgtcgcc actcgaccgc    5220
cggcgcccac atcaaggcac cctgcctcgc gcgtttcggt gatgacggtg aaaacctctg    5280
acacatgcag ctcccggaga cggtcacagc ttgtctgtaa gcggatgccg ggagcagaca    5340
agcccgtcag ggcgcgtcag cgggtgttgg cgggtgtcgg ggcgcagcca tgacccagtc    5400
acgtagcgat agcggagtgt atactggctt aactatgcgg catcagagca gattgtactg    5460
agagtgcacc atatgcggtg tgaaataccg cacagatgcg taaggagaaa ataccgcatc    5520
aggcgctctt ccgcttcctc gctcactgac tcgctgcgct cggtcgttcg gctgcggcga    5580
gcggtatcag ctcactcaaa ggcggtaata cggttatcca cagaatcagg ggataacgca    5640
ggaaagaaca tgtgagcaaa aggccagcaa aaggccagga accgtaaaaa ggccgcgttg    5700
ctggcgtttt tccataggct ccgcccccct gacgagcatc acaaaaatcg acgctcaagt    5760
cagaggtggc gaaacccgac aggactataa agataccagg cgtttccccc tggaagctcc    5820
ctcgtgcgct ctcctgttcc gaccctgccg cttaccggat acctgtccgc ctttctccct    5880
tcgggaagcg tggcgctttc tcatagctca cgctgtaggt atctcagttc ggtgtaggtc    5940
gttcgctcca agctgggctg tgtgcacgaa ccccccgttc agcccgaccg ctgcgcctta    6000
tccggtaact atcgtcttga gtccaacccg gtaagacacg acttatcgcc actggcagca    6060
gccactggta acaggattag cagagcgagg tatgtaggcg gtgctacaga gttcttgaag    6120
tggtggccta actacggcta cactagaagg acagtatttg gtatctgcgc tctgctgaag    6180
ccagttacct tcggaaaaag agttggtagc tcttgatccg gcaaacaaac caccgctggt    6240
agcggtggtt tttttgtttg caagcagcag attacgcgca gaaaaaaagg atctcaagaa    6300
gatcctttga tcttttctac ggggtctgac gctcagtgga acgaaaactc acgttaaggg    6360
attttggtca tgcattctag gtactaaaac aattcatcca gtaaaatata atattttatt    6420
ttctcccaat caggcttgat ccccagtaag tcaaaaaata gctcgacata ctgttcttcc    6480
ccgatatcct ccctgatcga ccggacgcag aaggcaatgt cataccactt gtccgccctg    6540
ccgcttctcc caagatcaat aaagccactt actttgccat cttttcacaa gatgttgctg    6600
tctcccaggt cgccgtggga aaagacaagt tcctcttcgg gcttttccgt ctttaaaaaa    6660
tcatacagct cgcgcggatc tttaaatgga gtgtcttctt cccagttttc gcaatccaca    6720
tcggccagat cgttattcag taagtaatcc aattcggcta agcggctgtc taagctattc    6780
gtatagggac aatccgatat gtcgatggag tgaaagagcc tgatgcactc cgcatacagc    6840
tcgataatct tttcagggct tgttcatct tcatactctt ccgagcaaag gacgccatcg    6900
gcctcactca tgagcagatt gctccagcca tcatgccgtt caaagtgcag gacctttgga    6960
acaggcagct ttccttccag ccatagcatc atgtcctttt cccgttccac atcataggtg    7020
gtcccttat accggctgtc cgtcattttt aaatataggt tttcattttc tcccaccagc    7080
ttatatacct tagcaggaga cattcctcc gtatctttta cgcagcggta tttttcgatc    7140
agtttttcca attccggtga tattctcatt ttagccattt attatttcct tcctcttttc    7200
tacagtattt aaagataccc caagaagcta attataacaa gacgaactcc aattcactgt    7260
tccttgcatt ctaaaaccttt aaataccaga aaacagcttt ttcaaagttg ttttcaaagt    7320
tggcgtataa catagtatcg acggagccga ttttgaaacc gcggtgatca caggcagcaa    7380
```

```
cgctctgtca tcgttacaat caacatgcta ccctccgcga gatcatccgt gtttcaaacc    7440
cggcagctta gttgccgttc ttccgaatag catcggtaac atgagcaaag tctgccgcct    7500
tacaacggct ctcccgctga cgccgtcccg gactgatggg ctgcctgtat cgagtggtga    7560
ttttgtgccg agctgccggt cggggagctg ttggctggct ggtggcagga tatattgtgg    7620
tgtaaacaaa ttgacgctta gacaacttaa taacacattg cggacgtttt taatgtactg    7680
aattaacgcc gaattaattc gggggatctg gattttagta ctggattttg gttttaggaa    7740
ttagaaattt tattgataga agtattttac aaatacaaat acatactaag ggtttcttat    7800
atgctcaaca catgagcgaa accctatagg aaccctaatt cccttatctg gaactactc    7860 acacattatt atggagaaac tcgagcttgt cgatcgacag atccggtcgg catctactct    7920
atttctttgc cctcggacga gtgctggggc gtcggtttcc actatcggcg agtacttcta    7980
cacagccatc ggtccagacg gccgcgcttc tgcgggcgat ttgtgtacgc ccgacagtcc    8040
cggctccgga tcggacgatt gcgtcgcatc gaccctgcgc caagctgca tcatcgaaat    8100 tgccgtcaac caagctctga tagagttggt caagaccaat gcggagcata tacgcccgga    8160
gtcgtggcga tcctgcaagc tccggatgcc tccgctcgaa gtagcgcgtc tgctgctcca    8220
tacaagccaa ccacggcctc cagaagaaga tgttggcgac ctcgtattgg gaatccccga    8280
acatcgcctc gctccagtca atgaccgctg ttatgcggcc attgtccgtc aggacattgt    8340
tggagccgaa atccgcgtgc acgaggtgcc ggacttcggg gcagtcctcg gcccaaagca    8400
tcagctcatc gagagcctgc gcgacggacg cactgacggt gtcgtccatc acagtttgcc    8460
agtgatacac atggggatca gcaatcgcgc atatgaaatc acgccatgta gtgtattgac    8520
cgattccttg cggtccgaat gggccgaacc cgctcgtctg gctaagatcg gccgcagcga    8580
tcgcatccat agcctccgcg accggttgta gaacagcggg cagttcggtt tcaggcaggt    8640
cttgcaacgt gacaccctgt gcacggcggg agatgcaata ggtcaggctc tcgctaaact    8700
ccccaatgtc aagcacttcc ggaatcggga gcgcggccga tgcaaagtgc cgataaacat    8760
aacgatcttt gtagaaacca tcggcgcagc tatttacccg caggacatat ccacgccctc    8820
ctacatcgaa gctgaaagca cgagattctt cgccctccga gagctgcatc aggtcggaga    8880
cgctgtcgaa cttttcgatc agaaacttct cgacagacgt cgcggtgagt tcaggctttt    8940
tcatatctca ttgccccccg ggatctgcga aagctcgaga gagatagatt tgtagagaga    9000
gactggtgat ttcagcgtgt cctctccaaa tgaaatgaac ttccttatat agaggaaggt    9060
cttgcgaagg atagtgggat tgtgcgtcat cccttacgtc agtggagata tcacatcaat    9120
ccacttgctt tgaagacgtg gttggaacgt cttctttttc cacgatgctc ctcgtgggtg    9180
ggggtccatc tttgggacca ctgtcggcag aggcatcttg aacgatagcc tttcctttat    9240
cgcaatgatg gcatttgtag gtgccacctt ccttttctac tgtcctttg atgaagtgac    9300 agatagctgg gcaatggaat ccgaggaggt ttcccgatat tacccttgt tgaaaagtct    9360 caatagccct ttggtcttct gagactgtat ctttgatatt cttggagtag acgagagtgt    9420
cgtgctccac catgttatca catcaatcca cttgctttga agacgtggtt ggaacgtctt    9480 cttttccac gatgctcctc gtgggtgggg gtccatcttt gggaccactg tcggcagagg    9540
catcttgaac gatagccttt cctttatcgc aatgatggca tttgtaggtg ccaccttcct    9600
tttctactgt ccttttgatg aagtgacaga tagctgggca atggaatccg aggaggtttc    9660
ccgatattac cctttgttga aagtctcaa tagccctttg gtcttctgag actgtatctt    9720
```

```
tgatattctt ggagtagacg agagtgtcgt gctccaccat gttggcaagc tgctctagcc    9780
aatacgcaaa ccgcctctcc ccgcgcgttg gccgattcat taatgcagct ggcacgacag    9840
gtttcccgac tggaaagcgg gcagtgagcg caacgcaatt aatgtgagtt agctcactca    9900
ttaggcaccc caggctttac actttatgct tccggctcgt atgttgtgtg gaattgtgag    9960
cggataacaa tttcacacag gaaacagcta tgaccatgat tacgaattcg agctcggtac   10020
ccggggatcc tctagagtcg acctgcaggc atgcaagctt ggcactggcc gtcgttttac   10080
aacgtcgtga ctgggaaaac cctggcgtta cccaacttaa tcgccttgca gcacatcccc   10140
ctttcgccag ctggcgtaat agcgaagagg cccgcaccga tcgcccttcc caacagttgc   10200
gcagcctgaa tggcgaatgc tagagcagct tgagcttgga tcagattgtc gtttcccgcc   10260
ttcagtttag cttcatggag tcaaagattc aaatagagga cctaacagaa ctcgccgtaa   10320
agactggcga acagttcata cagagtctct tacgactcaa tgacaagaag aaaatcttcg   10380
tcaacatggt ggagcacgac acacttgtct actccaaaaa tatcaaagat acagtctcag   10440
aagaccaaag ggcaattgag acttttcaac aaagggtaat atccggaaac ctcctcggat   10500
tccattgccc agctatctgt cactttattg tgaagatagt ggaaaaggaa ggtggctcct   10560
acaaatgcca tcattgcgat aaaggaaagg ccatcgttga agatgcctct gccgacagtg   10620
gtcccaaaga tggaccccca cccacgagga gcatcgtgga aaaagaagac gttccaacca   10680
cgtcttcaaa gcaagtggat tgatgtgata tctccactga cgtaagggat gacgcacaat   10740
cccactatcc ttcgcaagac ccttcctcta tataaggaag ttcatttcat ttggagagaa   10800
cacggggac tcttgac                                                   10817

<210> SEQ ID NO 48
<211> LENGTH: 10811
<212> TYPE: DNA
<213> ORGANISM: Escherichia coli
<220> FEATURE:
<221> NAME/KEY: source
<222> LOCATION: 1..10811
<223> OTHER INFORMATION: mol type=unassigned DNA
      note=pCambia- GFP-xcv-1
      organism=Escherichia coli

<400> SEQUENCE: 48
ccatggtaag taaaggagaa gaacttttca ctggagttgt cccaattctt gttgaattag     60
atggtgatgt taatgggcac aaattttctg tcagtggaga gggtgaaggt gatgcaacat    120
acggaaaact tacccttaaa tttatttgca ctactggaaa actacctgtt ccgtggccaa    180
cacttgtcac tactttctct tatggtgttc aatgcttttc aagataccca gatcatatga    240
agcggcacga cttcttcaag agcgccatgc ctgagggata cgtgcaggag aggaccatct    300
tcttcaagga cgacgggaac tacaagacac gtgctgaagt caagtttgag ggagacaccc    360
tcgtcaacag gatcgagctt aagggaatcg atttcaagga ggacggaaac atcctcggcc    420
acaagttgga atacaactac aactcccaca acgtatacat catggccgac aagcaaaaga    480
acggcatcaa agccaacttc aagacccgcc acaacatcga agacggcggc gtgcaactcg    540
ctgatcatta tcaacaaaat actccaattg gcgatggccc tgtccttta ccagacaacc    600
attacctgtc cacacaatct gccctttcga agatcccaa cgaaaagaga gaccacatgg    660
tccttcttga gtttgtaaca gctgctggga ttacacatgg catggatgaa ctatacaaag    720
cttctagaat gagttactac aatcaacaac aactcctgt tggtgtacct ccaccacaag    780
ggtatccacc agaaggttac ccaaaagatt catacccacc acctggatat ccacagcaag    840
```

```
ggtaccctca acaagggtat ccaccacaag ggtaccctcc acagtatgca cctcagtatg      900
gtgcaccacc tcctcaacaa caacatcaat catctagtag tactggatta ttgcaaggat      960
gtttggctgc tctttgctgt tgctgtgatg catgcttttg aactagtgaa ttcgcggccg     1020
cctgcaggca gctcgaattt ccccgatcgt tcaaacattt ggcaataaag tttcttaaga     1080
ttgaatcctg ttgccggtct tgcgatgatt atcatataat ttctgttgaa ttacgttaag     1140
catgtaataa ttaacatgta atgcatgacg ttatttatga gatgggtttt tatgattaga     1200
gtcccgcaat tatacattta atacgcgata gaaaacaaaa tatagcgcgc aaactaggat     1260
aaattatcgc gcgcggtgtc atctatgtta ctagatcggg aattaaacta tcagtgtttg     1320
acaggatata ttggcgggta aacctaagag aaaagagcgt ttattagaat aacggatatt     1380
taaaagggcg tgaaaaggtt tatccgttcg tccatttgta tgtgcatgcc aaccacaggg     1440
ttcccctcgg gatcaaagta ctttgatcca accctccgc tgctatagtg cagtcggctt     1500
ctgacgttca gtgcagccgt cttctgaaaa cgacatgtcg cacaagtcct aagttacgcg     1560
acaggctgcc gccctgccct tttcctggcg ttttcttgtc gcgtgtttta gtcgcataaa     1620
gtagaatact tgcgactaga accggagaca ttacgccatg aacaagagcg ccgccgctgg     1680
cctgctgggc tatgcccgcg tcagcaccga cgaccaggac ttgaccaacc aacgggccga     1740
actgcacgcg gccggctgca ccaagctgtt ttccgagaag atcaccggca ccaggcgcga     1800
ccgcccggag ctggccagga tgcttgacca cctacgccct ggcgacgttg tgacagtgac     1860
caggctagac cgcctggccc gcagcacccg cgacctactg gacattgccg agcgcatcca     1920
ggaggccggc gcgggcctgc gtagcctggc agagccgtgg gccgacacca ccacgccggc     1980
cggccgcatg gtgttgaccg tgttcgccgg cattgccgag ttcgagcgtt ccctaatcat     2040
cgaccgcacc cggagcgggc gcgaggccgc caagccccga ggcgtgaagt ttggcccccg     2100
ccctaccctc accccggcac agatcgcgca cgcccgcgag ctgatcgacc aggaaggccg     2160
caccgtgaaa gaggcggctg cactgcttgg cgtgcatcgc tcgaccctgt accgcgcact     2220
tgagcgcagc gaggaagtga cgcccaccga ggccaggcgg cgcggtgcct tccgtgagga     2280
cgcattgacc gaggccgacg ccctggcggc cgccgagaat gaacgccaag aggaacaagc     2340
atgaaaccgc accaggacgg ccaggacgaa ccgttttca ttaccgaaga gatcgaggcg     2400
gagatgatcg cggccgggta cgtgttcgag ccgcccgcgc acgtctcaac cgtgcggctg     2460
catgaaatcc tggccggttt gtctgatgcc aagctggcgg cctggccggc cagcttggcc     2520
gctgaagaaa ccgagcgccg ccgtctaaaa aggtgatgtg tatttgagta aaacagcttg     2580
cgtcatgcgg tcgctgcgta tatgatgcga tgagtaaata aacaaatacg caaggggaac     2640
gcatgaaggt tatcgctgta cttaaccaga aaggcgggtc aggcaagacg accatcgcaa     2700
cccatctagc ccgcgccctg caactcgccg gggccgatgt tctgttagtc gattccgatc     2760
cccagggcag tgcccgcgat tgggcggccg tgcgggaaga tcaaccgcta accgttgtcg     2820
gcatcgaccg cccgacgatt gaccgcgacg tgaaggccat cggccggcgc gacttcgtag     2880
tgatcgacgg agcgccccag gcggcggact tggctgtgtc cgcgatcaag gcagccgact     2940
tcgtgctgat tccggtgcag ccaagccctt acgacatatg gccaccgcc gacctggtgg     3000 agctggttaa gcagcgcatt gaggtcacgg atggaaggct acaagcggcc tttgtcgtgt     3060
cgcgggcgat caaaggcacg cgcatcggcg gtgaggttgc cgaggcgctg gccgggtacg     3120
agctgcccat tcttgagtcc cgtatcacgc agcgcgtgag ctacccaggc actgccgccg     3180
```

```
ccggcacaac cgttcttgaa tcagaacccg agggcgacgc tgcccgcgag gtccaggcgc    3240
tggccgctga aattaaatca aaactcattt gagttaatga ggtaaagaga aaatgagcaa    3300
aagcacaaac acgctaagtg ccggccgtcc gagcgcacgc agcagcaagg ctgcaacgtt    3360
ggccagcctg gcagacacgc cagccatgaa gcgggtcaac tttcagttgc cggcggagga    3420
tcacaccaag ctgaagatgt acgcggtacg ccaaggcaag accattaccg agctgctatc    3480
tgaatacatc gcgcagctac cagagtaaat gagcaaatga ataaatgagt agatgaattt    3540
tagcggctaa aggaggcggc atggaaaatc aagaacaacc aggcaccgac gccgtggaat    3600
gccccatgtg tggaggaacg ggcggttggc caggcgtaag cggctgggtt gtctgccggc    3660
cctgcaatgg cactggaacc cccaagcccg aggaatcggc gtgacggtcg caaaccatcc    3720
ggcccggtac aaatcggcgc ggcgctgggt gatgacctgg tggagaagtt gaaggccgcg    3780
caggccgccc agcggcaacg catcgaggca gaagcacgcc ccggtgaatc gtggcaagcg    3840
gccgctgatc gaatccgcaa agaatcccgg caaccgccgg cagccggtgc gccgtcgatt    3900
aggaagccgc ccaagggcga cgagcaacca gattttttcg ttccgatgct ctatgacgtg    3960
ggcacccgcg atagtcgcag catcatggac gtggccgttt ccgtctgtc gaagcgtgac     4020 cgacgagctg gcgaggtgat ccgctacgag cttccagacg gcacgtaga ggtttccgca     4080 gggccggccg gcatggccag tgtgtgggat tacgacctgg tactgatggc ggtttcccat    4140
ctaaccgaat ccatgaaccg ataccgggaa gggaagggga caagcccgg ccgcgtgttc      4200 cgtccacacg ttgcggacgt actcaagttc tgccggcgag ccgatggcgg aaagcagaaa    4260
gacgacctgg tagaaacctg cattcggtta aacaccacgc acgttgccat gcagcgtacg    4320
aagaaggcca agaacggccg cctggtgacg gtatccgagg gtgaagcctt gattagccgc    4380
tacaagatcg taaagagcga aaccgggcgg ccggagtaca tcgagatcga gctagctgat    4440
tggatgtacc gcgagatcac agaaggcaag aacccggacg tgctgacggt tcaccccgat    4500 tacttttgtga tcgatcccgg catcggccgt tttctctacc gcctggcacg ccgcgccgca    4560
ggcaaggcag aagccagatg gttgttcaag acgatctacg aacgcagtgg cagcgccgga   4620
gagttcaaga agttctgttt caccgtgcgc aagctgatcg ggtcaaatga cctgccggag    4680
tacgatttga aggaggaggc ggggcaggct ggcccgatcc tagtcatgcg ctaccgcaac    4740
ctgatcgagg gcgaagcatc cgccggttcc taatgtacgg agcagatgct agggcaaatt    4800
gccctagcag gggaaaaagg tcgaaaaggt ctctttcctg tggatagcac gtacattggg    4860
aacccaaagc cgtacattgg gaaccggaac ccgtacattg ggaacccaaa gccgtacatt    4920
gggaaccggt cacacatgta agtgactgat ataaaagaga aaaaggcga ttttccgcc      4980 taaaactctt taaaacttat taaaactctt aaaacccgcc tggcctgtgc ataactgtct    5040
ggccagcgca cagccgaaga gctgcaaaaa gcgcctaccc ttcggtcgct gcgctcccta    5100
cgccccgccg cttcgcgtcg gcctatcgcg gccgctggcc gctcaaaaat ggctggccta    5160
cggccaggca atctaccagg gcgcggacaa gccgcgccgt cgccactcga ccgcggcgc     5220 ccacatcaag gcaccctgcc tcgcgcgttt cggtgatgac ggtgaaaacc tctgacacat    5280
gcagctcccg gagacggtca cagcttgtct gtaagcggat gccggagca gacaagcccg     5340 tcagggcgcg tcagcgggtg ttggcgggtg tcggggcgca gccatgaccc agtcacgtag    5400
cgatagcgga gtgtatactg gcttaactat gcggcatcag agcagattgt actgagagtg    5460
caccatatgc ggtgtgaaat accgcacaga tgcgtaagga gaaaataccg catcaggcgc    5520
tcttccgctt cctcgctcac tgactcgctg cgctcggtcg ttcggctgcg gcgagcggta    5580
```

```
tcagctcact caaaggcggt aatacggtta tccacagaat cagggataa cgcaggaaag    5640 aacatgtgag caaaaggcca gcaaaaggcc aggaaccgta aaaaggccgc gttgctggcg    5700 ttttccata ggctccgccc ccctgacgag catcacaaaa atcgacgctc aagtcagagg    5760
tggcgaaacc cgacaggact ataaagatac caggcgtttc ccctggaag ctccctcgtg    5820 cgctctcctg ttccgaccct gccgcttacc ggatacctgt ccgcctttct cccttcggga    5880
agcgtggcgc tttctcatag ctcacgctgt aggtatctca gttcggtgta ggtcgttcgc    5940
tccaagctgg gctgtgtgca cgaacccccc gttcagcccg accgctgcgc cttatccggt    6000
aactatcgtc ttgagtccaa cccggtaaga cacgacttat cgccactggc agcagccact    6060
ggtaacagga ttagcagagc gaggtatgta ggcggtgcta cagagttctt gaagtggtgg    6120
cctaactacg gctacactag aaggacagta tttggtatct gcgctctgct gaagccagtt    6180
accttcggaa aaagagttgg tagctcttga tccggcaaac aaaccaccgc tggtagcggt    6240 ggttttttg tttgcaagca gcagattacg cgcagaaaaa aaggatctca agaagatcct    6300
ttgatctttt ctacggggtc tgacgctcag tggaacgaaa actcacgtta agggattttg    6360
gtcatgcatt ctaggtacta aaacaattca tccagtaaaa tataatattt tattttctcc    6420
caatcaggct tgatccccag taagtcaaaa aatagctcga catactgttc ttccccgata    6480
tcctccctga tcgaccggac gcagaaggca atgtcatacc acttgtccgc cctgccgctt    6540
ctcccaagat caataaagcc acttactttg ccatctttca caagatgtt gctgtctccc    6600 aggtcgccgt gggaaaagac aagttcctct tcgggctttt ccgtctttaa aaatcatac    6660 agctcgcgcg gatctttaaa tggagtgtct tcttcccagt tttcgcaatc cacatcggcc    6720
agatcgttat tcagtaagta atccaattcg gctaagcggc tgtctaagct attcgtatag    6780
ggacaatccg atatgtcgat ggagtgaaag agcctgatgc actccgcata cagctcgata    6840
atcttttcag ggctttgttc atcttctac tcttccgagc aaaggacgcc atcggcctca    6900
ctcatgagca gattgctcca gccatcatgc cgttcaaagt gcaggacctt tggaacaggc    6960
agctttcctt ccagccatag catcatgtcc ttttcccgtt ccacatcata ggtggtccct    7020
ttataccggc tgtccgtcat ttttaaatat aggttttcat tttctcccac cagcttatat    7080
accttagcag gagacattcc ttccgtatct tttacgcagc ggtattttc gatcagtttt    7140 ttcaattccg gtgatattct cattttagcc atttattatt ccttcctct tttctacagt    7200 atttaaagat accccaagaa gctaattata acaagacgaa ctccaattca ctgttccttg    7260
cattctaaaa ccttaaatac cagaaaacag cttttcaaa gttgttttca agttggcgt    7320 ataacatagt atcgacggag ccgatttga aaccgcggtg atcacaggca gcaacgctct    7380
gtcatcgtta caatcaacat gctaccctcc gcgagatcat ccgtgtttca aacccggcag    7440
cttagttgcc gttcttccga atagcatcgg taacatgagc aaagtctgcc gccttacaac    7500
ggctctcccg ctgacgccgt cccggactga tgggctgcct gtatcgagtg gtgattttgt    7560
gccgagctgc cggtcgggga gctgttggct ggctggtggc aggatatatt gtggtgtaaa    7620
caaattgacg cttagacaac ttaataacac attgcggacg ttttaatgt actgaattaa    7680 cgccgaatta attcggggga tctggatttt agtactggat tttggtttta ggaattagaa    7740 atttattga tagaagtatt ttacaaatac aaatacatac taagggtttc ttatatgctc    7800
aacacatgag cgaaacccta taggaaccct aattcctta tctgggaact actcacacat    7860
tattatggag aaactcgagc ttgtcgatcg acagatccgg tcggcatcta ctctatttct    7920
```

```
ttgccctcgg acgagtgctg gggcgtcggt ttccactatc ggcgagtact tctacacagc    7980
catcggtcca gacggccgcg cttctgcggg cgatttgtgt acgcccgaca gtcccggctc    8040
cggatcggac gattgcgtcg catcgaccct gcgcccaagc tgcatcatcg aaattgccgt    8100
caaccaagct ctgatagagt tggtcaagac caatgcggag catatacgcc cggagtcgtg    8160
gcgatcctgc aagctccgga tgcctccgct cgaagtagcg cgtctgctgc tccatacaag    8220
ccaaccacgg cctccagaag aagatgttgg cgacctcgta ttgggaatcc ccgaacatcg    8280
cctcgctcca gtcaatgacc gctgttatgc ggccattgtc cgtcaggaca ttgttggagc    8340
cgaaatccgc gtgcacgagg tgccggactt cggggcagtc ctcggcccaa agcatcagct    8400
catcgagagc ctgcgcgacg gacgcactga cggtgtcgtc catcacagtt tgccagtgat    8460
acacatgggg atcagcaatc gcgcatatga aatcacgcca tgtagtgtat tgaccgattc    8520
cttgcggtcc gaatgggccg aacccgctcg tctggctaag atcggccgca gcgatcgcat    8580
ccatagcctc cgcgaccggt tgtagaacag cgggcagttc ggtttcaggc aggtcttgca    8640
acgtgacacc ctgtgcacgg cgggagatgc aataggtcag gctctcgcta aactccccaa    8700
tgtcaagcac ttccggaatc gggagcgcgg ccgatgcaaa gtgccgataa acataacgat    8760 cttttgtagaa accatcggcg cagctatttta cccgcaggac atatccacgc cctcctacat    8820
cgaagctgaa agcacgagat tcttcgccct ccgagagctg catcaggtcg gagacgctgt    8880
cgaacttttc gatcagaaac ttctcgacag acgtcgcggt gagttcaggc ttttcatat    8940 ctcattgccc cccgggatct gcgaaagctc gagagagata gatttgtaga gagagactgg    9000
tgatttcagc gtgtcctctc caaatgaaat gaacttcctt atatagagga aggtcttgcg    9060
aaggatagtg ggattgtgcg tcatcccttA cgtcagtgga gatatcacat caatccactt    9120
gctttgaaga cgtggttgga acgtcttctt tttccacgat gctcctcgtg ggtgggggtc    9180
catctttggg accactgtcg gcagaggcat cttgaacgat agccttcct ttatcgcaat     9240 gatggcattt gtaggtgcca ccttcctttt ctactgtcct tttgatgaag tgacagatag    9300
ctgggcaatg gaatccgagg aggtttcccg atattaccct ttgttgaaaa gtctcaatag    9360 cccttttggtc ttctgagact gtatctttga tattcttgga gtagacgaga gtgtcgtgct    9420
ccaccatgtt atcacatcaa tccacttgct ttgaagacgt ggttggaacg tcttcttttt    9480
ccacgatgct cctcgtgggt gggggtccat ctttgggacc actgtcggca gaggcatctt    9540
gaacgatagc ctttccttta tcgcaatgat ggcatttgta ggtgccacct tccttttcta    9600
ctgtcctttt gatgaagtga cagatagctg gcaatggaa tccgaggagg tttcccgata    9660 ttacccttttg ttgaaaagtc tcaatagccc tttggtcttc tgagactgta tctttgatat    9720
tcttggagta gacgagagtg tcgtgctcca ccatgttggc aagctgctct agccaatacg    9780
caaaccgcct ctccccgcgc gttggccgat tcattaatgc agctggcacg acaggtttcc    9840
cgactggaaa gcgggcagtg agcgcaacgc aattaatgtg agttagctca ctcattaggc    9900
accccaggct ttacacttta tgcttccggc tcgtatgttg tgtggaattg tgagcggata    9960
acaatttcac acaggaaaca gctatgacca tgattacgaa ttcgagctcg gtacccgggg   10020
atcctctaga gtcgacctgc aggcatgcaa gcttggcact ggccgtcgtt ttacaacgtc   10080
gtgactggga aaaccctggc gttacccaac ttaatcgcct tgcagcacat ccccctttcg   10140
ccagctggcg taatagcgaa gaggcccgca ccgatcgccc ttcccaacag ttgcgcagcc   10200
tgaatggcga atgctagagc agcttgagct tggatcagat tgtcgtttcc cgccttcagt   10260
ttagcttcat ggagtcaaag attcaaatag aggacctaac agaactcgcc gtaaagactg   10320
```

-continued

```
gcgaacagtt catacagagt ctcttacgac tcaatgacaa gaagaaaatc ttcgtcaaca    10380
tggtggagca cgacacactt gtctactcca aaaatatcaa agatacagtc tcagaagacc    10440
aaagggcaat tgagactttt caacaaaggg taatatccgg aaacctcctc ggattccatt    10500
gcccagctat ctgtcacttt attgtgaaga tagtggaaaa ggaaggtggc tcctacaaat    10560
gccatcattg cgataaagga aaggccatcg ttgaagatgc ctctgccgac agtggtccca    10620
aagatggacc cccacccacg aggagcatcg tggaaaaaga agacgttcca accacgtctt    10680
caaagcaagt ggattgatgt gatatctcca ctgacgtaag ggatgacgca caatcccact    10740
atccttcgca agaccctt cc tctatataag gaagttcatt tcatttggag agaacacggg    10800
ggactcttga c                                                         10811
```

<210> SEQ ID NO 49
<211> LENGTH: 3297
<212> TYPE: DNA
<213> ORGANISM: Solanum lycopersicum
<220> FEATURE:
<221> NAME/KEY: source
<222> LOCATION: 1..3297
<223> OTHER INFORMATION: mol type=unassigned DNA
      note=SlXcv-1A
      organism=Solanum lycopersicum
<220> FEATURE:
<221> NAME/KEY: CDS
<222> LOCATION: join(1001..1052,1157..1334,2252..2294)
<223> OTHER INFORMATION: transl table=1
<220> FEATURE:
<221> NAME/KEY: 5'UTR
<222> LOCATION: 918..1000
<220> FEATURE:
<221> NAME/KEY: exon
<222> LOCATION: join(918..1052,1157..1334,2252..2520)
<220> FEATURE:
<221> NAME/KEY: mRNA
<222> LOCATION: join(918..1052,1157..1334,2252..2520)
<220> FEATURE:
<221> NAME/KEY: intron
<222> LOCATION: join(1053..1156,1335..2251)
<220> FEATURE:
<221> NAME/KEY: 3'UTR
<222> LOCATION: 2295..2520
<220> FEATURE:
<221> NAME/KEY: polyA site
<222> LOCATION: 2520

<400> SEQUENCE: 49

```
gagcatctga atatttaagt atgaaaaatc aaaatctcat taataagata aaagtttaaa      60
taatcaactc attgaagcta ttaaaattct cgtcaaattc ttactaatac ataaacaaat     120
atatatttaa aatcacaaat tctaaaagta attttcatcc atctcaaaag cattatttcg     180
ttgtgatttt ttttccttc ccaaaggcgt tgtccactaa gatttgaagt ccttagacaa     240
agcaaaagaa atagcattat gaaagaggat gagatataaa gtgaatttct ttttctctat     300
ttcataaaaa aaactagat atacaaaaga agaaaatgtt tatatttta aaatctgttt     360 gtccataaat tatgcctttt taagtgtgta gttatacaga tccacccact atagcatccc     420
aacaaaactc atgacttcat caatcactat taaaaatttt taataaatta tggagattta     480
tttatatggt cataaaaaaa aacatttcaa taaagacagg ttaaacatta attcttctag     540
ataaatcgtt gatcaacttt tctttggaag aactaataat acagtgtagg tcatatctaa     600
attaaaaaat catcaaaaga tgtaaacagt ttgtcaataa ctaatgaaaa taacaaatta     660
aaataacatg aaaagttaaa tagctgaaaa aaattatgaa atattcaatt tcttttttac     720
```

```
aaacataaca ctgaaaaaaa aattcaattt cttttcgata tttatataac agctcgatta    780
aaattgaata aaatttgaga aaaagattcg gcagtaaaat caaattagga tttcttggaa    840
tgcgcttttt tgctggtcct cgttgtgtcc actttgattt gccttataaa tatcccttct    900
ccactgtgca gcccattatc tttctttgtg tctaagcaaa agcaccaaca gaaactctct    960
ctacagttag atccaaccca aattcttcat taattcaaca atg agt tac tac aat     1015
                                            Met Ser Tyr Tyr Asn
                                            1               5 caa caa caa ccc cct gtt ggt gtg cca cca cca caa g gtaaatcact         1062
Gln Gln Gln Pro Pro Val Gly Val Pro Pro Pro Gln
         10                  15 tcaattcctt tttttctgat tttattttgg taaagttgat gttttatat gtttttttga    1122 tgactagatc tgatggggtt ttgaattttt gtag ga tat ccg cca gaa ggt tac    1176
                                     Gly Tyr Pro Pro Glu Gly Tyr
                                                     20 cca aaa gat gca tac cca cca cca ggg tac cca cag cag ggt tac cct    1224
Pro Lys Asp Ala Tyr Pro Pro Pro Gly Tyr Pro Gln Gln Gly Tyr Pro
25                  30                  35                  40 caa caa ggt tac cca cct caa ggg tac cct cca cag tat gca cct cag    1272
Gln Gln Gly Tyr Pro Pro Gln Gly Tyr Pro Pro Gln Tyr Ala Pro Gln
             45                  50                  55 tat ggt gct cca cct cct cat caa caa caa cag caa tct ggt act ggt    1320
Tyr Gly Ala Pro Pro Pro His Gln Gln Gln Gln Gln Ser Gly Thr Gly
        60                  65                  70 ttc atg gaa gga tg gtatgaacct taaagactca attttatgt tcatatgtta       1374
Phe Met Glu Gly Cys
        75 tgattcagtt acagtaattt gtatgatttt gtttgagaga gatctgtatt gatattggtt   1434 ttttgtagag cggttgagga gattgtttat ctgtcttgtc tgttactatg tgtgtgtttc   1494 ttgttgattt ggtgtgtctt gtcaaaacat gatttctcga attattattg gtctgtttga   1554 tgtttacttt gtgagcactt gtatttaata actatggttc tggacgagtt ctggacgcga   1614 actagaaggg gtccttatca tttgtatgtc tagttgaaca ttaacgcgag caggagagac   1674 aattagaatg cctgaatgat tctctatgtg caaacatagt ccaggccttg ccacaccttt   1734 gatttatct ctgactgctg aaatcgcgcc cctatcatac ttcagactgg aagggggtgc    1794 atggactaga cataacttgt gttgctttgt ctatagctat aggttttcca ctgttgctgc   1854 tgcaataaga caataatgac ctcttatcaa agaaatctac actgtcacgt taattgtttc   1914 ttcgttgtaa tagactatgg gagtatcctt gttgatgctc cattccactg taagataagt   1974 agttaactga tctttcaaaa caatcacata attgtcatat taatcacacg tttaagttat   2034 cgcagtgcca gtgaaccaat tagacaatgg acgtggtctt ggctacccta aattttcata   2094 gaatatagtg gtggtctttc acatttcaac agctttgtga ttttctgttt taggcgttcc   2154 ttctttcttg tagcctctcc tcattttatt tgagcttgct gtatttgtta tttccggtgg   2214 gggactaatc attggttgtt atattttgt tttgcag t ttg gct gct ctg tgc      2267
                                         Leu Ala Ala Leu Cys
                                                      80 tgt tgc tgt ctc ttg gat gca tgc ttt tgatgctgta aatgatctgt           2314
Cys Cys Cys Leu Leu Asp Ala Cys Phe
         85                  90 gccatgtgtt ggtggcaaaa gtttattaaa ccaattctat catagtctag actttctctt   2374
tttgtgtttg tctttggtgt cctgtactgt ccttgataaa taatttgata ttaaaatga    2434 cgatgcacct tgttatggtg ggagaattca agtgtctatt tgccaattta tacattattg   2494
```

```
tgcaatgcaa gagattctat ttttttaaaa tcttggttgt ctatatgtga atgcgacctt    2554
gctcttaggt tatatatgct gctgatttct atttactgtg tgggcgatca ccattttttg    2614
ggtttaaagt ttattatact gacttgttag acgcccaaag tataaccaat tgagtggtga    2674
aatacttcaa caagttggca agttgtaaaa tcttctgggt gttagtatat cctacaacag    2734
gcttgtgggg tgcctagtat gtttcttaat ttagaccata atgaaagtcc gccaaaacct    2794
ttaatccttc atcttatgct ttgttggtgg gcaggtgaca tatattttgt agaacacaac    2854
cagacttgga ctcagccgtt ggttcttgat ccttgtgctt atgcaaaccg aataggtaat    2914
agaaataggt tcttttgtgc catagattca tatataaagg actttactaa aaacaatcaa    2974
aggttataaa atataacgac aagcaaaact caaaagacca ccccaaaagt aggcccattt    3034
atgtgaatgc ctttgagatt ttcttcagca gatgacccat taggatgttg ggttgggccc    3094
ttaaaatcta gaaacctttt cctctttgct tcctaaattg catcaaagct cttgttcgaa    3154
tttcacttgc tatttgaaca agtggaaaat catttcatat ttcacaatag agaagggtag    3214
aacctctttg tacgctttaa taacgtgcaa tagtgaatta ttattcatcc gataataatg    3274
atttatttgg aaaaactttt aac                                            3297

<210> SEQ ID NO 50
<211> LENGTH: 91
<212> TYPE: PRT
<213> ORGANISM: Solanum lycopersicum
<220> FEATURE:
<223> OTHER INFORMATION: [CDS]:join(1001..1052,1157..1334,2252..2294)
      from SEQ ID NO 49

<400> SEQUENCE: 50

Met Ser Tyr Tyr Asn Gln Gln Gln Pro Pro Val Gly Val Pro Pro Pro
1               5                   10                  15

Gln Gly Tyr Pro Pro Glu Gly Tyr Pro Lys Asp Ala Tyr Pro Pro Pro
            20                  25                  30

Gly Tyr Pro Gln Gln Gly Tyr Pro Gln Gln Gly Tyr Pro Pro Gln Gly
        35                  40                  45

Tyr Pro Pro Gln Tyr Ala Pro Gln Tyr Gly Ala Pro Pro Pro His Gln
    50                  55                  60

Gln Gln Gln Gln Ser Gly Thr Gly Phe Met Glu Gly Cys Leu Ala Ala
65                  70                  75                  80

Leu Cys Cys Cys Cys Leu Leu Asp Ala Cys Phe
                85                  90

<210> SEQ ID NO 51
<211> LENGTH: 3638
<212> TYPE: DNA
<213> ORGANISM: Solanum lycopersicum
<220> FEATURE:
<221> NAME/KEY: source
<222> LOCATION: 1..3638
<223> OTHER INFORMATION: mol type=unassigned DNA
      note=SlXcv-1B
      organism=Solanum lycopersicum
<220> FEATURE:
<221> NAME/KEY: CDS
<222> LOCATION: join(1135..1186,1378..1561,2615..2657)
<223> OTHER INFORMATION: transl table=1
<220> FEATURE:
<221> NAME/KEY: 5'UTR
<222> LOCATION: 1025..1134
<220> FEATURE:
<221> NAME/KEY: exon
<222> LOCATION: join(1025..1186,1378..1561,2615..2927)
```

```
<220> FEATURE:
<221> NAME/KEY: mRNA
<222> LOCATION: join(1025..1186,1378..1561,2615..2927)
<220> FEATURE:
<221> NAME/KEY: intron
<222> LOCATION: join(1187..1377,1561..2614)
<220> FEATURE:
<221> NAME/KEY: 3'UTR
<222> LOCATION: 2658..2927
<220> FEATURE:
<221> NAME/KEY: polyA site
<222> LOCATION: 2927

<400> SEQUENCE: 51
cataagctat tggagtggga atgcataaga atgaaaaaac atgtcatggt gctccacccc      60
tctccataac tcaacagtga tatcgggtgg agtcagaatt tttattaata aacttataat    120
ataattaaat aacaagcgaa tgaataagct tacaaaaatt aagcacctac tatatgttat    180
atatttaaca atttggttaa aactttttact cttatcctaa taagtggttt cataaatcgt    240
caataaactc taaaacatac tatataacac aaaatcctaa aaataacata taatggagga    300 aactctttt ctcttccttt tcgatcgtga atcaaataat ttaaaattta attaaatcta    360
taaaatttta cttcctttct caataatact ataaatagat agttcatttt tatttatttt    420
aaataattaa aaataattta attactcatc tataatatat ttttaactat agaattctct    480
aaatattaaa tttattgctc cttttatact ttataaatag attttcactt tcattatcat    540
ttttatcata ttaagaaaaa cttttatttt tattttttatt tcatcctcaa tattaattaa    600
ttattcttca aatcattaat tataatttaa gtctatgcac tatttaatat agaaaattat    660
tatttttatt taggagtact tatttaggtg aacatagcca gtcaatatat gataaataaa    720
ataaaataaa cataagagta atatatatat atagaaaaat aatattctga cactttacgc    780
gcatcacaca cggggtactt ttctagtacc cttggaaaag atcacataat aaattaataa    840
attactaagg ccttgttgga tttaacaaat tatctctgaa ataaattta aaattaatta    900 tttcacaatt actggatata agataaaaaa aatagaataa ttaatttcta actatataaa    960
taaattttga ttttaattat ttcttatccg tctgtagcaa cagagtcgga gagtttcttg    1020
gaatatgctg ggcttagtcc ttgtttgact tgctctataa aacctaacaa ataaaccca    1080 tttctttgtg cataagcaaa aactcaaaac tctcttcaac aagaaatttc aatt atg     1137
                                                                Met
                                                                 1 agt tac tac aat cag cag caa ccc cct gtt ggt gta cca cca cca caa g   1186
Ser Tyr Tyr Asn Gln Gln Gln Pro Pro Val Gly Val Pro Pro Pro Gln
         5                  10                  15 gtaaattgct tcaatttcat ttttttttg atgattatg gtaaagttca tattttata      1246 tattgttttg atgattatg gtgaagttga tgttttata tgttgtttg atgatttgtg      1306 gtaaagttga tgttttata tgttattttg atgattagat ctgatggggt tttggggaat    1366
tttgtaatta g gt  tat cca cca gaa ggt tac tct aaa gat gca tac cca    1415
              Gly Tyr Pro Pro Glu Gly Tyr Ser Lys Asp Ala Tyr Pro
                  20                  25                  30 cca cca ggg tat cct cag caa ggg tat cca cca cag ggt tat cct caa     1463
Pro Pro Gly Tyr Pro Gln Gln Gly Tyr Pro Pro Gln Gly Tyr Pro Gln
                35                  40                  45 caa ggg tat cca cct cca cag tat gca cct cag tat ggt gct cca cct     1511
Gln Gly Tyr Pro Pro Pro Gln Tyr Ala Pro Gln Tyr Gly Ala Pro Pro
            50                  55                  60 cct caa caa cat caa cag caa tct agt agc act gga tta atg caa gga     1559
Pro Gln Gln His Gln Gln Gln Ser Ser Ser Thr Gly Leu Met Gln Gly
```

|     |     |     |     |     |
| --- | --- | --- | --- | --- |
|         | 65            | 70            | 75            |      |
| tg | gtatgcatct | ttacactcgt | gatgttttgt | tatgatttag | ttgtgttgtt | 1611 |
| Cys | | | | | | |
| gaattgtatg | atctgagatt | ttttttggat | tgagttgact | atggatgata | aggtgtgtaa | 1671 |
| tgatttgatt | ttgtcaactg | aatgggtga | ggttagtatg | atctcgggtt | ttgttgacta | 1731 |
| agttgccgag | agacttgttc | atatttgtgt | gtctttcctt | gtttgtctcg | aaaagatctt | 1791 |
| ttgatcatca | aagggggaaa | gtagaagcaa | gggggctag | acctctagac | cttaattgct | 1851 |
| gcatagattc | atcatgttgc | tattagttga | ttttctttga | atattttagc | aacctgtgga | 1911 |
| ttcgatataa | gcaatctagg | ttttttttg | gatgaatttc | ttgaccagtt | ttagtcgaga | 1971 |
| gaagatcaaa | ggaatttgga | gaagaaatgt | ccttttgggg | cagaagctcg | agcaatggaa | 2031 |
| tatccctcgt | gtgttacaca | ttaacacgag | ttggagatcc | aaccgattct | aatgcgtgaa | 2091 |
| tatttttat | gtgccaccat | agtccggtcc | tttccattac | tgttatcaac | gcccttcatt | 2151 |
| ttgtctcttg | ttttcattgt | atctactgat | tcatcaccag | tagcatgcaa | tggaattttc | 2211 |
| aacttgctgt | acaatatcat | gtttctcatt | aaaattctgc | cctgaataca | ctgctcaaat | 2271 |
| tgccggttta | gacttaactt | gctttgtcta | tagctattgt | tttccaactg | ctgctcctat | 2331 |
| agataaaata | atgacctctt | agccaaatca | gtctagagct | aagtttggca | agtaatcca | 2391 |
| cactgccgcc | ttagttgttg | tttctttgtt | tctacctcca | atatcctatg | ttgatgctcc | 2451 |
| ttcccattga | tcaaaccttc | aagttgtcgc | agtgccaatg | aactagtcag | acaatgattc | 2511 |
| ttgattccgt | gatgtttcag | tagcccttt | ttcttttagc | actttgtcat | attatttcga | 2571 |
| atttccagtg | ggactaataa | tggtttgtgg | tattgttttg | cag t | ttg gct gct ctg | 2627 |
| | | | | | Leu Ala Ala Leu | |
| | | | | | 80 | |
| tgc tgt tgc tgt ctc ttg gat gca tgc ttt | tgagggtgta | aatgatctgt | 2677 |
| Cys Cys Cys Cys Leu Leu Asp Ala Cys Phe | | | |
| 85                     90 | | | |
| gccatgtgtt | gatggcaaaa | gtttattgaa | tcaattatat | catagtctag | acttttttct | 2737 |
| ttctgtgttt | tgtcctatac | ttactttgat | aaataatttg | atctttgatg | tgctcaagat | 2797 |
| tccaaagtgt | ttgttttgcc | aaattatagg | tggttggtta | tgtacaatgt | gacagattct | 2857 |
| attttattt | ttttcaatgt | tttggacctc | aaaatattat | atgtgaatca | atgcaccttg | 2917 |
| ctctggttac | aaaatttatg | ctcctgttgt | attaaatgtg | ttagcgaaca | caacgtttgg | 2977 |
| gttaaagccc | cgatggtttc | gaataagagt | gtacactagg | cactattatt | ttcccttaaa | 3037 |
| gtgtaagtca | gtttggatat | aaaagaataa | aatgaaataa | gacattaaaa | ccccctttct | 3097 |
| ttaaactact | agtaaaaatg | tgtatgcaca | tggtgtgttt | taacttgttt | acttactagg | 3157 |
| taattagtga | aggggtaaat | aatagggag | aaagtaagtt | aatttaagat | tttcgcatgt | 3217 |
| aattaacaat | tttattatat | tttagatgtg | tttctatgcc | taaaacctga | aaatcaaaaa | 3277 |
| tgattttttt | taaatagagt | agtgatgcca | ccaatgacaa | ggaacagatc | atataataac | 3337 |
| actccacagc | cacatgctat | tgaatattat | gctcaaagag | ccacatgcta | ttgaatatta | 3397 |
| tactcgatat | acactattaa | catatcggag | tatacctaat | gtttgaagcc | atcatgttat | 3457 |
| gttattcatg | cttcaaatgt | tcagacttaa | ttatttatta | atagagttt | ttagaaaaag | 3517 |
| tgtaatgtat | ataatattgt | gtacttgcta | agtagtgtat | atatattgtg | tagtacataa | 3577 |
| ttgaacaatt | ttttaatatt | gaagtcaacg | ataggagtga | tgaatatggt | gggagcatag | 3637 |
| a | | | | | | 3638 |

```
<210> SEQ ID NO 52
<211> LENGTH: 93
<212> TYPE: PRT
<213> ORGANISM: Solanum lycopersicum
<220> FEATURE:
<223> OTHER INFORMATION: [CDS]:join(1135..1186,1378..1561,2615..2657)
      from SEQ ID NO 51

<400> SEQUENCE: 52

Met Ser Tyr Tyr Asn Gln Gln Pro Pro Val Gly Val Pro Pro Pro
1               5                  10                  15

Gln Gly Tyr Pro Pro Glu Gly Tyr Ser Lys Asp Ala Tyr Pro Pro
                20                  25                  30

Gly Tyr Pro Gln Gln Gly Tyr Pro Pro Gln Gly Tyr Pro Gln Gly
            35                  40                  45

Tyr Pro Pro Pro Gln Tyr Ala Pro Gln Tyr Gly Ala Pro Pro Gln
        50                  55                  60

Gln His Gln Gln Gln Ser Ser Ser Thr Gly Leu Met Gln Gly Cys Leu
65                  70                  75                  80

Ala Ala Leu Cys Cys Cys Cys Leu Leu Asp Ala Cys Phe
                85                  90

<210> SEQ ID NO 53
<211> LENGTH: 22
<212> TYPE: DNA
<213> ORGANISM: Solanum lycopersicum
<220> FEATURE:
<221> NAME/KEY: source
<222> LOCATION: 1..22
<223> OTHER INFORMATION: mol type=unassigned DNA
      note=Pr SlProm1AF3
      organism=Solanum lycopersicum

<400> SEQUENCE: 53
aaaggcgttg tccactaaga tt                                              22

<210> SEQ ID NO 54
<211> LENGTH: 23
<212> TYPE: DNA
<213> ORGANISM: Solanum lycopersicum
<220> FEATURE:
<221> NAME/KEY: source
<222> LOCATION: 1..23
<223> OTHER INFORMATION: mol type=unassigned DNA
      note=Pr SlProm1AR3
      organism=Solanum lycopersicum

<400> SEQUENCE: 54
catactgagg tgcatactgt gga                                             23

<210> SEQ ID NO 55
<211> LENGTH: 20
<212> TYPE: DNA
<213> ORGANISM: Solanum lycopersicum
<220> FEATURE:
<221> NAME/KEY: source
<222> LOCATION: 1..20
<223> OTHER INFORMATION: mol type=unassigned DNA
      note=Pr SlTerm1AF3
      organism=Solanum lycopersicum

<400> SEQUENCE: 55
tcttggatgc atgcttttga                                                 20

<210> SEQ ID NO 56
```

```
<211> LENGTH: 20
<212> TYPE: DNA
<213> ORGANISM: Solanum lycopersicum
<220> FEATURE:
<221> NAME/KEY: source
<222> LOCATION: 1..20
<223> OTHER INFORMATION: mol type=unassigned DNA
      note=Pr SlTerm1AR3
      organism=Solanum lycopersicum

<400> SEQUENCE: 56
aagagcaagg tcgcattcac                                              20

<210> SEQ ID NO 57
<211> LENGTH: 20
<212> TYPE: DNA
<213> ORGANISM: Solanum lycopersicum
<220> FEATURE:
<221> NAME/KEY: source
<222> LOCATION: 1..20
<223> OTHER INFORMATION: mol type=unassigned DNA
      note=Pr SlMid1AF1
      organism=Solanum lycopersicum

<400> SEQUENCE: 57
aggatatccg ccagaaggtt                                              20

<210> SEQ ID NO 58
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: mol type=unassigned DNA
      note=Pr SlMid1ABR1
      organism=Solanum lycopersicum

<400> SEQUENCE: 58
gcatgcatca cagcaacagc acagagcagc c                                 31

<210> SEQ ID NO 59
<211> LENGTH: 2352
<212> TYPE: DNA
<213> ORGANISM: Solanum lycopersicum
<220> FEATURE:
<221> NAME/KEY: source
<222> LOCATION: 1..2352
<223> OTHER INFORMATION: mol type=unassigned DNA
      note=Slxcv-1A
      organism=Solanum lycopersicum
<220> FEATURE:
<221> NAME/KEY: CDS
<222> LOCATION: join(799..850,955..1132,2050..2086)
<223> OTHER INFORMATION: transl table=1
<220> FEATURE:
<221> NAME/KEY: 5'UTR
<222> LOCATION: 716..798
<220> FEATURE:
<221> NAME/KEY: exon
<222> LOCATION: join(716..850,955..1132,2050..2312)
<220> FEATURE:
<221> NAME/KEY: mRNA
<222> LOCATION: join(716..850,955..1132,2050..2312)
<220> FEATURE:
<221> NAME/KEY: intron
<222> LOCATION: join(851..954,1133..2049)
<220> FEATURE:
<221> NAME/KEY: 3'UTR
<222> LOCATION: 2087..2312
<220> FEATURE:
<221> NAME/KEY: polyA site
<222> LOCATION: 2312
```

```
<400> SEQUENCE: 59
aaaggcgttg tccactaaga tttgaagtcc ttagacaaag caaaagaaat agcattatga      60
aagaggatga gatataaagt gaatttcttt ttctctattt cataaaaaaa acttagatat     120 acaaagaag aaaatgttta tattttaaa atctgtttgt ccataaatta tgccttttta      180
agtgtgtagt tatacagatc cacccactat agcatcccaa caaaactcat gacttcatca     240
atcactatta aaaattttta ataaattatg gagatttatt tatatggtca taaaaaaaaa     300
catttcaata aagacaggtt aaacattaat tcttctagat aaatcgttga tcaactttc     360 tttggaagaa ctaataatac agtgtaggtc atatctaaat taaaaaatca tcaaaagatg     420
taaacagttt gtcaataact aatgaaaata acaaattaaa ataacatgaa aagttaaata     480
gctgaaaaaa attatgaaat attcaatttc ttttttacaa acataacact gaaaaaaaaa     540
ttcaatttct tttcgatatt tatataacag ctcgattaaa attgaataaa atttgagaaa     600
aagattcggc agtaaaatca aattaggatt tcttggaatg cgcttttttg ctggtcctcg     660
ttgtgtccac tttgatttgc cttataaata tcccttctcc actgtgcagc ccattatctt     720
tctttgtgtc taagcaaaag caccaacaga aactctctct acagttagat ccaacccaaa     780
ttcttcatta attcaaca atg agt tac tac aat caa caa caa ccc cct gtt       831
               Met Ser Tyr Tyr Asn Gln Gln Gln Pro Pro Val
                 1               5                  10 ggt gtg cca cca cca caa g gtaaatcact tcaattcctt tttttctgat            880
Gly Val Pro Pro Pro Gln
            15 tttattttgg taaagttgat gtttttatat gttttttga tgactagatc tgatggggtt      940 ttgaatttt gtag ga tat ccg cca gaa ggt tac cca aaa gat gca tac         989
             Gly Tyr Pro Pro Glu Gly Tyr Pro Lys Asp Ala Tyr
                  20                       25 cca cca cca ggg tac cca cag cag ggt tac cct caa caa ggt tac cca      1037
Pro Pro Pro Gly Tyr Pro Gln Gln Gly Tyr Pro Gln Gln Gly Tyr Pro
 30                  35                  40                  45 cct caa ggg tac cct cca cag tat gca cct cag tat ggt gct cca cct      1085
Pro Gln Gly Tyr Pro Pro Gln Tyr Ala Pro Gln Tyr Gly Ala Pro Pro
             50                  55                  60 cct cat caa caa caa cag caa tct ggt act ggt ttc atg gaa gga tg       1132
Pro His Gln Gln Gln Gln Gln Ser Gly Thr Gly Phe Met Glu Gly Cys
 65                  70                  75 gtatgaacct taaagactca attttatgt tcatatgtta tgattcagtt acagtaattt     1192
gtatgatttt gtttgagaga gatctgtatt gatattggtt ttttgtagag cggttgagga    1252
gattgtttat ctgtcttgtc tgttactatg tgtgtgtttc ttgttgattt ggtgtgtctt    1312
gtcaaaacat gatttctcga attattattg gtctgtttga tgtttacttt gtgagcactt    1372
gtatttaata actatggttc tggacgagtt ctggacgcga actagaaggg gtccttatca    1432
tttgtatgtc tagttgaaca ttaacgcgag caggagagac aattgaaatg cctgaatgat    1492
tctctatgtg caaacatagt ccaggccttg ccacacccttt gattttatct ctgactgctg   1552
aaatcgcgcc cctatcatac ttcagactgg aaggggggtgc atggactaga cataacttgt   1612
gttgctttgt ctatagctat aggttttcca ctgttgctgc tgcaataaga caataatgac    1672
ctcttatcaa agaaatctac actgtcacgt taattgtttc ttcgttgtaa tagactatgg    1732
gagtatcctt gttgatgctc cattccactg taagataagt agttaactga tctttcaaaa    1792
caatcacata attgtcatat taatcacacg tttaagttat cgcagtgcca gtgaaccaat    1852
```

-continued

```
tagacaatgg acgtggtctt ggctacccta aattttcata gaatatagtg gtggtctttc    1912
acatttcaac agctttgtga ttttctgttt taggcgttcc ttctttcttg tagcctctcc    1972 tcatttatt tgagcttgct gtatttgtta tttccggtgg gggactaatc attggttgtt    2032 atattttgt tttgcag t ttg gct gct ctg tgc tgt tgc tgt gat gca tgc     2083
                    Leu Ala Ala Leu Cys Cys Cys Cys Asp Ala Cys
                     80              85 ttt tgatgctgta aatgatctgt gccatgtgtt ggtggcaaaa gtttattaaa          2136
Phe ccaattctat catagtctag actttctctt tttgtgtttg tctttggtgt cctgtactgt    2196
ccttgataaa taatttgata ttaaatatga cgatgcacct tgttatggtg ggagaattca    2256
agtgtctatt tgccaattta tacattattg tgcaatgcaa agagattctat ttttttaaaa   2316 tcttggttgt ctatatgtga atgcgacctt gctctt                              2352
```

<210> SEQ ID NO 60
<211> LENGTH: 89
<212> TYPE: PRT
<213> ORGANISM: Solanum lycopersicum
<220> FEATURE:
<223> OTHER INFORMATION: [CDS]:join(799..850,955..1132,2050..2086) from
      SEQ ID NO 59

<400> SEQUENCE: 60

Met Ser Tyr Tyr Asn Gln Gln Gln Pro Pro Val Gly Val Pro Pro
1               5                   10                  15

Gln Gly Tyr Pro Pro Glu Gly Tyr Pro Lys Asp Ala Tyr Pro Pro Pro
                20                  25                  30

Gly Tyr Pro Gln Gln Gly Tyr Pro Gln Gln Gly Tyr Pro Gln Gly
            35                  40                  45

Tyr Pro Pro Gln Tyr Ala Pro Gln Tyr Gly Ala Pro Pro Pro His Gln
        50                  55                  60

Gln Gln Gln Gln Ser Gly Thr Gly Phe Met Glu Gly Cys Leu Ala Ala
65                  70                  75                  80

Leu Cys Cys Cys Cys Asp Ala Cys Phe
                85

<210> SEQ ID NO 61
<211> LENGTH: 20
<212> TYPE: DNA
<213> ORGANISM: Solanum lycopersicum
<220> FEATURE:
<221> NAME/KEY: source
<222> LOCATION: 1..20
<223> OTHER INFORMATION: mol type=unassigned DNA
      note=Pr SlProm1BF3
      organism=Solanum lycopersicum

<400> SEQUENCE: 61
ctccacccct ctccataact                                                 20

<210> SEQ ID NO 62
<211> LENGTH: 22
<212> TYPE: DNA
<213> ORGANISM: Solanum lycopersicum
<220> FEATURE:
<221> NAME/KEY: source
<222> LOCATION: 1..22
<223> OTHER INFORMATION: mol type=unassigned DNA
      note=Pr-SlProm1BR3
      organism=Solanum lycopersicum

<400> SEQUENCE: 62
ccatactgag gtgcatactg tg                                          22

<210> SEQ ID NO 63
<211> LENGTH: 19
<212> TYPE: DNA
<213> ORGANISM: Solanum lycopersicum
<220> FEATURE:
<221> NAME/KEY: source
<222> LOCATION: 1..19
<223> OTHER INFORMATION: mol type=unassigned DNA
      note=Pr SlTerm1BF3
      organism=Solanum lycopersicum

<400> SEQUENCE: 63
ctgccgcctt agttgttgt                                              19

<210> SEQ ID NO 64
<211> LENGTH: 23
<212> TYPE: DNA
<213> ORGANISM: Solanum lycopersicum
<220> FEATURE:
<221> NAME/KEY: source
<222> LOCATION: 1..23
<223> OTHER INFORMATION: mol type=unassigned DNA
      note=Pr SlTerm1BR3
      organism=Solanum lycopersicum

<400> SEQUENCE: 64
tcccctatta tttacccctt cac                                         23

<210> SEQ ID NO 65
<211> LENGTH: 20
<212> TYPE: DNA
<213> ORGANISM: Solanum lycopersicum
<220> FEATURE:
<221> NAME/KEY: source
<222> LOCATION: 1..20
<223> OTHER INFORMATION: mol type=unassigned DNA
      note=Pr SlMid1BF1
      organism=Solanum lycopersicum

<400> SEQUENCE: 65
aggttatcca ccagaaggtt                                             20

<210> SEQ ID NO 66
<211> LENGTH: 3128
<212> TYPE: DNA
<213> ORGANISM: Solanum lycopersicum
<220> FEATURE:
<221> NAME/KEY: source
<222> LOCATION: 1..3128
<223> OTHER INFORMATION: mol type=unassigned DNA
      note=Slxcv-1B
      organism=Solanum lycopersicum
<220> FEATURE:
<221> NAME/KEY: CDS
<222> LOCATION: join(1084..1135,1327..1510,2564..2600)
<223> OTHER INFORMATION: transl table=1
<220> FEATURE:
<221> NAME/KEY: 5'UTR
<222> LOCATION: 974..1083
<220> FEATURE:
<221> NAME/KEY: exon
<222> LOCATION: join(974..1135,1326..1510,2564..2870)
<220> FEATURE:
<221> NAME/KEY: mRNA
<222> LOCATION: join(974..1135,1327..1510,2564..2870)
<220> FEATURE:
<221> NAME/KEY: intron
<222> LOCATION: join(1136..1326,1511..2563)
<220> FEATURE:

```
<221> NAME/KEY: 3'UTR
<222> LOCATION: 2601..2870
<220> FEATURE:
<221> NAME/KEY: polyA site
<222> LOCATION: 2870

<400> SEQUENCE: 66
ctccacccct ctccataact caacagtgat atcgggtgga gtcagaattt ttattaataa      60
acttataata taattaaata acaagcgaat gaataagctt acaaaaatta agcacctact     120
atatgttata tatttaacaa tttggttaaa acttttactc ttatcctaat aagtggtttc     180
ataaatcgtc aataaactct aaaacatact atataacaca aaatcctaaa aataacatat     240
aatggaggaa actctttttc tcttcctttt cgatcgtgaa tcaaataatt taaaatttaa     300
ttaaatctat aaaattttac ttcctttctc aataatacta taaatagata gttcattttt     360
atttatttta aataattaaa aataatttaa ttactcatct ataatatatt tttaactata     420
gaattctcta atattaaat ttattgctcc ttttatactt tataaataga ttttcacttt      480
cattatcatt tttatcatat taagaaaaac ttttattttt atttttatt catcctcaat      540 attaattaat tattcttcaa atcattaatt ataatttaag tctatgcact atttaatata     600
gaaaattatt attttatt aggagtactt atttaggtga acatagccag tcaatatatg       660
ataaataaaa taaataaac ataagagtaa tatatatata tagaaaaata atattctgac      720
actttacgcg catcacacac ggggtacttt tctagtaccc ttggaaaaga tcacataata     780
aattaataaa ttactaaggc cttgttggat ttaacaaatt atctctgaaa taaattttaa     840
aattaattat ttcacaatta ctggatataa gataaaaaaa atagaataat taatttctaa     900
ctatataaat aaattttgat tttaattatt tcttatccgt ctgtagcaac agagtcggag     960
agtttcttgg aatatgctgg gcttagtcct tgtttgactt gctctataaa acctaacaaa    1020 taaacccccat ttctttgtgc ataagcaaaa actcaaaact ctcttcaaca agaaatttca   1080 att atg agt tac tac aat cag cag caa ccc cct gtt ggt gta cca cca     1128
    Met Ser Tyr Tyr Asn Gln Gln Gln Pro Pro Val Gly Val Pro Pro
    1               5                  10                 15 cca caa g gtaaattgct tcaatttcat tttttttttg atgatttatg gtaaagttca    1185
Pro Gln tattttttata tattgttttg atgatttatg gtgaagttga tgttttttata tgttgttttg     1245 atgatttgtg gtaaagttga tgttttttata tgttattttg atgattagat ctgatggggt    1305
tttggggaat tttgtaatta g gt  tat cca cca gaa ggt tac tct aaa gat      1355
                          Gly Tyr Pro Pro Glu Gly Tyr Ser Lys Asp
                                20                  25 gca tac cca cca cca ggg tat cct cag caa ggg tat cca cca cag ggt     1403
Ala Tyr Pro Pro Pro Gly Tyr Pro Gln Gln Gly Tyr Pro Pro Gln Gly
           30                  35                  40 tat cct caa caa ggg tat cca cct cca cag tat gca cct cag tat ggt     1451
Tyr Pro Gln Gln Gly Tyr Pro Pro Pro Gln Tyr Ala Pro Gln Tyr Gly
        45                  50                  55 gct cca cct cct caa caa cat caa cag caa tct agt agc act gga tta     1499
Ala Pro Pro Pro Gln Gln His Gln Gln Gln Ser Ser Ser Thr Gly Leu
60                  65                  70                  75 atg caa gga tg gtatgcatct ttacactcgt gatgttttgt tatgatttag            1550
Met Gln Gly Cys ttgtgttgtt gaattgtatg atctgagatt ttttttggat tgagttgact atggatgata    1610
aggtgtgtaa tgatttgatt ttgtcaactg aattgggtga ggttagtatg atctcgggtt    1670
ttgttgacta agttgccgag agacttgttc atatttgtgt gtctttcctt gtttgtctcg    1730
```

```
aaaagatctt tgatcatca aagggggaaa gtagaagcaa ggggggctag acctctagac      1790
cttaattgct gcatagattc atcatgttgc tattagttga ttttctttga atattttagc      1850
aacctgtgga ttcgatataa gcaatctagg ttttttttg gatgaatttc ttgaccagtt      1910
ttagtcgaga gaagatcaaa ggaatttgga gaagaaatgt cctttgggg cagaagctcg       1970 agcaatggaa tatccctcgt gtgttacaca ttaacacgag ttggagatcc aaccgattct      2030
aatgcgtgaa tatttttat gtgccaccat agtccggtcc tttccattac tgttatcaac       2090
gcccttcatt ttgtctcttg ttttcattgt atctactgat tcatcaccag tagcatgcaa      2150
tggaattttc aacttgctgt acaatatcat gtttctcatt aaaattctgc cctgaataca      2210
ctgctcaaat tgccggttta gacttaactt gctttgtcta tagctattgt tttccaactg      2270
ctgctcctat agataaaata atgacctctt agccaaatca gtctagagct aagtttggca      2330
aagtaatcca cactgccgcc ttagttgttg tttctttgtt tctacctcca atatcctatg      2390
ttgatgctcc ttcccattga tcaaaccttc aagttgtcgc agtgccaatg aactagtcag      2450
acaatgattc ttgattccgt gatgtttcag tagccctttt ttcttttagc actttgtcat      2510
attatttcga atttccagtg ggactaataa tggtttgtgg tattgttttg cag t ttg       2567
                                                              Leu
                                                               80 gct gct ctg tgc tgt tgc tgt gat gca tgc ttt tgagggtgta atgatctgt       2620
Ala Ala Leu Cys Cys Cys Cys Asp Ala Cys Phe
            85                  90 gccatgtgtt gatggcaaaa gtttattgaa tcaattatat catagtctag acttttttct      2680
ttctgtgttt tgtcctatac ttactttgat aaataatttg atctttgatg tgctcaagat      2740
tccaaagtgt ttgttttgcc aaattatagg tggttggtta tgtacaatgt gacagattct      2800
atttttattt ttttcaatgt tttggacctc aaaatattat atgtgaatca atgcaccttg      2860
ctctggttac aaatttatgc tcctgttgta ttaaatgtgt tagcgaacac aacgtttggg      2920
ttaaagcccc gatggtttcg aataagagtg tacactaggc actattattt tcccttaaag      2980
tgtaagtcag tttggatata aagaataaa atgaaataag acattaaaac ccccttttctt      3040 taaactacta gtaaaaatgt gtatgcacat ggtgtgtttt aacttgttta cttactaggt      3100
aattagtgaa ggggtaaata ataggggga                                        3128
```

<210> SEQ ID NO 67
<211> LENGTH: 91
<212> TYPE: PRT
<213> ORGANISM: Solanum lycopersicum
<220> FEATURE:
<223> OTHER INFORMATION: [CDS]:join(1084..1135,1327..1510,2564..2600)
      from SEQ ID NO 66

<400> SEQUENCE: 67

Met Ser Tyr Tyr Asn Gln Gln Gln Pro Pro Val Gly Val Pro Pro Pro
1               5                   10                  15

Gln Gly Tyr Pro Pro Glu Gly Tyr Ser Lys Asp Ala Tyr Pro Pro
                20                  25                  30

Gly Tyr Pro Gln Gln Gly Tyr Pro Pro Gln Gly Tyr Pro Gln Gln Gly
            35                  40                  45

Tyr Pro Pro Pro Gln Tyr Ala Pro Gln Tyr Gly Ala Pro Pro Gln
        50                  55                  60

Gln His Gln Gln Gln Ser Ser Ser Thr Gly Leu Met Gln Gly Cys Leu
65                  70                  75                  80

Ala Ala Leu Cys Cys Cys Cys Asp Ala Cys Phe
                85                  90

<210> SEQ ID NO 68
<211> LENGTH: 177
<212> TYPE: DNA
<213> ORGANISM: Solanum lycopersicum
<220> FEATURE:
<221> NAME/KEY: source
<222> LOCATION: 1..177
<223> OTHER INFORMATION: mol type=unassigned DNA
      note=pre-sly-MIR159miRNSpre-miDNA
      organism=Solanum lycopersicum

<400> SEQUENCE: 68
tggagctcct tgaagtccaa caaaaaatct aacaggttaa attgagctgc tgacctatgg    60
attcctcagc cctatctatt tatgatttca acatataga taggttttgg gtttgcatat   120
gtcaggagct ttattttacc ctttgtttga tcatttttg gattgaaggg agctcta     177

<210> SEQ ID NO 69
<211> LENGTH: 177
<212> TYPE: RNA
<213> ORGANISM: Solanum lycopersicum
<220> FEATURE:
<221> NAME/KEY: source
<222> LOCATION: 1..177
<223> OTHER INFORMATION: mol type=unassigned RNA
      note=preSlpre-slyMI159RNA
      organism=Solanum lycopersicum

<400> SEQUENCE: 69
uggagcuccu ugaaguccaa caaaaaaucu aacagguuaa auugagcugc ugaccuaugg    60 auccucagc ccuaucuauu uaugauuuca acauauaga uagguuuugg guuugcauau    120
gucaggagcu uuauuuuacc cuuuguuuga ucauuuuuug gauugaaggg agcucua     177

<210> SEQ ID NO 70
<211> LENGTH: 46
<212> TYPE: DNA
<213> ORGANISM: Solanum lycopersicum
<220> FEATURE:
<221> NAME/KEY: source
<222> LOCATION: 1..46
<223> OTHER INFORMATION: mol type=unassigned DNA
      note=Pr1 SlXe1 pre-amiRNS
      organism=Solanum lycopersicum

<400> SEQUENCE: 70
gtgttgatgt cgattggatg caaaaaatct aacaggttaa attgag               46

<210> SEQ ID NO 71
<211> LENGTH: 45
<212> TYPE: DNA
<213> ORGANISM: Solanum lycopersicum
<220> FEATURE:
<221> NAME/KEY: source
<222> LOCATION: 1..45
<223> OTHER INFORMATION: mol type=unassigned DNA
      note=Pr2 SlXe1 pre-amiRNS
      organism=Solanum lycopersicum

<400> SEQUENCE: 71
gtgttgatgt ctcttggatg aaaatgatca acaaagggt aaaat                45

<210> SEQ ID NO 72
<211> LENGTH: 178
<212> TYPE: DNA

```
<213> ORGANISM: Solanum lycopersicum
<220> FEATURE:
<221> NAME/KEY: source
<222> LOCATION: 1..178
<223> OTHER INFORMATION: mol type=unassigned DNA
      note=pre-SlXe1-amiDNA
      organism=Solanum lycopersicum

<400> SEQUENCE: 72
gtgttgatgt cctttggatg ccaaaaaatc taacaggtta aattgagctg ctgacctatg    60
gattcctcag ccctatctat ttatgatttc aaacatatag ataggttttg ggtttgcata   120
tgtcaggagc tttattttac cctttgtttg atcattttca tccaagagac atcaacac    178

<210> SEQ ID NO 73
<211> LENGTH: 178
<212> TYPE: RNA
<213> ORGANISM: Solanum lycopersicum
<220> FEATURE:
<221> NAME/KEY: source
<222> LOCATION: 1..178
<223> OTHER INFORMATION: mol type=unassigned RNA
      note=pre-SlXe1-amiRNA
      organism=Solanum lycopersicum

<400> SEQUENCE: 73
guguugaugu ccuuuggaug ccaaaaaauc uaacagguua aauugagcug cugaccuaug    60
gauuccucag cccuaucuau uuaugauuuc aaacauauag auagguuuug gguuugcaua   120
ugucaggagc uuuauuuuac ccuuuguuug aucauuuuca uccaagagac aucaacac    178

<210> SEQ ID NO 74
<211> LENGTH: 21
<212> TYPE: RNA
<213> ORGANISM: Solanum lycopersicum
<220> FEATURE:
<221> NAME/KEY: source
<222> LOCATION: 1..21
<223> OTHER INFORMATION: mol type=unassigned RNA
      note=SlXe1-amiRNA
      organism=Solanum lycopersicum

<400> SEQUENCE: 74
ucauccaaga gacaucaaca c                                              21

<210> SEQ ID NO 75
<211> LENGTH: 17
<212> TYPE: DNA
<213> ORGANISM: Solanum lycopersicum
<220> FEATURE:
<221> NAME/KEY: source
<222> LOCATION: 1..17
<223> OTHER INFORMATION: mol type=unassigned DNA
      note=SlXcv-1AB TAL-L
      organism=Solanum lycopersicum

<400> SEQUENCE: 75
tggctgctct gtgctgt                                                   17

<210> SEQ ID NO 76
<211> LENGTH: 17
<212> TYPE: DNA
<213> ORGANISM: Solanum lycopersicum
<220> FEATURE:
<221> NAME/KEY: source
<222> LOCATION: 1..17
<223> OTHER INFORMATION: mol type=unassigned DNA
      note=SlXcv-1A TAL-R
      organism=Solanum lycopersicum
```

<400> SEQUENCE: 76
ttacagcatc aaaagca                                                       17

<210> SEQ ID NO 77
<211> LENGTH: 17
<212> TYPE: DNA
<213> ORGANISM: Solanum lycopersicum
<220> FEATURE:
<221> NAME/KEY: source
<222> LOCATION: 1..17
<223> OTHER INFORMATION: mol type=unassigned DNA
      note=SlXcv-1B TAL-R
      organism=Solanum lycopersicum

<400> SEQUENCE: 77
ttacaccctc aaaagca                                                       17

<210> SEQ ID NO 78
<211> LENGTH: 3859
<212> TYPE: DNA
<213> ORGANISM: Solanum lycopersicum
<220> FEATURE:
<221> NAME/KEY: source
<222> LOCATION: 1..3859
<223> OTHER INFORMATION: mol type=unassigned DNA
      note=SlXcv-1AB TALEN-L
      organism=Solanum lycopersicum

<400> SEQUENCE: 78
ggatcccatt cgtccgcgca ggccaagtcc tgcccgcgag cttctgcccg gaccccaacc         60
ggatagggtt cagccgactg cagatcgtgg ggtgtctgcg cctgctggca gccctctgga       120
tggcttgccc gctcggcgga cggtgtcccg gacccggctg ccatctcccc ctgcgccctc       180
acctgcgttc tcggcgggca gcttcagcga tctgctccgt ccgttcgatc cgtcgcttct       240
tgatacatcg cttcttgatt cgatgcctgc cgtcggcacg ccgcatacag cggctgcccc       300
agcagagtgg gatgaggcgc aatcggctct gcgtgcagcc gatgacccgc cacccaccgt       360
gcgtgtcgct gtcactgccg cgcggccgcc gcgcgcaag ccggcccgc gacggcgtgc         420 tgcgcaaccc tccgacgctt cgccggccgc gcaggtggat ctacgcacgc tcggctacag       480
tcagcagcag caagagaaga tcaaaccgaa ggtgcgttcg acagtggcgc agcaccacga       540
ggcactggtg ggccatgggt ttacacacgc gcacatcgtt gcgctcagcc aacacccggc       600
agcgttaggg accgtcgctg tcacgtatca gcacataatc acggcgttgc cagaggcgac       660
acacgaagac atcgttggcg tcggcaaaca gtggtccggc gcacgcgccc tggaggcctt       720
gctcacggat gcgggggagt tgagaggtcc gccgttacag ttggacacag gccaacttgt       780
gaagattgca aaacgtggcg gcgtgaccgc aatggaggca gtgcatgcat cgcgcaatgc       840
actgacgggt gccccctga acctgacccc ggaccaagtg gtggctatcg ccagcaacgg       900
tggcggcaag caagcgctcg aaacggtgca gcggctgttg ccggtgctgt gccaggacca       960
tggcctgacc ccggaccaag tggtggctat cgccagcaac catggcggca agcaagcgct      1020
cgaaacggtg cagcggctgt tgccggtgct gtgccaggac catggcctga ccccggacca      1080
agtggtggct atcgccagca accatggcgg caagcaagc ctcgaaacgg tgcagcggct       1140
gttgccggtg ctgtgccagg accatggcct gactccggac caagtggtgg ctatcgccag      1200
ccacgatggc ggcaagcaag cgctcgaaac ggtcagcgg ctgttgccgg tgctgtgcca       1260
ggaccatggc ctgaccccgg accaagtggt ggctatcgcc agcaacggtg gcggcaagca      1320

-continued

```
agcgctcgaa acggtgcagc ggctgttgcc ggtgctgtgc caggaccatg gcctgacccc    1380
ggaccaagtg gtggctatcg ccagcaacca tggcggcaag caagcgctcg aaacggtgca    1440
gcggctgttg ccggtgctgt gccaggacca tggcctgact ccggaccaag tggtggctat    1500
cgccagccac gatggcggca agcaagcgct cgaaacggtg cagcggctgt tgccggtgct    1560
gtgccaggac catggcctga ccccggacca agtggtggct atcgccagca acggtggcgg    1620
caagcaagcg ctcgaaacgg tgcagcggct gttgccggtg ctgtgccagg accatggcct    1680
gactccggac caagtggtgg ctatcgccag ccacgatggc ggcaagcaag cgctcgaaac    1740
ggtgcagcgg ctgttgccgg tgctgtgcca ggaccatggc ctgaccccgg accaagtggt    1800
ggctatcgcc agcaacggtg gcggcaagca agcgctcgaa acggtgcagc ggctgttgcc    1860
ggtgctgtgc caggaccatg gcctgacccc ggaccaagtg gtggctatcg ccagcaacca    1920
tggcggcaag caagcgctcg aaacggtgca gcggctgttg ccggtgctgt gccaggacca    1980
tggcctgacc ccggaccaag tggtggctat cgccagcaac ggtggcggca agcaagcgct    2040
cgaaacggtg cagcggctgt tgccggtgct gtgccaggac catggcctga ccccggacca    2100
agtggtggct atcgccagca accatggcgg caagcaagcg ctcgaaacgg tgcagcggct    2160
gttgccggtg ctgtgccagg accatggcct gactccggac caagtggtgg ctatcgccag    2220
ccacgatggc ggcaagcaag cgctcgaaac ggtgcagcgg ctgttgccgg tgctgtgcca    2280
ggaccatggc ctgaccccgg accaagtggt ggctatcgcc agcaacggtg gcggcaagca    2340
agcgctcgaa acggtgcagc ggctgttgcc ggtgctgtgc caggaccatg gcctgacccc    2400
ggaccaagtg gtggctatcg ccagcaacca tggcggcaag caagcgctcg aaacggtgca    2460
gcggctgttg ccggtgctgt gccaggacca tggcctgacc ccggaccaag tggtggctat    2520
cgccagcaac ggtggcggca agcaagcgct cgaaagcatt gtggcccagc tgagccggcc    2580
tgatccggcg ttggccgcgt tgaccaacga ccacctcgtc gccttggcct gcctcggcgg    2640
acgtcctgcc atggatgcag tgaaaaaggg attgccgcac gcgccggaat tgatcagaag    2700
agtcaatcgc cgtattggcg aacgcacgtc ccatcgcgtt gccgactacg cgcaagtggt    2760
tcgcgtgctg gagttttttcc agtgccactc ccacccagcg tacgcatttg atgaggccat    2820
gacgcagttc gggatgagca ggaacggggtt ggtacagctc tttcgcagag tgggcgtcac    2880
cgaactcgaa gcccgcggtg gaacgctccc cccagcctcg cagcgttggg accgtatcct    2940
ccaggcatca gggatgaaaa gggccaaacc gtcccctact tcagctcaaa caccggatca    3000
ggcgtctttg catgcattcg ccgattcgct ggagcgtgac cttgatgcgc ccagcccaat    3060
gcacgaggga gatcagacgc gggcaagcag ccgtaaacgg tcccgatcgg atcgtgctgt    3120
caccggcccc tccgcacagc aggctgtcga ggtgcgcgtt cccgaacagc gcgatgcgct    3180
gcatttgccc ctcagctgga gggtaaaacg cccgcgtacc aggatctggg gcggcctccc    3240
ggatccgata tctagatccc agctagtgaa atctgaattg aagagaagaa aatctgaact    3300
tagacataaa ttgaaatatg tgccacatga atatattgaa ttgattgaaa tcgcaagaaa    3360
ttcaactcag gatagaatcc ttgaaatgaa ggtgatggag ttctttatga aggtttatgg    3420
ttatcgtggt aaacatttgg gtggatcaag gaaaccagac ggagcaattt atactgtcgg    3480
atctcctatt gattacggtg tgatcgttga tactaaggca tattcaggag ttataatcct    3540
tccaattggt caagcagatg aaatgcaaag atatgtcgaa gagaatcaaa caagaaacaa    3600
gcatatcaac cctaatgaat ggtggaaagt ctatccatct tcagtaacag aatttaagtt    3660
cttgtttgtg agtggtcatt tcaaaggaaa ctacaaagct cagcttacaa gattgaatca    3720
```

```
tatcactaat tgtaatggag ctgttcttag tgtagaagag cttttgattg gtggagaaat    3780
gattaaagct ggtacattga cacttgagga agtgagaagg aaatttaata acggtgagat    3840
aaacttttaa taggagctc                                                 3859

<210> SEQ ID NO 79
<211> LENGTH: 3859
<212> TYPE: DNA
<213> ORGANISM: Solanum lycopersicum
<220> FEATURE:
<221> NAME/KEY: source
<222> LOCATION: 1..3859
<223> OTHER INFORMATION: mol type=unassigned DNA
      note=SlXcv-1A TALEN-R
      organism=Solanum lycopersicum

<400> SEQUENCE: 79
ggatcccatt cgtccgcgca ggccaagtcc tgcccgcgag cttctgcccg accccaacc      60 ggatagggtt cagccgactg cagatcgtgg ggtgtctgcg cctgctggca gccctctgga    120
tggcttgccc gctcggcgga cggtgtcccg acccggctg ccatctcccc ctgcgccctc     180
acctgcgttc tcggcgggca gcttcagcga tctgctccgt ccgttcgatc cgtcgcttct    240
tgatacatcg cttcttgatt cgatgcctgc cgtcggcacg ccgcatacag cggctgcccc    300
agcagagtgg gatgaggcgc aatcggctct cgtgcagcc gatgacccgc cacccaccgt     360
gcgtgtcgct gtcactgccg cgcggccgcc gcgcgccaag ccggcccgc gacggcgtgc     420 tgcgcaaccc tccgacgctt cgccggccgc gcaggtggat ctacgcacgc tcggctacag    480
tcagcagcag caagagaaga tcaaaccgaa ggtgcgttcg acagtggcgc agcaccacga    540
ggcactggtg ggccatgggt ttacacacgc gcacatcgtt gcgctcagcc aacacccggc    600
agcgttaggg accgtcgctg tcacgtatca gcacataatc acggcgttgc cagaggcgac    660
acacgaagac atcgttggcg tcggcaaaca gtggtccggc gcacgcgccc tggaggcctt    720
gctcacggat gcgggggagt tgagaggtcc gccgttacag ttggacacag gccaacttgt    780
gaagattgca aaacgtggcg gcgtgaccgc aatggaggca gtgcatgcat cgcgcaatgc    840
actgacgggt gccccctga acctgacccc ggaccaagtg gtggctatcg ccagcaacgg      900
tggcggcaag caagcgctcg aaacggtgca gcggctgttg ccggtgctgt gccaggacca     960
tggcctgacc ccggaccaag tggtggctat cgccagcaac ggtggcggca agcaagcgct    1020
cgaaacggtg cagcggctgt tgccggtgct gtgccaggac catggcctga ccccggacca    1080
agtggtggct atcgccagca acattggcgg caagcaagcc tcgaaacgg tgcagcggct     1140 gttgccggtg ctgtgccagg accatggcct gactccggac caagtggtgg ctatcgccag    1200
ccacgatggc ggcaagcaag cgctcgaaac ggtgcagcgg ctgttgccgg tgctgtgcca    1260
ggaccatggc ctgaccccgg accaagtggt ggctatcgcc agcaacattg gcggcaagca    1320
agcgctcgaa acggtgcagc ggctgttgcc ggtgctgtgc caggaccatg gcctgacccc    1380
ggaccaagtg gtggctatcg ccagcaacca tggcggcaag caagcgctcg aaacggtgca    1440
gcggctgttg ccggtgctgt gccaggacca tggcctgact ccggaccaag tggtggctat    1500
cgccagccac gatggcggca agcaagcgct cgaaacggtg cagcggctgt tgccggtgct    1560
gtgccaggac catggcctga ccccggacca agtggtggct atcgccagca acattggcgg    1620
caagcaagcg ctcgaaacgg tgcagcggct gttgccggtg ctgtgccagg accatggcct    1680
gaccccggac caagtggtgg ctatcgccag caacggtggc ggcaagcaag cgctcgaaac    1740
```

```
ggtgcagcgg ctgttgccgg tgctgtgcca ggaccatggc ctgactccgg accaagtggt    1800
ggctatcgcc agccacgatg gcggcaagca agcgctcgaa acggtgcagc ggctgttgcc    1860
ggtgctgtgc caggaccatg gcctgacccc ggaccaagtg gtggctatcg ccagcaacat    1920
tggcggcaag caagcgctcg aaacggtgca gcggctgttg ccggtgctgt gccaggacca    1980
tggcctgacc ccggaccaag tggtggctat cgccagcaac attggcggca agcaagcgct    2040
cgaaacggtg cagcggctgt tgccggtgct gtgccaggac catggcctga ccccggacca    2100
agtggtggct atcgccagca acattggcgg caagcaagcg ctcgaaacgg tgcagcggct    2160
gttgccggtg ctgtgccagg accatggcct gaccccggac caagtggtgg ctatcgccag    2220
caacattggc ggcaagcaag cgctcgaaac ggtgcagcgg ctgttgccgg tgctgtgcca    2280
ggaccatggc ctgaccccgg accaagtggt ggctatcgcc agcaaccatg gcggcaagca    2340
agcgctcgaa acggtgcagc ggctgttgcc ggtgctgtgc caggaccatg gcctgactcc    2400
ggaccaagtg gtggctatcg ccagccacga tggcggcaag caagcgctcg aaacggtgca    2460
gcggctgttg ccggtgctgt gccaggacca tggcctgacc ccggaccaag tggtggctat    2520
cgccagcaac attggcggca agcaagcgct cgaaagcatt gtggcccagc tgagccggcc    2580
tgatccggcg ttggccgcgt tgaccaacga ccacctcgtc gccttggcct gcctcggcgg    2640
acgtcctgcc atggatgcag tgaaaaaggg attgccgcac gcgccggaat tgatcagaag    2700
agtcaatcgc cgtattggcg aacgcacgtc ccatcgcgtt gccgactacg cgcaagtggt    2760
tcgcgtgctg gagttttttcc agtgccactc ccacccagcg tacgcatttg atgaggccat    2820
gacgcagttc gggatgagca ggaacggggtt ggtacagctc tttcgcagag tgggcgtcac    2880
cgaactcgaa gcccgcggtg gaacgctccc cccagcctcg cagcgttggg accgtatcct    2940
ccaggcatca gggatgaaaa gggccaaacc gtcccctact tcagctcaaa caccggatca    3000
ggcgtctttg catgcattcg ccgattcgct ggagcgtgac cttgatgcgc ccagcccaat    3060
gcacgaggga gatcagacgc gggcaagcag ccgtaaacgg tcccgatcgg atcgtgctgt    3120
caccggcccc tccgcacagc aggctgtcga ggtgcgcgtt cccgaacagc gcgatgcgct    3180
gcatttgccc ctcagctgga gggtaaaacc cccgcgtacc aggatctggg gcggcctccc    3240
ggatccgata tctagatccc agctagtgaa atctgaattg aagagaaga aatctgaact    3300 tagacataaa ttgaaatatg tgccacatga atatattgaa ttgattgaaa tcgcaagaaa    3360
ttcaactcag gatagaatcc ttgaaatgaa ggtgatggag ttctttatga aggtttatgg    3420
ttatcgtggt aaacatttgg gtggatcaag gaaaccagac ggagcaattt atactgtcgg    3480 atctccctatt gattacggtg tgatcgttga tactaaggca tattcaggag ttataatct    3540 tccaattggt caagcagatg aaatgcaaag atatgtcgaa gagaatcaaa caagaaacaa    3600
gcatatcaac cctaatgaat ggtggaaagt ctatccatct tcagtaacag aatttaagtt    3660
cttgtttgtg agtggtcatt tcaaaggaaa ctacaaagct cagcttacaa gattgaatca    3720
tatcactaat tgtaatggag ctgttcttag tgtagaagag cttttgattg gtggagaaat    3780
gattaaagct ggtacattga cacttgagga agtgagaagg aaatttaata acggtgagat    3840
aaacttttaa taggagctc                                                 3859
```

<210> SEQ ID NO 80
<211> LENGTH: 3859
<212> TYPE: DNA
<213> ORGANISM: Solanum lycopersicum
<220> FEATURE:
<221> NAME/KEY: source
<222> LOCATION: 1..3859
<223> OTHER INFORMATION: mol type=unassigned DNA
      note=SlXcv-1B TALEN-R
      organism=Solanum lycopersicum

<400> SEQUENCE: 80

```
ggatcccatt cgtccgcgca ggccaagtcc tgcccgcgag cttctgcccg accccaacc      60
ggatagggtt cagccgactg cagatcgtgg ggtgtctgcg cctgctggca gccctctgga   120
tggcttgccc gctcggcgga cggtgtcccg gacccggctg ccatctcccc ctgcgccctc   180
acctgcgttc tcggcgggca gcttcagcga tctgctccgt ccgttcgatc cgtcgcttct   240
tgatacatcg cttcttgatt cgatgcctgc cgtcggcacg ccgcatacag cggctgcccc   300
agcagagtgg gatgaggcgc aatcggctct gcgtgcagcc gatgacccgc acccaccgt    360
gcgtgtcgct gtcactgccg cgcggccgcc gcgcgcaag ccggcccgc gacggcgtgc     420
tgcgcaaccc tccgacgctt cgccggccgc gcaggtggat ctacgcacgc tcggctacag   480
tcagcagcag caagagaaga tcaaaccgaa ggtgcgttcg acagtggcgc agcaccacga   540
ggcactggtg ggccatgggt ttacacacgc gcacatcgtt gcgctcagcc aacacccggc   600
agcgttaggg accgtcgctg tcacgtatca gcacataatc acggcgttgc cagaggcgac   660
acacgaagac atcgttggcg tcggcaaaca gtggtccggc gcacgcgccc tggaggcctt   720
gctcacggat gcgggggagt tgagaggtcc gccgttacag ttggacacag gccaacttgt   780
gaagattgca aaacgtggcg gcgtgaccgc aatggaggca gtgcatgcat cgcgcaatgc   840
actgacgggt gccccctga acctgacccc ggaccaagtg gtggctatcg ccagcaacgg    900
tggcggcaag caagcgctcg aaacggtgca gcggctgttg ccggtgctgt gccaggacca   960
tggcctgacc ccggaccaag tggtggctat cgccagcaac ggtggcggca agcaagcgct  1020
cgaaacggtg cagcggctgt tgccggtgct gtgccaggac catggcctga ccccggacca  1080
agtggtggct atcgccagca acattggcgg caagcaagcg ctcgaaacgg tgcagcggct  1140
gttgccggtg ctgtgccagg accatggcct gactccggac caagtggtgg ctatcgccag  1200
ccacgatggc ggcaagcaag cgctcgaaac ggtgcagcgg ctgttgccgg tgctgtgcca  1260
ggaccatggc ctgaccccgg accaagtggt ggctatcgcc agcaacattg gcggcaagca  1320
agcgctcgaa acggtgcagc ggctgttgcc ggtgctgtgc caggaccatg gcctgactcc  1380
ggaccaagtg gtggctatcg ccagccacga tggcggcaag caagcgctcg aaacggtgca  1440
gcggctgttg ccggtgctgt gccaggacca tggcctgact ccggaccaag tggtggctat  1500
cgccagccac gatggcggca agcaagcgct cgaaacggtg cagcggctgt tgccggtgct  1560
gtgccaggac catggcctga ctccggacca agtggtggct atcgccagcc acgatggcgg  1620
caagcaagcg ctcgaaacgg tgcagcggct gttgccggtg ctgtgccagg accatggcct  1680
gaccccggac caagtggtgg ctatcgccag caacgtggc ggcaagcaag cgctcgaaac   1740
ggtgcagcgg ctgttgccgg tgctgtgcca ggaccatggc ctgactccgg accaagtggt  1800
ggctatcgcc agccacgatg gcggcaagca agcgctcgaa acggtgcagc ggctgttgcc  1860
ggtgctgtgc caggaccatg gcctgacccc ggaccaagtg gtggctatcg ccagcaacat  1920
tggcggcaag caagcgctcg aaacggtgca gcggctgttg ccggtgctgt gccaggacca  1980
tggcctgacc ccggaccaag tggtggctat cgccagcaac attggcggca agcaagcgct  2040
cgaaacggtg cagcggctgt tgccggtgct gtgccaggac catggcctga ccccggacca  2100
agtggtggct atcgccagca acattggcgg caagcaagcg ctcgaaacgg tgcagcggct  2160
```

-continued

```
gttgccggtg ctgtgccagg accatggcct gaccccggac caagtggtgg ctatcgccag      2220
caacattggc ggcaagcaag cgctcgaaac ggtgcagcgg ctgttgccgg tgctgtgcca      2280
ggaccatggc ctgaccccgg accaagtggt ggctatcgcc agcaaccatg cggcaagca       2340 agcgctcgaa acggtgcagc ggctgttgcc ggtgctgtgc caggaccatg gcctgactcc      2400
ggaccaagtg gtggctatcg ccagccacga tggcggcaag caagcgctcg aaacggtgca      2460
gcggctgttg ccggtgctgt gccaggacca tggcctgacc ccggaccaag tggtggctat      2520
cgccagcaac attggcggca agcaagcgct cgaaagcatt gtggcccagc tgagccggcc      2580
tgatccggcg ttggccgcgt tgaccaacga ccacctcgtc gccttggcct gcctcggcgg      2640
acgtcctgcc atggatgcag tgaaaaaggg attgccgcac gcgccggaat tgatcagaag      2700
agtcaatcgc cgtattggcg aacgcacgtc ccatcgcgtt gccgactacg cgcaagtggt      2760
tcgcgtgctg gagttttttcc agtgccactc ccacccagcg tacgcatttg atgaggccat      2820
gacgcagttc gggatgagca ggaacggggtt ggtacagctc tttcgcagag tgggcgtcac      2880
cgaactcgaa gcccgcggtg aacgctcccc ccagcctcg cagcgttggg accgtatcct      2940
ccaggcatca gggatgaaaa gggccaaacc gtccctact tcagctcaaa caccggatca      3000
ggcgtctttg catgcattcg ccgattcgct ggagcgtgac cttgatgcgc ccagcccaat      3060
gcacgaggga gatcagacgc gggcaagcag ccgtaaacgg tcccgatcgg atcgtgctgt      3120
caccggcccc tccgcacagc aggctgtcga ggtgcgcgtt cccgaacagc gcgatgcgct      3180
gcatttgccc ctcagctgga gggtaaaacg cccgcgtacc aggatctggg gcggcctccc      3240
ggatccgata tctagatccc agctagtgaa atctgaattg gaagagaaga aatctgaact      3300
tagacataaa ttgaaatatg tgccacatga atatattgaa ttgattgaaa tcgcaagaaa      3360
ttcaactcag gatagaatcc ttgaaatgaa ggtgatggag ttctttatga aggtttatgg      3420
ttatcgtggt aaacatttgg gtggatcaag gaaaccagac ggagcaattt atactgtcgg      3480
atctcctatt gattacggtg tgatcgttga tactaaggca tattcaggag gttataatct      3540
tccaattggt caagcagatg aaatgcaaag atatgtcgaa gagaatcaaa caagaaacaa      3600
gcatatcaac cctaatgaat ggtggaaagt ctatccatct tcagtaacag aatttaagtt      3660
cttgtttgtg agtggtcatt tcaaaggaaa ctacaaagct cagcttacaa gattgaatca      3720
tatcactaat tgtaatggag ctgttcttag tgtagaagag cttttgattg gtggagaaat      3780
gattaaagct ggtacattga cacttgagga agtgagaagg aaatttaata acggtgagat      3840
aaacttttaa taggagctc                                                   3859
```

<210> SEQ ID NO 81
<211> LENGTH: 20
<212> TYPE: DNA
<213> ORGANISM: Solanum lycopersicum
<220> FEATURE:
<221> NAME/KEY: source
<222> LOCATION: 1..20
<223> OTHER INFORMATION: mol type=unassigned DNA
      note=CRISPR SlXcv-1
      organism=Solanum lycopersicum

<400> SEQUENCE: 81
tctgtgctgt tgctgtctct                                                     20

<210> SEQ ID NO 82
<211> LENGTH: 24
<212> TYPE: DNA
<213> ORGANISM: Solanum lycopersicum

```
<220> FEATURE:
<221> NAME/KEY: source
<222> LOCATION: 1..24
<223> OTHER INFORMATION: mol type=unassigned DNA
      note=sgRNA SlXcv-1F
      organism=Solanum lycopersicum

<400> SEQUENCE: 82
gatttctgtg ctgttgctgt ctct                                              24

<210> SEQ ID NO 83
<211> LENGTH: 24
<212> TYPE: DNA
<213> ORGANISM: Solanum lycopersicum
<220> FEATURE:
<221> NAME/KEY: source
<222> LOCATION: 1..24
<223> OTHER INFORMATION: mol type=unassigned DNA
      note=sgRNA SlXcv-1R
      organism=Solanum lycopersicum

<400> SEQUENCE: 83
aaacagacac gacaacgaca gaga                                              24

<210> SEQ ID NO 84
<211> LENGTH: 54
<212> TYPE: DNA
<213> ORGANISM: Solanum lycopersicum
<220> FEATURE:
<221> NAME/KEY: source
<222> LOCATION: 1..54
<223> OTHER INFORMATION: mol type=unassigned DNA
      note=SEQ ID NO: 49 szekvencia reszlet: 2253-2306 bp
      organism=Solanum lycopersicum

<400> SEQUENCE: 84
ttggctgctc tgtgctgttg ctgtctcttg gatgcatgct tttgatgctg taaa             54

<210> SEQ ID NO 85
<211> LENGTH: 54
<212> TYPE: DNA
<213> ORGANISM: Solanum lycopersicum
<220> FEATURE:
<221> NAME/KEY: source
<222> LOCATION: 1..54
<223> OTHER INFORMATION: mol type=unassigned DNA
      note=SEQ ID NO:51 szekvencia reszlet: 2616 - 2669 bp
      organism=Solanum lycopersicum

<400> SEQUENCE: 85
ttggctgctc tgtgctgttg ctgtctcttg gatgcatgct tttgagggtg taaa             54

<210> SEQ ID NO 86
<211> LENGTH: 12
<212> TYPE: DNA
<213> ORGANISM: Solanum lycopersicum
<220> FEATURE:
<221> NAME/KEY: source
<222> LOCATION: 1..12
<223> OTHER INFORMATION: mol type=unassigned DNA
      note=Bal oldali ZF feherje celszekvenciaja az SLXcv-1AB genben
      organism=Solanum lycopersicum

<400> SEQUENCE: 86
tgtgctgttg ct                                                           12

<210> SEQ ID NO 87
<211> LENGTH: 12
<212> TYPE: DNA
```

```
<213> ORGANISM: Solanum lycopersicum
<220> FEATURE:
<221> NAME/KEY: source
<222> LOCATION: 1..12
<223> OTHER INFORMATION: mol type=unassigned DNA
      note=Jobb oldali ZF feherje celszekvenciaja az SlXcv-1AB genben
      organism=Solanum lycopersicum

<400> SEQUENCE: 87
tttcgtacgt ag                                                            12

<210> SEQ ID NO 88
<211> LENGTH: 575
<212> TYPE: DNA
<213> ORGANISM: Solanum lycopersicum
<220> FEATURE:
<221> NAME/KEY: source
<222> LOCATION: 1..575
<223> OTHER INFORMATION: mol type=unassigned DNA
      note=Slxcv-1A cDNS
      organism=Solanum lycopersicum

<400> SEQUENCE: 88
tctttctttg tgtctaagca aaagcaccaa cagaaactct ctctacagtt agatccaacc          60
caaattcttc attaattcaa caatgagtta ctacaatcaa caacacccc ctgttggtgt          120 gccaccacca caaggatatc cgccagaagg ttacccaaaa gatgcatacc caccaccagg         180
gtacccacag cagggttacc ctcaacaagg ttacccacct caagggtacc ctccacagta        240
tgcacctcag tatggtgctc cacctcctca tcaacaacaa cagcaatctg gtactggttt        300
catggaagga tgtttggctg ctctgtgctg ttgctgtgat gcatgctttt gatgctgtaa        360
atgatctgtg ccatgtgttg gtggcaaaag tttattaaac caattctatc atagtctaga        420
cttttctctt tgtgttttgt ctttggtgtc ctgtactgtc cttgataaat aatttgatat        480
taaatatgac gatgcacctt gttatggtgg gagaattcaa gtgtctattt gccaatttat        540
acattattgt gcaatgcaag agattctatt ttttt                                   575

<210> SEQ ID NO 89
<211> LENGTH: 640
<212> TYPE: DNA
<213> ORGANISM: Solanum lycopersicum
<220> FEATURE:
<221> NAME/KEY: source
<222> LOCATION: 1..640
<223> OTHER INFORMATION: mol type=unassigned DNA
      note=Slxcv-1B
      organism=Solanum lycopersicum

<400> SEQUENCE: 89
cttagtcctt gtttgacttg ctctataaaa cctaacaaat aaaccccatt tctttgtgca          60
taagcaaaaa ctcaaaactc tcttcaacaa gaaatttcaa ttatgagtta ctacaatcag         120
cagcaacccc ctgttggtgt accaccacca caaggttatc caccagaagg ttactctaaa         180
gatgcatacc caccaccagg gtatcctcag caagggtatc caccacaggg ttatcctcaa        240
caagggtatc cacctccaca gtatgcacct cagtatggtg ctccacctcc tcaacaacat        300
caacagcaat ctagtagcac tggattaatg caaggatgtt tggctgctct gtgctgttgc        360
tgtgatgcat gcttttgagg gtgtaaatga tctgtgccat gtgttgatgg caaaagttta        420
ttgaatcaat tatatcatag tctagacttt tttctttctg tgttttgtcc tatacttact        480
ttgataaata atttgatctt tgatgtgctc aagattccaa agtgtttgtt ttgccaaatt        540
ataggtggtt ggttatgtac aatgtgacag attctatttt tatttttttc aatgttttgg        600
```

```
acctcaaata ttatatgtga atcaatgcac cttgctctgg                              640
```

<210> SEQ ID NO 90
<211> LENGTH: 644
<212> TYPE: DNA
<213> ORGANISM: Capsicum annuum
<220> FEATURE:
<221> NAME/KEY: source
<222> LOCATION: 1..644
<223> OTHER INFORMATION: mol type=unassigned DNA
      note=xcv-1 cDNA
      organism=Capsicum annuum

<400> SEQUENCE: 90

```
ctttactcta taaaaacttc acaaatatca cctcttcact gtaccccatt atctttcttt         60
gtggttaagc aaatacacaa aataaataaa tataactctc ctcttagatt aaactagtag        120
atccatcaac aatgagttac tacaatcaac aacaacctcc tgttggtgta cctccaccac        180
aagggtatcc accagaaggt tacccaaaag attcataccc accacctgga tatccacagc        240
aagggtaccc tcaacaaggg tatccaccac aagggtaccc tccacagtat gcacctcagt        300
atggtgcacc acctcctcaa caacaacatc aatcatctag tagtactgga ttattgcaag        360
gatgtttggc tgctctttgc tgttgctgtg atgcatgctt tgatgctgt  aaatgatctg        420
tacgcaaagt gttgatgaca aaagatgatt gaaatccatt atcatagtct agattatttt        480
ccttgaacgt gttttgtcct tgttgtcctg tcatttataa ataatttgat cttgctatgg        540
tgtctatttg ccaaattata ggtttatgta caacgtgaga gattgtattt tattttttat        600
gttttggacc tcaatatgtg aatcaatgca ccttgatttg gtta                        644
```

<210> SEQ ID NO 91
<211> LENGTH: 652
<212> TYPE: DNA
<213> ORGANISM: Capsicum annuum
<220> FEATURE:
<221> NAME/KEY: source
<222> LOCATION: 1..652
<223> OTHER INFORMATION: mol type=unassigned DNA
      note=Xcv-1 cDNS
      organism=Capsicum annuum

<400> SEQUENCE: 91

```
ctttgacttt actctataaa aacttcacaa atatcacctc ttcactgtac cccattatct        60
ttctttgtgg ttaagcaaat acacaaaata aataaatata actctcctct tagattaaac       120
tagtagatcc atcaacaatg agttactaca atcaacaaca acctcctgtt ggtgtacctc       180
caccacaagg gtatccacca gaaggttacc caaagattc atacccacca cctggatatc       240
cacagcaagg gtaccctcaa caagggtatc caccacaagg gtaccctcca cagtatgcac       300
ctcagtatgg tgcaccacct cctcaacaac aacatcaatc atctagtagt actggattat       360
tgcaaggatg tttggctgct ctttgctgtt gctgtctctt ggatgcatgc ttttgatgct       420
gtaaatgatc tgtacgcaaa gtgttgatga caaaagatga ttgaaatcca ttatcatagt       480
ctagattatt tccttgaac gtgttttgtc cttgttgtcc tgtcatttat aaataatttg       540
atcttgctat ggtgtctatt tgccaaatta taggtttatgt acaacgtga gagattgtat       600
tttattttttt atgttttgga cctcaatatg tgaatcaatg caccttgatt tg              652
```

<210> SEQ ID NO 92
<211> LENGTH: 1271
<212> TYPE: DNA

<213> ORGANISM: Solanum lycopersicum
<220> FEATURE:
<221> NAME/KEY: source
<222> LOCATION: 1..1271
<223> OTHER INFORMATION: mol type=unassigned DNA
    note=HinIII 35Spromoter az SlXe1-amiRNS-t kodolo gen terminator
    szekvencia EcoRI
    organism=Solanum lycopersicum

<400> SEQUENCE: 92

```
aagcttgcca acatggtgga gcacgacact ctcgtctact ccaagaatat caaagataca      60
gtctcagaag accaaagggc tattgagact tttcaacaaa gggtaatatc gggaaacctc     120
ctcggattcc attgcccagc tatctgtcac ttcatcaaaa ggacagtaga aaggaaggt      180
ggcacctaca aatgccatca ttgcgataaa ggaaaggcta tcgttcaaga tgcctctgcc     240
gacagtggtc ccaaagatgg acccccaccc acgaggagca tcgtggaaaa agaagacgtt     300
ccaaccacgt cttcaaagca agtggattga tgtgaacatg gtggagcacg acactctcgt     360
ctactccaag aatatcaaag atacagtctc agaagaccaa aggctattg agacttttca     420
acaaagggta atatcgggaa acctcctcgg attccattgc ccagctatct gtcacttcat     480
caaaaggaca gtagaaaagg aaggtggcac ctacaaatgc catcattgcg ataaaggaaa     540
ggctatcgtt caagatgcct ctgccgacag tggtcccaaa gatggacccc cacccacgag     600
gagcatcgtg gaaaagaag acgttccaac cacgtcttca aagcaagtgg attgatgtga     660
tatctccact gacgtaaggg atgacgcaca atcccactat ccttcgcaag acccttcctc     720
tatataagga agttcatttc atttggagag gacacgctga atcaccagt ctctctctac      780
aaatctatct cttctagaac tagtgattgt gttgatgtcc tttggatgcc aaaaaatcta     840
acaggttaaa ttgagctgct gacctatgga ttcctcagcc ctatctattt atgatttcaa     900
acatatagat aggttttggg tttgcatatg tcaggagctt tattttaccc tttgtttgat     960
cattttcatc caagagacat caacacaatc gaattcgata tcaagcttat cgataccgtc    1020
gacctcgagg ggggggcccgg taccegggga tcctctagag tcgacctgca ggcatgcaag    1080
ctcgagtttc tccataataa tgtgtgagta gttcccagat aagggaatta gggttcctat    1140
agggttcgc tcatgtgttg agcatataag aaacccttag tatgtatttg tatttgtaaa    1200
atacttctat caataaaatt tctaattcct aaaaccaaaa tccagtacta aaatccagat    1260
cccccgaatt c                                                          1271
```

<210> SEQ ID NO 93
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5)
<223> OTHER INFORMATION: Gly or Cys or Leu or Ile or Ala or Trp or Thr
    or Met or Phe or Val

<400> SEQUENCE: 93

```
Cys Xaa Xaa Xaa Xaa Cys Cys Cys Cys Asp
1               5                   10
```

<210> SEQ ID NO 94
<211> LENGTH: 10
<212> TYPE: PRT
<213> ORGANISM: Artificial Sequence
<220> FEATURE:

```
<223> OTHER INFORMATION: Expressed protein domain
<220> FEATURE:
<221> NAME/KEY: MOD_RES
<222> LOCATION: (1) (2) (3) (4) (5)
<223> OTHER INFORMATION: Gly or Cys or Leu or Ile or Ala or Trp or Thr
      or Met or Phe or Val

<400> SEQUENCE: 94

Xaa Xaa Xaa Xaa Xaa Cys Cys Cys Cys Asp
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (6)
<223> OTHER INFORMATION: Gly or Cys or Leu or Ile or Ala or Trp or Thr
      or Met or Phe or Val

<400> SEQUENCE: 95

Cys Xaa Xaa Xaa Xaa Xaa Cys Cys Cys Asp
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (7)
<223> OTHER INFORMATION: Gly or Cys or Leu or Ile or Ala or Trp or Thr
      or Met or Phe or Val

<400> SEQUENCE: 96

Cys Xaa Xaa Xaa Xaa Cys Xaa Cys Cys Asp
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (8)
<223> OTHER INFORMATION: Gly or Cys or Leu or Ile or Ala or Trp or Thr
      or Met or Phe or Val

<400> SEQUENCE: 97

Cys Xaa Xaa Xaa Xaa Cys Cys Xaa Cys Asp
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (9)
<223> OTHER INFORMATION: Gly or Cys or Leu or Ile or Ala or Trp or Thr
      or Met or Phe or Val
```

```
<400> SEQUENCE: 98

Cys Xaa Xaa Xaa Xaa Cys Cys Cys Xaa Asp
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1) (2) (3) (4) (5) (6)
<223> OTHER INFORMATION: Gly or Cys or Leu or Ile or Ala or Trp or Thr
      or Met or Phe or Val

<400> SEQUENCE: 99

Xaa Xaa Xaa Xaa Xaa Xaa Cys Cys Cys Asp
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1) (2) (3) (4) (5) (7)
<223> OTHER INFORMATION: Gly or Cys or Leu or Ile or Ala or Trp or Thr
      or Met or Phe or Val

<400> SEQUENCE: 100

Xaa Xaa Xaa Xaa Xaa Cys Xaa Cys Cys Asp
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (6) (7)
<223> OTHER INFORMATION: Gly or Cys or Leu or Ile or Ala or Trp or Thr
      or Met or Phe or Val

<400> SEQUENCE: 101

Cys Xaa Xaa Xaa Xaa Xaa Xaa Cys Cys Asp
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (7) (9)
<223> OTHER INFORMATION: Gly or Cys or Leu or Ile or Ala or Trp or Thr
      or Met or Phe or Val

<400> SEQUENCE: 102

Cys Xaa Xaa Xaa Xaa Cys Xaa Cys Xaa Asp
1               5                   10

<210> SEQ ID NO 103
```

-continued

```
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2)(3)(4)(5)(8)(9)
<223> OTHER INFORMATION: Gly or Cys or Leu or Ile or Ala or Trp or Thr
      or Met or Phe or Val

<400> SEQUENCE: 103

Cys Xaa Xaa Xaa Xaa Cys Cys Xaa Xaa Asp
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2)(3)(4)(5)
<223> OTHER INFORMATION: Gly or Cys or Leu or Ile or Ala or Trp or Thr
      or Met or Phe or Val

<400> SEQUENCE: 104

Cys Xaa Xaa Xaa Xaa Cys Cys Cys Cys Glu
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1)(2)(3)(4)(5)
<223> OTHER INFORMATION: Gly or Cys or Leu or Ile or Ala or Trp or Thr
      or Met or Phe or Val

<400> SEQUENCE: 105

Xaa Xaa Xaa Xaa Xaa Cys Cys Cys Cys Glu
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2)(3)(4)(5)(6)
<223> OTHER INFORMATION: Gly or Cys or Leu or Ile or Ala or Trp or Thr
      or Met or Phe or Val

<400> SEQUENCE: 106

Cys Xaa Xaa Xaa Xaa Xaa Cys Cys Cys Glu
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
```

```
<222> LOCATION: (2) (3) (4) (5) (7)
<223> OTHER INFORMATION: Gly or Cys or Leu or Ile or Ala or Trp or Thr
      or Met or Phe or Val

<400> SEQUENCE: 107

Cys Xaa Xaa Xaa Xaa Cys Xaa Cys Cys Glu
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (8)
<223> OTHER INFORMATION: Gly or Cys or Leu or Ile or Ala or Trp or Thr
      or Met or Phe or Val

<400> SEQUENCE: 108

Cys Xaa Xaa Xaa Xaa Cys Cys Xaa Cys Glu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (9)
<223> OTHER INFORMATION: Gly or Cys or Leu or Ile or Ala or Trp or Thr
      or Met or Phe or Val

<400> SEQUENCE: 109

Cys Xaa Xaa Xaa Xaa Cys Cys Cys Xaa Glu
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1) (2) (3) (4) (5) (6)
<223> OTHER INFORMATION: Gly or Cys or Leu or Ile or Ala or Trp or Thr
      or Met or Phe or Val

<400> SEQUENCE: 110

Xaa Xaa Xaa Xaa Xaa Xaa Cys Cys Cys Glu
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1) (2) (3) (4) (5) (7)
<223> OTHER INFORMATION: Gly or Cys or Leu or Ile or Ala or Trp or Thr
      or Met or Phe or Val

<400> SEQUENCE: 111

Xaa Xaa Xaa Xaa Xaa Cys Xaa Cys Cys Glu
```

```
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (6) (7)
<223> OTHER INFORMATION: Gly or Cys or Leu or Ile or Ala or Trp or Thr
      or Met or Phe or Val

<400> SEQUENCE: 112

Cys Xaa Xaa Xaa Xaa Xaa Xaa Cys Cys Glu
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (7) (9)
<223> OTHER INFORMATION: Gly or Cys or Leu or Ile or Ala or Trp or Thr
      or Met or Phe or Val

<400> SEQUENCE: 113

Cys Xaa Xaa Xaa Xaa Cys Xaa Cys Xaa Glu
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Expressed protein domainn
<220> FEATURE:
<221> NAME/KEY: MOD_RES
<222> LOCATION: (2) (3) (4) (5) (8) (9)
<223> OTHER INFORMATION: Gly or Cys or Leu or Ile or Ala or Trp or Thr
      or Met or Phe or Val

<400> SEQUENCE: 114

Cys Xaa Xaa Xaa Xaa Cys Cys Xaa Xaa Glu
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5)
<223> OTHER INFORMATION: Gly or Cys or Leu or Ile or Ala or Trp or Thr
      or Met or Phe or Val

<400> SEQUENCE: 115

Cys Xaa Xaa Xaa Xaa Cys Cys Cys Cys Asn
1               5                   10

<210> SEQ ID NO 116
<211> LENGTH: 10
<212> TYPE: PRT
<213> ORGANISM: Artificial Sequence
```

```
<220> FEATURE:
<223> OTHER INFORMATION: Expressed protein domain
<220> FEATURE:
<221> NAME/KEY: MOD_RES
<222> LOCATION: (1) (2) (3) (4) (5)
<223> OTHER INFORMATION: Gly or Cys or Leu or Ile or Ala or Trp or Thr
      or Met or Phe or Val

<400> SEQUENCE: 116

Xaa Xaa Xaa Xaa Xaa Cys Cys Cys Cys Asn
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (6)
<223> OTHER INFORMATION: Gly or Cys or Leu or Ile or Ala or Trp or Thr
      or Met or Phe or Val

<400> SEQUENCE: 117

Cys Xaa Xaa Xaa Xaa Xaa Cys Cys Cys Asn
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (7)
<223> OTHER INFORMATION: Gly or Cys or Leu or Ile or Ala or Trp or Thr
      or Met or Phe or Val

<400> SEQUENCE: 118

Cys Xaa Xaa Xaa Xaa Cys Xaa Cys Cys Asn
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Expressed protein domainn
<220> FEATURE:
<221> NAME/KEY: MOD_RES
<222> LOCATION: (2) (3) (4) (5) (8)
<223> OTHER INFORMATION: Gly or Cys or Leu or Ile or Ala or Trp or Thr
      or Met or Phe or Val

<400> SEQUENCE: 119

Cys Xaa Xaa Xaa Xaa Cys Cys Xaa Cys Asn
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (9)
<223> OTHER INFORMATION: Gly or Cys or Leu or Ile or Ala or Trp or Thr
      or Met or Phe or Val
```

```
<400> SEQUENCE: 120

Cys Xaa Xaa Xaa Xaa Cys Cys Cys Xaa Asn
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1) (2) (3) (4) (5) (6)
<223> OTHER INFORMATION: Gly or Cys or Leu or Ile or Ala or Trp or Thr
      or Met or Phe or Val

<400> SEQUENCE: 121

Xaa Xaa Xaa Xaa Xaa Xaa Cys Cys Cys Asn
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (1) (2) (3) (4) (5) (7)
<223> OTHER INFORMATION: Gly or Cys or Leu or Ile or Ala or Trp or Thr
      or Met or Phe or Val

<400> SEQUENCE: 122

Xaa Xaa Xaa Xaa Xaa Cys Xaa Cys Cys Asn
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (6) (7)
<223> OTHER INFORMATION: Gly or Cys or Leu or Ile or Ala or Trp or Thr
      or Met or Phe or Val

<400> SEQUENCE: 123

Cys Xaa Xaa Xaa Xaa Xaa Xaa Cys Cys Asn
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2) (3) (4) (5) (7) (9)
<223> OTHER INFORMATION: Gly or Cys or Leu or Ile or Ala or Trp or Thr
      or Met or Phe or Val

<400> SEQUENCE: 124

Cys Xaa Xaa Xaa Xaa Cys Xaa Cys Xaa Asn
1               5                   10
```

```
<210> SEQ ID NO 125
<211> LENGTH: 10
<212> TYPE: PRT
<213> ORGANISM: Artificial Sequence
<220> FEATURE:
<223> OTHER INFORMATION: Expressed protein domain
<220> FEATURE:
<221> NAME/KEY: MOD_RES
<222> LOCATION: (2)(3)(4)(5)(8)(9)
<223> OTHER INFORMATION: Gly or Cys or Leu or Ile or Ala or Trp or Thr
      or Met or Phe or Val

<400> SEQUENCE: 125

Cys Xaa Xaa Xaa Xaa Cys Cys Xaa Xaa Asn
1               5                   10

<210> SEQ ID NO 126
<211> LENGTH: 45
<212> TYPE: PRT
<213> ORGANISM: Capsicum annuum

<400> SEQUENCE: 126

Gly Tyr Pro Pro Glu Gly Tyr Pro Lys Asp Ser Tyr Pro Pro Pro Gly
1               5                   10                  15

Tyr Pro Gln Gln Gly Tyr Pro Gln Gln Gly Tyr Pro Gln Gln Gly Tyr
            20                  25                  30

Pro Pro Gln Gly Tyr Pro Pro Gln Tyr Ala Pro Gln Tyr
        35                  40                  45

<210> SEQ ID NO 127
<211> LENGTH: 10
<212> TYPE: PRT
<213> ORGANISM: Solanum lycopersicum

<400> SEQUENCE: 127

Cys Cys Cys Cys Leu Leu Asp Ala Cys Phe
1               5                   10

<210> SEQ ID NO 128
<211> LENGTH: 42
<212> TYPE: RNA
<213> ORGANISM: Solanum lycopersicum

<400> SEQUENCE: 128
gcugcucugu gcuguugcug ucucuuggau gcaugcuuuu ga                    42

<210> SEQ ID NO 129
<211> LENGTH: 21
<212> TYPE: RNA
<213> ORGANISM: Solanum lycopersicum

<400> SEQUENCE: 129
cacaacuaca gagaaccuac u                                           21

<210> SEQ ID NO 130
<211> LENGTH: 75
<212> TYPE: DNA
<213> ORGANISM: Solanum lycopersicum

<400> SEQUENCE: 130
ttttgcagtt tggctgctct gtgctgttgc tgtctcttgg atgcatgctt ttgatgctgt  60
aaatgatctg tgcca                                                  75

<210> SEQ ID NO 131
```

```
<211> LENGTH: 75
<212> TYPE: DNA
<213> ORGANISM: Solanum lycopersicum

<400> SEQUENCE: 131
aaaacgtcaa accgacgaga cacgacaacg acagagaacc tacgtacgaa aactacgaca      60
tttactagac acggt                                                      75

<210> SEQ ID NO 132
<211> LENGTH: 14
<212> TYPE: PRT
<213> ORGANISM: Solanum lycopersicum

<400> SEQUENCE: 132

Leu Ala Ala Leu Cys Cys Cys Cys Leu Leu Asp Ala Cys Phe
1               5                   10

<210> SEQ ID NO 133
<211> LENGTH: 75
<212> TYPE: DNA
<213> ORGANISM: Solanum lycopersicum

<400> SEQUENCE: 133
ttttgcagtt tggctgctct gtgctgttgc tgtctcttgg atgcatgctt ttgagggtgt      60
aaatgatctg tgcca                                                      75

<210> SEQ ID NO 134
<211> LENGTH: 75
<212> TYPE: DNA
<213> ORGANISM: Solanum lycopersicum

<400> SEQUENCE: 134
aaaacgtcaa accgacgaga cacgacaacg acagagaacc tacgtacgaa aactcccaca      60
tttactagac acggt                                                      75

<210> SEQ ID NO 135
<211> LENGTH: 14
<212> TYPE: PRT
<213> ORGANISM: Solanum lycopersicum

<400> SEQUENCE: 135

Leu Ala Ala Leu Cys Cys Cys Cys Leu Leu Asp Ala Cys Phe
1               5                   10

<210> SEQ ID NO 136
<211> LENGTH: 17
<212> TYPE: PRT
<213> ORGANISM: Solanum lycopersicum

<400> SEQUENCE: 136

Thr Gly Gly Cys Thr Gly Cys Thr Cys Thr Gly Thr Gly Cys Thr Gly
1               5                   10                  15

Thr

<210> SEQ ID NO 137
<211> LENGTH: 17
<212> TYPE: PRT
<213> ORGANISM: Solanum lycopersicum

<400> SEQUENCE: 137

Thr Thr Ala Cys Ala Gly Cys Ala Thr Cys Ala Ala Ala Ala Gly Cys
1               5                   10                  15
```

Ala

<210> SEQ ID NO 138
<211> LENGTH: 17
<212> TYPE: PRT
<213> ORGANISM: Solanum lycopersicum

<400> SEQUENCE: 138

Thr Thr Ala Cys Ala Cys Cys Cys Thr Cys Ala Ala Ala Ala Gly Cys
1               5                   10                  15

Ala

<210> SEQ ID NO 139
<211> LENGTH: 54
<212> TYPE: DNA
<213> ORGANISM: Solanum lycopersicum

<400> SEQUENCE: 139
ttggctgctc tgtgctgttg ctgtctcttg gatgcatgct tttgatgctg taaa         54

<210> SEQ ID NO 140
<211> LENGTH: 48
<212> TYPE: DNA
<213> ORGANISM: Artificial Sequence
<220> FEATURE:
<223> OTHER INFORMATION: Variant 1 of Slxcv-1A gene

<400> SEQUENCE: 140
ttggctgctc tgtgctgttg ctgtgatgca tgcttttgat gctgtaaa              48

<210> SEQ ID NO 141
<211> LENGTH: 12
<212> TYPE: PRT
<213> ORGANISM: Artificial Sequence
<220> FEATURE:
<223> OTHER INFORMATION: Amino acid sequence of Variant 1 of the
      Slxcv-1A gene

<400> SEQUENCE: 141

Leu Ala Ala Leu Cys Cys Cys Cys Asp Ala Cys Phe
1               5                   10

<210> SEQ ID NO 142
<211> LENGTH: 54
<212> TYPE: DNA
<213> ORGANISM: Solanum lycopersicum

<400> SEQUENCE: 142
ttggctgctc tgtgctgttg ctgtctcttg gatgcatgct tttgagggtg taaa         54

<210> SEQ ID NO 143
<211> LENGTH: 48
<212> TYPE: DNA
<213> ORGANISM: Artificial Sequence
<220> FEATURE:
<223> OTHER INFORMATION: Variant 1 of the Slxcv-1B gene

<400> SEQUENCE: 143
ttggctgctc tgtgctgttg ctgtgatgca tgcttttgag ggtgtaaa               48

<210> SEQ ID NO 144
<211> LENGTH: 12
<212> TYPE: PRT
<213> ORGANISM: Artificial Sequence

```
<220> FEATURE:
<223> OTHER INFORMATION: Amino acid sequence of Variant 1 of the
      Slxcv-1B gene

<400> SEQUENCE: 144

Leu Ala Ala Leu Cys Cys Cys Cys Asp Ala Cys Phe
1               5                   10

<210> SEQ ID NO 145
<211> LENGTH: 54
<212> TYPE: DNA
<213> ORGANISM: Solanum lycopersicum

<400> SEQUENCE: 145
ttggctgctc tgtgctgttg ctgtctcttg gatgcatgct tttgagggtg taaa          54

<210> SEQ ID NO 146
<211> LENGTH: 38
<212> TYPE: DNA
<213> ORGANISM: Artificial Sequence
<220> FEATURE:
<223> OTHER INFORMATION: Variant 2 of the Slxcv-1B gene

<400> SEQUENCE: 146
ttggctgctc tgtgcttgca tgcttttgat gctgtaaa                            38

<210> SEQ ID NO 147
<211> LENGTH: 12
<212> TYPE: PRT
<213> ORGANISM: Artificial Sequence
<220> FEATURE:
<223> OTHER INFORMATION: Amino acid sequence of Variant 2 of the
      Slxcv-1B gene

<400> SEQUENCE: 147

Leu Ala Ala Leu Cys Leu His Ala Phe Asp Ala Val
1               5                   10

<210> SEQ ID NO 148
<211> LENGTH: 54
<212> TYPE: DNA
<213> ORGANISM: Solanum lycopersicum

<400> SEQUENCE: 148
ttggctgctc tgtgctgttg ctgtctcttg gatgcatgct tttgatgctg taaa          54

<210> SEQ ID NO 149
<211> LENGTH: 24
<212> TYPE: DNA
<213> ORGANISM: Artificial Sequence
<220> FEATURE:
<223> OTHER INFORMATION: Variant 3 of the Slxcv-1A gene

<400> SEQUENCE: 149
ttggctgctc tgtgagggtg taaa                                           24

<210> SEQ ID NO 150
<211> LENGTH: 4
<212> TYPE: PRT
<213> ORGANISM: Artificial Sequence
<220> FEATURE:
<223> OTHER INFORMATION: Amino acid sequence of Variant 3 of the
      Slxcv-1A gene
```

```
<400> SEQUENCE: 150

Leu Ala Ala Leu
1

<210> SEQ ID NO 151
<211> LENGTH: 4
<212> TYPE: PRT
<213> ORGANISM: Capsicum annuum

<400> SEQUENCE: 151

Gly Tyr Pro Gln
1
```